US005576293A

United States Patent [19]

deSolms et al.

[11] Patent Number: 5,576,293
[45] Date of Patent: Nov. 19, 1996

[54] INHIBITORS OF FARNESYL-PROTEIN TRANSFERASE

[75] Inventors: S. Jane deSolms, Norristown; Victor M. Garsky, Blue Bell; Elizabeth A. Giuliani, Lansdale; Robert P. Gomez, Perkasie; Samuel L. Graham, Schwenksville; Gerald E. Stokker, Gwynedd Valley; Catherine M. Wiscount, Allentown, all of Pa.

[73] Assignee: Merck & Co., Inc., Rahway, N.J.

[21] Appl. No.: 314,987

[22] Filed: Sep. 29, 1994

Related U.S. Application Data

[63] Continuation-in-part of Ser. No. 129,868, Sep. 30, 1993, abandoned.
[51] Int. Cl.$^6$ .............................. A61K 38/00; C07K 5/00; C07K 7/00; C07K 17/00
[52] U.S. Cl. .............................. 514/19; 514/18; 546/216; 548/550; 530/330; 530/331
[58] Field of Search ........................ 514/18, 19; 530/330, 530/331; 546/216; 548/550

[56] References Cited

U.S. PATENT DOCUMENTS

| 5,043,268 | 8/1991 | Stock ......................................... 435/15 |
| 5,141,851 | 8/1992 | Brown et al. .............................. 435/15 |
| 5,238,922 | 8/1993 | Graham et al. ........................... 514/18 |
| 5,326,773 | 7/1994 | De Solms et al. ........................ 514/336 |
| 5,340,828 | 8/1994 | Graham et al. .......................... 514/357 |
| 5,352,705 | 10/1994 | Deana et al. .............................. 514/630 |

FOREIGN PATENT DOCUMENTS

| 0456180A1 | 11/1991 | European Pat. Off. . |
| 0618221A2 | 10/1994 | European Pat. Off. . |
| WO91/16340 | 10/1991 | WIPO . |

OTHER PUBLICATIONS

Gibbs, J. B. et al., "Selective Inhibition of Farnesyl–Protein Transferase Blocks Ras Processing in Vivo", The Journal of Biological Chemistry, vol. 268, No. 11, pp. 7617–7620 (1993).

Goldstein, J. L. et al., "Nonfarnesylated Tetrapeptide Inhibitors of Protein Farnesyltransferase", The Journal of Biological Chemistry, vol. 266, No. 24 pp. 15575–15578 (1991).
James, G. L. et al., "Benzodiazepine Peptidomimetic BZA–5B Interrupts the MAP Kinase Activation Pathway in H–Ras–transformed Rat–1 Cells, but Not in Untransformed Cells", The Journal of Biological Chemistry, vol. 369, No. 44, pp. 27705–27714 (1994).
James, G. L. et al., "Benzodiazepine Peptidomimetics: Potent Inhibitors of RasFarnesylation in Animal Cells", Science, vol. 260, pp. 1937–1942 (1993).
Kohl, N. E. et al., "Selective Inhibition of ras–Dependent Transformation by a Farnesyltransferase Inhibitor", Science, vol. 260, pp. 1934–1937 (1993).
Kohl, N. E. et al., "Protein farnesyltransferase inhibitors block the growth of ras–dependent tumors in nude mice", Proc. Natl. Acad. Sci. USA, Med. Sciences, vol. 91, pp. 9141–9145 (1994).
Pompliano, D. L., "Steady–State Kinetic Mechanism of Ras Farnesyl:Protein Transferase", Biochemistry, vol. 31, pp. 3800–3807 (1992).
Ser. No. 07/968,022 Merck & Co., Inc. Filing Date 10/29/92.
Ser. No. 08/143,943 Merck & Co., Inc. Filing Date 10/27/93.

Primary Examiner—Toni R. Scheiner
Assistant Examiner—Sheela J. Huff
Attorney, Agent, or Firm—David A. Muthard; Mark R. Daniel

[57] ABSTRACT

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

25 Claims, No Drawings

INHIBITORS OF FARNESYL-PROTEIN TRANSFERASE

RELATED APPLICATION

The present patent application is a continuation-in-part application of application Ser. No. 08/129,868, filed Sep. 30, 1993 now abandoned.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., Nature 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et at., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et at., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosollocalized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et at., *PNAS*, 88:732–736 (1991)). Such inhibitors may inhibit while serving as alternate substrates for the Ras farnesyl-transferase enzyme, or may be purely competitive inhibitors (U.S. Pat. No. 5,141, 851, University of Texas).

It has also been demonstrated that certain inhibitors of farnesyl-protein transferase selectively block the processing of Ras oncoprotein intracellularly (N.E. Kohl et al., *Science*, 260:1934–1937 (1993) and G. L. James et al., *Science*, 260:1937–1942 (1993).

Recently, it has been shown that an inhibitor of farnesyl-protein transferase blocks the growth of ras-dependent tumors in nude mice (N.E. Kohl et al., *Proc. Natl. Acad. Sci U.S.A.*, 91:9141–9145 (1994).

Inhibitors of Ras farnesyl-protein transferase (FPTase) have been described in two general classes. The first are analogs of farnesyl diphosphate (FPP), while the second class of inhibitors is related to the protein substrate for the enzyme, Ras. Almost all of the peptide derived inhibitors that have been described are cysteine containing molecules that are related to the CAAX motif that is the signal for protein prenylation. The exception to this generalization is a class of natural products known as the pepticinnamins (Omura, et al., *J. Antibiotics* 46:222 (1993). In general, deletion of the thiol from a CAAX derivative dramatically reduces the inhibitory potency of these compounds. However, the thiol group potentially places limitations on the therapeutic application of FPTase inhibitors with respect to pharmacokinetics, pharmacodynamics and toxicity. Therefore, a functional replacement for the thiol is desirable. With the exception of the pepticinnamins, non-thiol FPTase inhibitors that are competitive with the Ras substrate have not been described and are the subject of this invention.

It is, therefore, an object of this invention to develop tetrapeptide-based compounds which do not have a thiol moiety, and which will inhibit farnesyl transferase and the post-translational functionalization of the oncogene Ras protein. It is a further object of this invention to develop chemotherapeutic compositions containing the compounds of this invention and methods for producing the compounds of this invention.

SUMMARY OF THE INVENTION

The present invention comprises analogs of the CAAX motif of the protein Ras that is modified by farnesylation in vivo. These CAAX analogs inhibit the farnesylation of Ras. Furthermore, these CAAX analogues differ from those previously described as inhibitors of Ras farnesyl transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formulae:

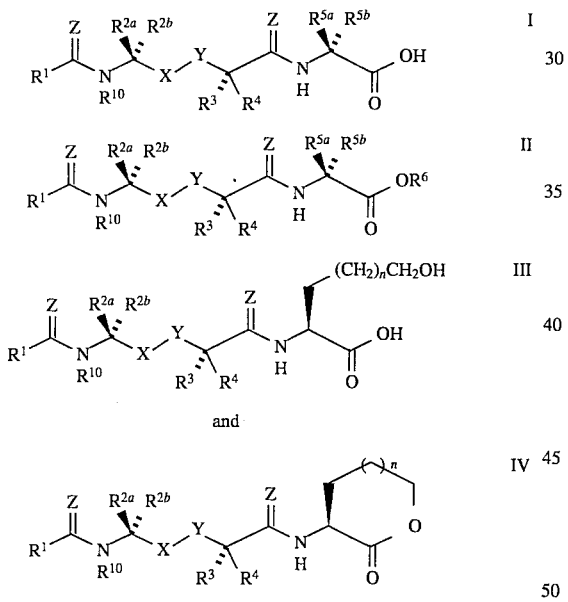

DETAILED DESCRIPTION OF THE INVENTION

The compounds of this invention inhibit the farnesylation of Ras. In a first embodiment of this invention, the Ras farnesyl transferase inhibitors are illustrated by the formula I:

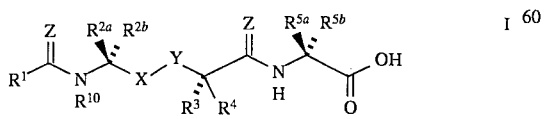

wherein:

$R^1$ is selected from:
  a) heterocycle, and
  b) $C_1$–$C_{10}$ alkyl, which is substituted with heterocycle and which is optionally substituted with one or more of $C_1$–$C_4$ alkyl, hydroxy or amino groups;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group, wherein the substituent is selected from F, Cl, Br, $NO_2$, $R^{8O}O$—, $R^9S(O)m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or
  $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $N(R^8)_2$, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl; or
  $R^3$ and $R^4$ are combined to form —$(CH_2)_s$—;

$R^{5a}$ and $R^{5b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocycle group,
    wherein the substituent is selected from F, Cl, Br, $N(R^8)_2$, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl; or
  $R^{5a}$ and $R^{5b}$ are combined to form —$(CH_2)_s$— wherein one of the carbon atoms is optionally replaced by a moiety selected from: O, $S(O)_m$, —$NC(O)$—, and —$N(COR^8)$—;

X-Y is

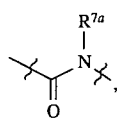

a)

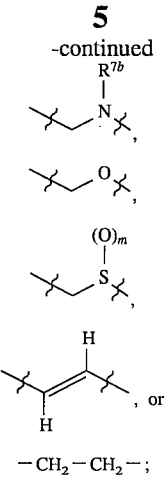

b) 
R$^{7b}$
\—N\— c) \—O\— d) 
(O)$_m$
\—S\— e) 
H    
\=/
/   \
H

, or f) —CH$_2$—CH$_2$—;

R$^{7a}$ is selected from
- a) hydrogen,
- b) unsubstituted or substituted aryl,
- c) unsubstituted or substituted heterocyclic,
- d) unsubstituted or substituted cycloalkyl, and
- e) C$_1$–C$_6$ alkyl substituted with hydrogen or an unsubstituted or substituted group selected from aryl, heterocyclic and cycloalkyl;

R$^{7b}$ is selected from
- a) hydrogen,
- b) unsubstituted or substituted aryl,
- c) unsubstituted or substituted heterocyclic,
- d) unsubstituted or substituted cycloalkyl,
- e) C$_1$–C$_6$ alkyl substituted with hydrogen or an unsubstituted or substituted group selected from aryl, heterocyclic and cycloalkyl,
- f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
- g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from hydrogen, C$_1$–C$_6$ alkyl and aryl;

R$^9$ is independently selected from C$_1$–C$_6$ alkyl and aryl;

R$^{10}$ is independently selected from hydrogen and C$_1$–C$_6$ alkyl;

Z is independently H$_2$ or O;

m is 0, 1 or 2; and s is 4 or 5;

or the pharmaceutically acceptable salts thereof.

In a second embodiment of this invention the prodrugs of compounds of formula I are illustrated by the formula II:

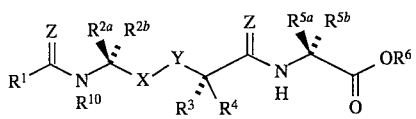

II wherein:

R$^1$ is selected from:
- a) heterocycle, and
- b) C$_1$–C$_{10}$ alkyl, which is substituted with heterocycle and which is optionally substituted with one or more of C$_1$–C$_4$ alkyl, hydroxy or amino groups;

R$^{2a}$ and R$^{2b}$ are independently selected from:
- a) a side chain of a naturally occurring amino acid,
- b) an oxidized form of a side chain of a naturally occurring amino acid which is:
  - i) methionine sulfoxide, or
  - ii) methionine sulfone,
- c) substituted or unsubstituted C$_1$–C$_{20}$ alkyl, C$_2$–C$_{20}$ alkenyl, C$_3$–C$_{10}$ cycloalkyl, aryl or heterocyclic group,
  wherein the substituent is selected from F, Cl, Br, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
- d) C$_1$–C$_6$ alkyl substituted with an unsubstituted or substituted group selected from aryl, heterocycle and C$_3$–C$_{10}$ cycloalkyl; or R$^{2a}$ and R$^{2b}$ are combined to form —(CH$_2$)$_s$—;

R$^3$ and R$^4$ are independently selected from:
- a) a side chain of a naturally occurring amino acid,
- b) an oxidized form of a side chain of a naturally occurring amino acid which is:
  - i) methionine sulfoxide, or
  - ii) methionine sulfone, and
- c) substituted or unsubstituted C$_1$–C$_{20}$ alkyl, C$_2$–C$_{20}$ alkenyl, C$_3$–C$_{10}$ cycloalkyl, aryl or heterocyclic group,
  wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
- d) C$_1$–C$_6$ alkyl substituted with an unsubstituted or substituted group selected from aryl, heterocyclic and C$_3$–C$_{10}$ cycloalkyl; or R$^3$ and R$^4$ are combined to form —(CH$_2$)$_s$—;

R$^{5a}$ and R$^{5b}$ are independently selected from:
- a) a side chain of a naturally occurring amino acid,
- b) an oxidized form of a side chain of a naturally occurring amino acid which is:
  - i) methionine sulfoxide, or
  - ii) methionine sulfone,
- c) substituted or unsubstituted C$_1$–C$_{20}$ alkyl, C$_2$–C$_{20}$ alkenyl, C$_3$–C$_{10}$ cycloalkyl, aryl or heterocycle group,
  wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
- d) C$_1$–C$_6$ alkyl substituted with an unsubstituted or substituted group selected from aryl, heterocyclic and C$_3$–C$_{10}$ cycloalkyl; or R$^{5a}$ and R$^{5b}$ are combined to form —(CH$_2$)$_s$— wherein one of the carbon atoms is optionally replaced by a moiety selected from: O, S(O)$_m$, —NC(O)—, and —N(COR$^8$)—;

R$^6$ is
- a) substituted or unsubstituted C$_1$–C$_8$ alkyl, wherein the substituent on the alkyl is selected from:
  1) aryl,
  2) heterocycle,
  3) —N(R$^9$)$_2$,
  4) —OR$^8$, or b) 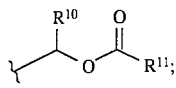

X-Y is a) 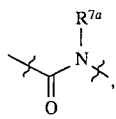

b) 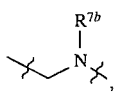

c) 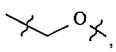

d) 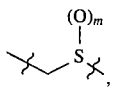

e) 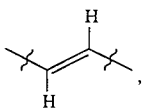

f) —CH$_2$—CH$_2$—;

R$^{7a}$ is selected from
a) hydrogen,
b) unsubstituted or substituted aryl,
c) unsubstituted or substituted heterocyclic,
d) unsubstituted or substituted cycloalkyl, and
e) C$_1$–C$_6$ alkyl substituted with hydrogen or an unsubstituted or substituted group selected from aryl, heterocyclic and cycloalkyl;

R$^{7b}$ is selected from
a) hydrogen,
b) unsubstituted or substituted aryl,
c) unsubstituted or substituted heterocyclic,
d) unsubstituted or substituted cycloalkyl,
e) C$_1$–C$_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from hydrogen, C$_1$–C$_6$ alkyl and aryl;

R$^9$ is independently selected from C$_1$–C$_6$ alkyl and aryl;

R$^{10}$ is independently selected from hydrogen and C$_1$–C$_6$ alkyl;

R$^{11}$ is independently selected from C$_1$–C$_6$ alkyl;

Z is independently H$_2$ or O;

m is 0, 1 or 2; and s is 4 or 5;

or the pharmaceutically acceptable salts.

In a third embodiment of this invention, the inhibitors of farnesyl transferase are illustrated by the formula III:

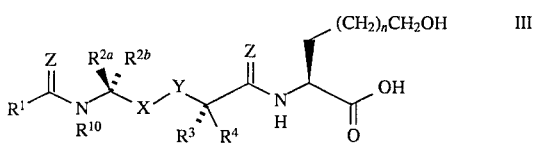

wherein:

R$^1$ is selected from:
a) heterocycle, and
b) C$_1$–C$_{10}$ alkyl, which is substituted with heterocycle and which is optionally substituted with one or more of C$_1$–C$_4$ alkyl, hydroxy or amino groups;

R$^{2a}$ and R$^{2b}$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted C$_1$–C$_{20}$ alkyl, C$_2$–C$_{20}$ alkenyl, C$_3$–C$_{10}$ cycloalkyl, aryl or heterocyclic group,
  wherein the substituent is selected from F, Cl, Br, NO$_2$, R$^8$O—R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
d) C$_1$–C$_6$ alkyl substituted with an unsubstituted or substituted group selected from aryl, heterocycle and C$_3$–C$_{10}$ cycloalkyl; or
R$^{2a}$ and R$^{2b}$ are combined to form —(CH$_2$)$_s$—;

R$^3$ and R$^4$ are independently selected from:
a) a side chain of a naturally occurring amino acid,
b) an oxidized form of a side chain of a naturally occurring amino acid which is:
  i) methionine sulfoxide, or
  ii) methionine sulfone, and
c) substituted or unsubstituted C$_1$–C$_{20}$ alkyl, C$_2$–C$_{20}$ alkenyl, C$_3$–C$_{10}$ cycloalkyl, aryl or heterocyclic group,
  wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
d) C$_1$–C$_6$ alkyl substituted with an unsubstituted or substituted group selected from aryl, heterocyclic and C$_3$–C$_{10}$ cycloalkyl; or
R$^3$ and R$^4$ are combined to form —(CH$_2$)$_s$—;

X-Y is
a) 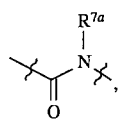

b) 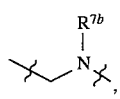

c) 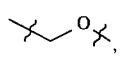

d) 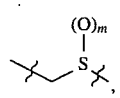

e) 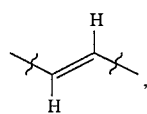

f) —CH$_2$—CH$_2$—;

R$^{7a}$ is selected from
  a) hydrogen,
  b) unsubstituted or substituted aryl,
  c) unsubstituted or substituted heterocyclic,
  d) unsubstituted or substituted cycloalkyl, and
  e) C$_1$–C$_6$ alkyl substituted with hydrogen or an unsubstituted or substituted group selected from aryl, heterocyclic and cycloalkyl;

R$^{7b}$ is selected from
  a) hydrogen,
  b) unsubstituted or substituted aryl,
  b) unsubstituted or substituted aryl,
  c) unsubstituted or substituted heterocyclic,
  d) unsubstituted or substituted cycloalkyl,
  e) C$_1$–C$_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from hydrogen, C$_1$–C$_6$ alkyl and aryl;

R$^9$ is independently selected from C$_1$–C$_6$ alkyl and aryl;

R$^{10}$ is independently selected from hydrogen and C$_1$–C$_6$ alkyl;

Z is H$_2$ or O;

m is 0, 1 or 2;

n is 0, 1 or 2; and s is 4 or 5;

or the pharmaceutically acceptable salts thereof.

In a fourth embodiment of this invention the prodrugs of compounds of formula HI are illustrated by the formula IV:

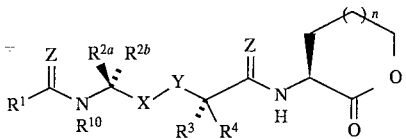

IV wherein:

R$^1$ is selected from:
  a) heterocycle, and
  b) C$_1$–C$_{10}$ alkyl, which is substituted with heterocycle and which is optionally substituted with one or more of C$_1$–C$_4$ alkyl, hydroxy or amino groups;

R$^{2a}$ and R$^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted C$_1$–C$_{20}$ alkyl, C$_2$–C$_{20}$ alkenyl, C$_3$–C$_{10}$ cycloalkyl, aryl or heterocyclic group,
    wherein the substituent is selected from F, Cl, Br, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
  d) C$_1$–C$_6$ alkyl substituted with an unsubstituted or substituted group selected from aryl, heterocycle and C$_3$–C$_{10}$ cycloalkyl; or
  R$^{2a}$ and R$^{2b}$ are combined to form —(CH$_2$)$_s$—;

R$^3$ and R$^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted C$_1$–C$_{20}$ alkyl, C$_2$–C$_{20}$ alkenyl, C$_3$–C$_{10}$ cycloalkyl, aryl or heterocyclic group,
    wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
  d) C$_1$–C$_6$ alkyl substituted with an unsubstituted or substituted group selected from aryl, heterocyclic and C$_3$–C$_{10}$ cycloalkyl; or
  R$^3$ and R$^4$ are combined to form —(CH$_2$)$_s$—;

X-Y is
a) 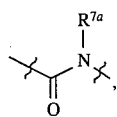

b)

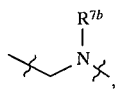

c)

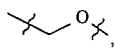

d)

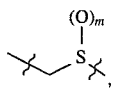

e)

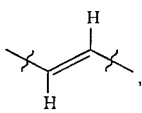

f) —CH₂—CH₂—;

$R^7$ a is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1$–$C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from hydrogen, $C_1$–$C_6$ alkyl and aryl;

$R^9$ is independently selected from $C_1$–$C_6$ alkyl and aryl;

$R^{10}$ is independently selected from hydrogen and $C_1$–$C_6$ alkyl;

Z is $H_2$ or O;

m is 0, 1 or 2;

n is 0, 1 or 2; and s is 4 or 5;

or the pharmaceutically acceptable salts.

In a more preferred embodiment of this invention, the Ras farnesyl transferase inhibitors are illustrated by the formula I:

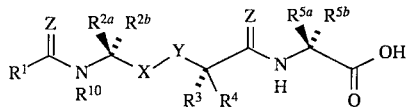

wherein:
$R^1$ is selected from:
  a) heterocycle selected from pyrrolidinyl, imidazolyl, pyridinyl, thiazolyl, pyridonyl, 2-oxopiperidinyl, indolyl, quinolinyl, and isoquinolinyl, and
  b) $C_1$–$C_{10}$ alkyl, which is substituted with a heterocycle and which is optionally substituted with one or more of $C_1$–$C_4$ alkyl, hydroxy or amino groups;
    wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
  a) a side chain of a naturally occurring amino acid, wherein the amino acid is selected from alanine, leucine, isoleucine and valine; and
  b) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl;

$R^{5a}$ is selected from:
  a) a side chain of a naturally occurring amino acid, wherein the amino acid is selected from methionine and glutamine,
  b) an oxidized form of a side chain of a naturally occurring amino acid which is:
    i) methionine sulfoxide, or
    ii) methionine sulfone, and
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl;;

$R^{5b}$ is selected from:
a) hydrogen, and
b) $C_1$–$C_3$ alkyl;

X-Y is
a)
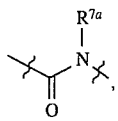

b)
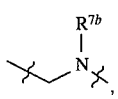

c)
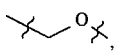

d)
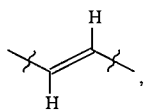

or
e) —$CH_2$—$CH_2$—;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

$R^{10}$ is independently selected from hydrogen and $C_1$–$C_6$ alkyl;

Z is independently $H_2$ or O;

m is 0, 1 or 2; and s is 4 or 5;

or the pharmaceutically acceptable salts thereof.

In a second more preferred embodiment of this invention, the prodrugs of the preferred compounds of formula I are illustrated by the formula II:

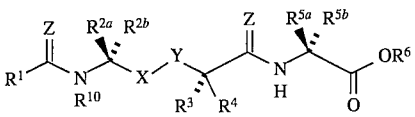

wherein:

$R^1$ is selected from:
a) heterocycle selected from pyrrolidinyl, imidazolyl, pyridinyl, thiazolyl, pyridonyl, 2-oxopiperidinyl, indolyl, quinolinyl, and isoquinolinyl, and
b) $C_1$–$C_{10}$ alkyl, which is substituted with a heterocycle and which is optionally substituted with one or more of $C_1$–$C_4$ alkyl, hydroxy or amino groups;
wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
a) a side chain of a naturally occurring amino acid, wherein the amino acid is selected from alanine, leucine, isoleucine and valine; and
b) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:

i) methionine sulfoxide, or
ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

$R^{5b}$ is selected from:
a) hydrogen, and
b) $C_1$–$C_3$ alkyl;

$R^6$ is
a) substituted or unsubstituted $C_1$–$C_8$ alkyl, wherein the substituent on the alkyl is selected from:
1) aryl,
2) heterocycle,
3) —$N(R^9)_2$,
4) —$OR^8$, or
b)

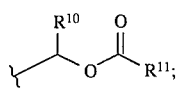

X-Y is
a)

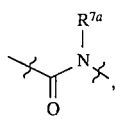

b)

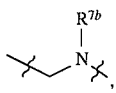

c)

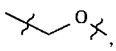

d)

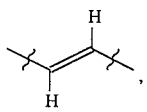

e) —$CH_2$—$CH_2$—;

$R^7a$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

$R^{10}$ is independently selected from hydrogen and $C_1$–$C_6$ alkyl;

$R^{11}$ is independently selected from $C_1$–$C_6$ alkyl;

Z is independently $H_2$ or O;

m is 0, 1 or 2; and s is 4 or 5;

or the pharmaceutically acceptable salts thereof.

In a third more preferred embodiment of this invention, the inhibitors of farnesyl transferase are illustrated by the formula III:

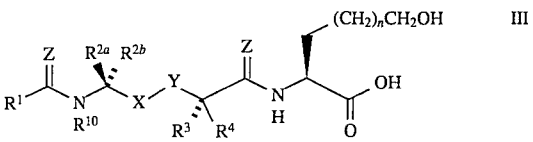

wherein:
$R^1$ is selected from:
a) heterocycle selected from pyrrolidinyl, imidazolyl, pyridinyl, thiazolyl, pyridonyl, 2-oxopiperidinyl, indolyl, quinolinyl, and isoquinolinyl, and
b) $C_1$–$C_{10}$ alkyl, which is substituted with a heterocycle and which is optionally substituted with one or more of $C_1$–$C_4$ alkyl, hydroxy or amino groups;
wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
a) a side chain of a naturally occurring amino acid,
wherein the amino acid is selected from alanine, leucine, isoleucine and valine; and
b) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl;

X-Y is a)
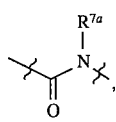

b)
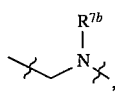

c)
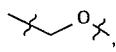

d)
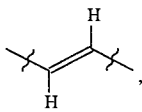

e) —$CH_2$—$CH_2$—;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1$–$C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

$R^{10}$ is independently selected from hydrogen and $C_1$–$C_6$ alkyl;

Z is independently $H_2$ or O;

m is 0, 1 or 2;

n is 0, 1 or 2; and s is 4 or 5;

or the pharmaceutically acceptable salts thereof.

In a fourth more preferred embodiment of this invention, the prodrugs of the preferred compounds of formula III are illustrated by the formula IV:

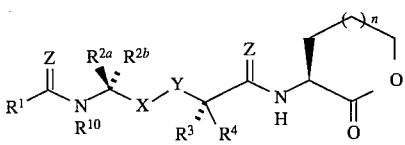

wherein:

$R^1$ is selected from:
  a) heterocycle selected from pyrrolidinyl, imidazolyl, pyridinyl, thiazolyl, pyridonyl, 2-oxopiperidinyl, indolyl, quinolinyl, and isoquinolinyl, and
  b) $C_1$–$C_{10}$ alkyl, which is substituted with a heterocycle and which is optionally substituted with one or more of $C_1$–$C_4$ alkyl, hydroxy or amino groups;
    wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
  a) a side chain of a naturally occurring amino acid,
    wherein the amino acid is selected from alanine, leucine, isoleucine and valine; and
  b) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, c) substituted or unsubstituted $C_1$-$C_{10}$ alkyl, $C_2$-$C_{10}$ alkenyl, $C_3$-$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$—, $C_1$-$C_{20}$ alkyl, and d) $C_1$-$C_6$ alkyl substituted with an unsubstituted or substituted group selected from aryl, heterocyclic and $C_3$-$C_{10}$ cycloalkyl;

X-Y is a)

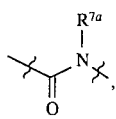

b)

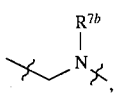

c)

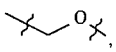

d)

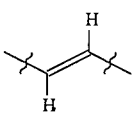

e) —$CH_2$—$CH_2$—;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$-$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$-$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$-$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$-$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$-$C_6$ alkyl and aryl;

$R^9$ is independently selected from $C_1$-$C_6$ alkyl and aryl;

$R^{10}$ is independently selected from hydrogen and $C_1$-$C_6$ alkyl;

Z is independently $H_2$ or O;

m is 0, 1 or 2;

n is 0, 1 or 2; and s is 4 or 5;

or the pharmaceutically acceptable salts thereof.

The preferred compounds of this invention are as follows:

Pyroglutamyl-valyl-phenylalanyl-methionine; (SEQ.ID.NO.: 1)
Pyroglutamyl-valyl-phenylalanyl-methionine methyl ester; (SEQ.ID.NO.: 1)
Pyroglutamyl-valyl-isoleucyl-methionine; (SEQ.ID.NO.: 2)
Pyroglutamyl-valyl-isoleucyl-methionine methyl ester; (SEQ.ID.NO.: 2)
Nicotinoyl-isoleucyl-phenylalanyl-methionine;
Nicotinoyl-isoleucyl-phenylalanyl-methionine methyl ester;
N-[2(S)-(L-Pyroglutamylamino)-3-methylbutyl]phenylalanyl-methionine;
N-[2(S)-(L-Pyroglutamylamino)-3-methylbutyl]phenylalanyl-methionine methyl ester;
N-[5(S)-(L-Pyroglutamylamino)-6(S)-methyl-2(R)-butyl-3,4(E)-octenoyl]-methionine;
N-[5(S)-(L-Pyroglutamylamino)-6(S)-methyl-2(R)-butyl-3,4(E)-octenoyl]-methionine methyl ester;
N-[5 (S)-((Imidazol-4-yl)acetylamino)-6(S)-methyl-2(R)-butyl-3,4(E)-octenoyl]-methionine;
N-[5(S)-((Imidazol-4-yl)acetylamino)-6(S)-methyl-2(R)-butyl-3,4(E)-octenoyl]-methionine methyl ester;
N-[5(S)-((Imidazol-4-ylcarbonylamino)-6(S)-methyl-2(R)-butyl-3,4(E)-octenoyl]-methionine;
N-[5(S)-((Imidazol-4-ylcarbonylamino)-6(S)-methyl-2(R)-butyl-3,4(E)-octenoyl]-methionine methyl ester;
N-[2(S)-(2(S)-(Imidazol-4-yl)acetylamino)-3(S)-methylpentyloxy)-3-phenylpropionyl]-methionine;
N-[2(S)-(2(S)-(Imidazol-4-yl)acetylamino)-3(S)-methylpentyloxy)-3-phenylpropionyl]-methionine methyl ester;
N-[2(S)-(2(S)-Pyroglutamylamino-3(S)-methylpentyloxy)-3-phenylpropionyl]-methionine;
N-[2(S)-(2(S)-Pyroglutamylamino-3(S)-methylpentyloxy)-3-phenylpropionyl]-methionine methyl ester;
N-[2(S)-(2(S)-Imidazol-4-ylcarbonyl)amino)-3(S)-methylpentyloxy)-3-phenylpropionyl]-methionine;
N-[2(S)-(2(S)-Imidazol-4-ylcarbonyl)amino)-3(S)-methylpentyloxy)-3-phenylpropionyl]-methionine methyl ester;
N-[2(S)-(2(S)-((3-Picolinyl)amino)-3(S)-methylpentyloxy)-3-phenylpropionyl]-methionine;
N-[2(S)-(2(S)-((3-Picolinyl)amino)-3(S)-methylpentyloxy)-3-phenylpropionyl]-methionine methyl ester;
N-[2(S)-(2(S)-((Histidyl)amino)-3(S)-methylpentyloxy)-3-phenylpropionyl]-methionine;
N-[2(S)-(2(S)-((Histidyl)amino)-3(S)-methylpentyloxy)-3-phenylpropionyl]-methionine methyl ester;
N-Benzyl-N-[2(S)-(Imidazol-4-ylcarbonyl)amino)-3(S)-methylpentyl]-glycyl-methionine;
N-Benzyl-N-[2(S)-((Imidazol-4-ylcarbonyl)amino)-3(S)-methylpentyl]-glycyl-methionine methyl ester;
N-Benzyl-N-[2(S)-((Imidazol-4-ylacetyl)amino)-3(S)-methylpentyl]-glycyl-methionine;

N-Benzyl-N-[2(S)-((Imidazol-4-ylacetyl)amino)-3(S)-methylpentyl]-glycyl-methionine methyl ester;
N-Benzyl-N-[2(S)-((Pyroglutamyl)amino)-3(S)-methylpentyl]-glycyl-methionine;
N-Benzyl-N-[2(S)-((Pyroglutamyl)amino)-3(S)-methylpentyl]-glycyl-methionine methyl ester;
N-(1-Naphthylmethyl)-N-[2(S)-((imidazol-4-ylcarbonyl)amino)-3(S)-methylpentyl]-glycyl-methionine;
N-(1-Naphthylmethyl)-N-[2(S)-((imidazol-4-ylcarbonyl)amino)-3(S)-methylpentyl]-glycyl-methionine methyl ester;
N-(1-Naphthylmethyl)-N-[2(S)-((imidazol-4-ylacetyl)amino)-3(S)-methylpentyl]-glycyl-methionine;
N-(1-Naphthylmethyl)-N-[2(S)-((imidazol-4-ylacetyl)amino)-3(S)-methylpentyl]-glycyl-methionine methyl ester;
N-(1-Naphthylmethyl)-N-[2(S)-((pyroglutamyl)amino)-3(S)-methylpentyl]-glycyl-methionine; and
N-(1-Naphthylmethyl)-N-[2(S)-((pyroglutamyl)amino)-3(S)-methylpentyl]-glycyl-methionine methyl ester;
N-[1-(Pyroglutamylamino)cyclopent-1-ylmethyl]-N-(1-naphthylmethyl)glycyl-methionine methyl ester
N-[1-(Pyroglutamylamino)-cyclopent-1-ylmethyl]-N-(1-naphthylmethyl)glycyl-methionine
N-(2(S)-L-Histidylamino-3(S)-methylpentyl)-N-(benzylmethyl)glycyl-methionine methyl ester
N-(2(S)-L-Histidylamino-3(S)-methylpentyl)-N-(benzylmethyl)glycyl-methionine
N-(2(S)-L-Histidylamino-3(S)-methylpentyl)-N-(1-naphthylmethyl)glycyl-methionine methyl ester
N-(2(S)-L-Histidylamino-3(S)-methylpentyl)-N-(1-naphthylmethyl)glycyl-methionine
2(S)-[2(S)-(L-Pyroglutamyl)amino-3(S)-methylpentyloxy]-3-methylbutanoyl-methionine methyl ester
2(S)-[2(S)-(L-Pyroglutamyl)amino-3(S)-methylpentyloxy]-3-methylbutanoyl-methionine
2(S)-[2(S)-(Imidazol-4-ylacetyl)amino-3(S)-methylpentyloxy]-3-methylbutanoyl-methionine methyl ester
2(S)-[2(S)-(Imidazol-4-ylacetyl)amino-3(S)-methylpentyloxy]-3-methylbutanoyl-methionine
N-(Benzyl)-N-[2(S)-(2-oxopyrrolidin-5(R,S)-ylmethyl)amino-3(S)-methylpentyl]-glycyl-methionine methyl ester
N-(Benzyl)-N-[2(S)-(2-oxopyrrolidin-5(R,S)-ylmethyl)amino-3(S)-methylpentyl]-glycyl-methionine
N-(Benzyl)-N-{2(S)-[((D,L)-2-thiazolyl)alanyl)amino]-3(S)-methylpentyl}-glycyl-methionine methyl ester
N-(Benzyl)-N-{2(S)-[((D,L)-2-thiazolyl)alanyl)amino]-3(S)-methylpentyl}-glycyl-methionine
N-(Benzyl)-N-[2(S)-(3-pyridylmethyl)amino-3(S)-methylpentyl]-glycyl-methionine methyl ester
N-(Benzyl)-N-[2(S)-(3-pyridylmethyl)amino-3(S)-methylpentyl]-glycyl-methionine
2(S)-[2(S)-(2-Oxopyrrolidin-5(S)-ylmethyl)amino-3(S)-methylpentyloxy]-3-phenylpropionyl-methionine methyl ester
2(S)-[2(S)-(2-Oxopyrrolidin-5(S)-ylmethyl)amino-3(S)-methylpentyloxy]-3-phenylpropionyl-methionine
2(S)-[2(S)-(L-Pyroglutamyl)amino-3(S)-methylpentyloxy]-3-(1-naphthyl)propionyl-methionine sulfone methyl ester
2(S)-[2(S)-(L-Pyroglutamyl)amino-3(S)-methylpentyloxy]-3-(1-naphthyl)propionyl-methionine sulfone
2(S)-[2(S)-(L-Pyroglutamyl)amino-3(S)-methylpentyloxy]-3-(2-naphthyl)propionyl-methionine sulfone methyl ester
2(S)-[2(S)-(L-Pyroglutamyl)amino-3(S)-methylpentyloxy]-3-(2-naphthyl)propionyl-methionine sulfone
2(S)-[2(S)-(Imidazol-4-ylacetyl)amino-3(S)-methylpentyloxy]-3-(1-naphthyl)propionyl-methionine sulfone methyl ester
2(S)-[2(S)-(Imidazol-4-ylacetyl)amino-3(S)-methylpentyloxy]-3-(1-naphthyl)propionyl-methionine sulfone
2(S)-[2(S)-(Imidazol-4-ylacetyl)amino-3(S)-methylpentyloxy]-3-(2-naphthyl)propionyl-methionine sulfone methyl ester
2(S)-[2(S)-(Imidazol-4-ylacetyl)amino-3(S)-methylpentyloxy]-3-(2-naphthyl)propionyl-methionine sulfone
N-[2(S)-(L-pyroglutamyl)amino-3(S)-methylpentyl]-N-(3-quinolylmethyl)glycyl-methionine methyl ester
N-[2(S)-(L-pyroglutamyl)amino-3(S)-methylpentyl]-N-(3-quinolylmethyl)glycyl-methionine
N-(Benzyl)-N-[2(S)-(tetrazol-1-ylacetyl)amino-3(S)-methylpentyl]-glycyl-methionine methyl ester
N-(Benzyl)-N-[2(S)-(tetrazol-1-ylacetyl)amino-3(S)-methylpentyl]-glycyl-methionine
N-(Benzyl)-N-[2(S)-nicotinoylamino-3(S)-methylpentyl]-glycyl-methionine methyl ester
N-(Benzyl)-N-[2(S)-nicotinoylamino-3(S)-methylpentyl]-glycyl-methionine
N-[2(S)-(L-Pyroglutamyl)amino-3(S)-methylpentyl]-N-(1-naphthylmethyl)glycyl-methionine sulfoxide methyl ester
N-[2(S)-(L-Pyroglutamyl)amino-3(S)-methylpentyl]-N-(1-naphthylmethyl)glycyl-methionine sulfoxide
2(S)-{2(S)-[2(S,R)-(Imidazol-4-yl)-2-aminoacetyl)amino]-3(S)-methylpentyloxy}-3-phenylpropionyl-methionine sulfone methyl ester
2(S)-{2(S)-[2(S,R)-(Imidazol-4-yl)-2-aminoacetyl)amino]-3(S)-methylpentyloxy}-3-phenylpropionyl-methionine sulfone
2(S)-{2(S)-[2(R,S)-(Imidazol-4-yl)-2-aminoacetyl)amino]-3(S)-methylpentyloxy}-3-phenylpropionyl-methionine sulfone methyl ester
2(S)-{2(S)-[2(R,S)-(Imidazol-4-yl)-2-aminoacetyl)amino]-3(S)-methylpentyloxy}-3-phenylpropionyl-methionine sulfone
N-{2(S)-[2(S,R)-(Imidazol-4-yl)-2-aminoacetyl]amino-3(S)-methylpentyl}-N-(1-naphthylmethyl)glycyl-methionine methyl ester
N-{2(S)-[2(S,R)-(Imidazol-4-yl)-2-aminoacetyl]amino-3(S)-methylpentyl}-N-(1-naphthylmethyl)glycyl-methionine
N-{2(S)-[2(R,S)-(Imidazol-4-yl)-2-aminoacetyl]amino-3(S)-methylpentyl}-N-(1-naphthylmethyl)glycyl-methionine methyl ester
N-{2(S)-[2(R,S)-(Imidazol-4-yl)-2-aminoacetyl]amino-3(S)-methylpentyl}-N-(1-naphthylmethyl)glycyl-methionine
N-{2(S)-[(Imidazol-4-yl)methyl]amino-3(S)-methylpentyl}-N-(1-naphthylmethyl)glycyl-methionine methyl ester
N-{2(S)-[(Imidazol-4-yl)methyl]amino-3(S)-methylpentyl}-N-(1-naphthylmethyl)glycyl-methionine
N-[2(S)-(L-pyroglutamyl)amino-3(S)-methylpentyl]-N-(1-naphthylmethyl)glycyl-methionine isopropyl ester
N-[2(S)-(L-pyroglutamyl)amino-3(S)-methylpentyl]-N-(1-naphthylmethyl)glycyl-methionine t-butyl ester
N-[2(S)-(L-pyroglutamyl)amino-3(S)-methylpentyl]-N-(4-quinolylmethyl)glycyl-methionine methyl ester
N-[2(S)-(L-pyroglutamyl)amino-3(S)-methylpentyl]-N-(4-quinolylmethyl)glycyl-methionine
N-{2(S)-[3-(Imidazol-4-yl)propyl]amino-3(S)-methylpentyl}-N-(1-naphthylmethyl)glycyl-methionine methyl ester
N-{2(S)-[3-(Imidazol-4-yl)propyl]amino-3(S)-methylpentyl}-N-(1-naphthylmethyl)glycyl-methionine
N-[2(S)-(L-pyroglutamyl)amino-3(S)-methylpentyl]-N-(1-naphthylmethyl)glycyl-norleucine N-[2(S)-(L-pyroglutamyl)amino-3(S)-methylpentyl]-N-(1-naphthylmethyl)glycyl-norleucine methyl ester N-[2(S)-(L-pyroglutamyl)amino-3(S)-methylpentyl]-N-(1-naphthylmethyl)glycyl-glutamine N-[2(S)-(L-pyroglutamyl)amino-3(S)-methylpentyl]-N-(1-naphthylmethyl)glycyl-glutamine t-butyl ester N-[2(S)-(L-pyroglutamyl)amino-3(S)-methylpentyl]-N-[5-(dimethylamino)naphthylsulfonyl]glycyl-methionine methyl ester N-[2(S)-(3-pyridylmethyl)amino-3(S)-methylpentyl]-N-(1-naphthylmethyl)glycyl-methionine 2(S)-{2(S)-[2-(Imidazol-4-yl)ethyl]amino-3(S)-methylpentyloxy}-3-phenylpropionyl-methionine sulfone methyl ester 2(S)-{2(S)-[2-(Imidazol-4-yl)ethyl]amino-3(S)-methylpentyloxy}-3-phenylpropionyl-methionine sulfone N-[2(S)-(L-pyroglutamyl)amino-3(S)-methylpentyl]-N-(1-naphthylmethyl)glycyl-serine methyl ester N-[2(S)-(L-pyroglutamyl)amino-3(S)-methylpentyl]-N-(1-naphthylmethyl)glycyl-(D,L)-serine N-[2(S)-(L-pyroglutamyl)amino-3(S)-methylpentyl]-N-(1-naphthylmethyl)glycyl-(L,D)-serine N-[2(S)-(L-pyroglutamyl)amino-3(S)-methylpentyl]-N-(1-naphthylmethyl)glycyl-homoserine lactone N-[2(S)-(L-pyroglutamyl)amino-3(S)-methylpentyl]-N-(1-naphthylmethyl)glycyl-homoserine N-[2(S)-(L-pyroglutamyl)amino-3(S)-methylpentyl]-N-(cinnamyl)glycyl-methionine methyl ester N-[2(S)-(L-pyroglutamyl)amino-3(S)-methylpentyl]-N-(cinnamyl)glycyl-methionine N-{2(S)-[2-(Imidazol-4-yl)ethyl]amino-3(S)-methylpentyl}-N-(1-naphthylmethyl)glycyl-methionine methyl ester N-{2(S)-[2-(Imidazol-4-yl)ethyl]amino-3(S)-methylpentyl}-N-(1-naphthylmethyl)glycyl-methionine N-[2(S)-(L-pyroglutamyl)amino-3(S)-methylpentyl]-N-(1-naphthylmethyl)glycyl-alanine methyl ester N-[2(S)-(L-pyroglutamyl)amino-3(S)-methylpentyl]-N-(1-naphthylmethyl)glycyl-alanine N-[2(S)-(D-pyroglutamyl)amino-3(S)-methylpentyl]-N-(1-naphthylmethyl)glycyl-methionine methyl ester N-[2(S)-(D-pyroglutamyl)amino-3(S)-methylpentyl]-N-(1-naphthylmethyl)glycyl-methionine 2(S)-[2(S)-(L-Pyroglutamyl)amino-3(S)-methylpentyloxy]-3-phenylpropionyl-methionine sulfone methyl ester 2(S)-[2(S)-(L-Pyroglutamyl)amino-3(S)-methylpentyloxy]-3-phenylpropionyl-methionine sulfone N-[2(S)-(L-pyroglutamyl)amino-3(S)-methylpentyl]-N-(2,3-methylenedioxybenzyl)glycyl-methionine methyl ester N-[2(S)-(L-pyroglutamyl)amino-3(S)-methylpentyl]-N-(2,3-methylenedioxybenzyl)glycyl-methionine N-[2(S)-(Imidazol-4-ylacetyl)amino-3(S)-methylpentyl]-N-(2,3-dihydrobenzofuran-7-ylmethyl)glycyl-methionine methyl ester N-[2(S)-(Imidazol-4-ylacetyl)amino-3(S)-methylpentyl]-N-(2,3-dihydrobenzofuran-7-ylmethyl)glycyl-methionine N-{2(S)-[3-(3-indolyl)propionyl]amino-3(S)-methylpentyl}-N-(1-naphthylmethyl)glycyl-methionine methyl ester N-{2(S)-[3-(3-indolyl)propionyl]amino-3(S)-methylpentyl}-N-(1-naphthylmethyl)glycyl-methionine N-{2(S)-[3-(1-indolyl)propionyl]amino-3(S)-methylpentyl}-N-(1-naphthylmethyl)glycyl-methionine methyl ester N-{2(S)-[3-(1-indolyl)propionyl]amino-3(S)-methylpentyl}-N-(1-naphthylmethyl)glycyl-methionine N-[2(S)-(L-pyroglutamyl)amino-3(S)-methylpentyl]-N-(1-naphthylmethyl)glycyl-histidine methyl ester N-[2(S)-(L-pyroglutamyl)amino-3(S)-methylpentyl]-N-(1-naphthylmethyl)glycyl-histidine N-[2(S)-(L-pyroglutamyl)amino-3(S)-methylpentyl]-N-(cyclopropylmethyl)glycyl-methionine methyl ester N-[2(S)-(L-pyroglutamyl)amino-3(S)-methylpentyl]-N-(cyclopropylmethyl)glycyl-methionine N-[2(S)-(Imidazol-4-ylacetyl)amino-3(S)-methylpentyl]-N-(cyclopropylmethyl)glycyl-methionine methyl ester N-[2(S)-(Imidazol-4-ylacetyl)amino-3(S)-methylpentyl]-N-(cyclopropylmethyl)glycyl-methionine N-[2(S)-(L-pyroglutamyl)amino-3(S)-methylpentyl]-N-(2,3-dihydrobenzofuran-7-ylmethyl)glycyl-methionine methyl ester N-[2(S)-(L-pyroglutamyl)amino-3(S)-methylpentyl]-N-(2,3-dihydrobenzofuran-7-ylmethyl)glycyl-methionine 2(S)-[2(S)-N-(L-Pyroglutamyl)-N-methylamino-3(S)-methylpentyloxy]-3-phenylpropionyl-methionine methyl ester 2(S)-[2(S)-N-(L-Pyroglutamyl)-N-methylamino-3(S)-methylpentyloxy]-3-phenylpropionyl-methionine N-[2(S)-(L-pyroglutamyl)amino-3(S)-methylpentyl]-N-(1-naphthylmethyl)glycyl-O-methylserine methyl ester N-[2(S)-(L-pyroglutamyl)amino-3(S)-methylpentyl]-N-(1-naphthylmethyl)glycyl-O-methylserine N-(1-Naphthylmethyl)-N-[2(S)-(N'-(L-pyroglutamyl)-N'-methylamino)-3(S)-methylpentyl]-glycyl-methionine methyl ester N-(1-Naphthylmethyl)-N-[2(S)-(N'-(L-pyroglutamyl)-N'-methylamino)-3(S)-methylpentyl]-glycyl-methionine N-[1-(Pyroglutamylamino)cyclopent-1-ylmethyl]-N-(1-naphthylmethyl)glycyl-methionine methyl ester N-[1-(Pyroglutamylamino)-cyclopent-1-ylmethyl]-N-(1-naphthylmethyl)glycyl-methionine N-[2(S)-(Pyridin-2-on-6-ylcarbonyl)amino-3(S)-methylpentyl]-N-(1-naphthylmethyl)glycyl-methionine methyl ester N-[2(S)-(Pyridin-2-on-6-ylcarbonyl)amino-3(S)-methylpentyl]-N-(1-naphthylmethyl)glycyl-methionine N-[2(S)-(L-pyroglutamyl)amino-3(S)-methylpentyl]-N-(3-chlorobenzyl)glycyl-methionine methyl ester N-[2(S)-(L-pyroglutamyl)amino-3(S)-methylpentyl]-N-(3-chlorobenzyl)glycyl-methionine N-[2(S)-(L-pyroglutamyl)amino-3(S)-methylpentyl]-N-(1-naphthylmethyl)glycyl-O-methylhomoserine methyl ester N-[2(S)-(L-pyroglutamyl)amino-3(S)-methylpentyl]-N-(1-naphthylmethyl)glycyl-O-methylhomoserine N-[2(S)-(L-pyroglutamyl)amino-3(S)-methylpentyl]-N-(2,3-dimethyl-benzyl)glycyl-methionine methyl ester N-[2(S)-(L-pyroglutamyl)amino-3(S)-methylpentyl]-N-(2,3-dimethyl)benzyl)glycyl-methionine N-[2(S)-(L-pyroglutamyl)amino-3(S)-methylpentyl]-N-(1-naphthylmethyl)glycyl-(2-thienyl)alanine methyl ester N-[2(S)-(L-pyroglutamyl)amino-3(S)-methylpentyl]-N-(1-naphthylmethyl)glycyl-(2-thienyl)alanine or the pharmaceutically acceptable salts thereof.

The most preferred compounds of the invention are:

N-(1-Naphthylmethyl)-N-[2(S)-((pyroglutamyl)amino-3(S)-methylpentyl]-glycyl-methionine

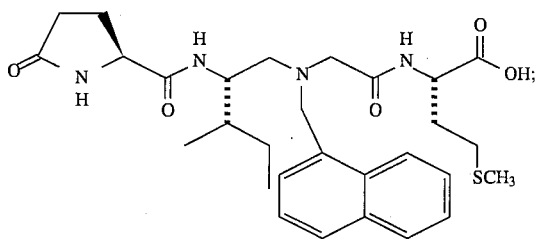

N-(1-Naphthylmethyl)-N-[2(S)-((pyroglutamyl)amino-3(S)-methylpentyl]-glycyl-methionine methyl ester

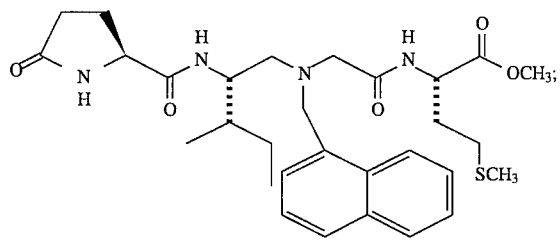

N-(1-Naphthylmethyl)-N-[2(S)-((pyroglutamyl)amino-3(S)-methylpentyl]-glycyl-methionine isopropyl ester

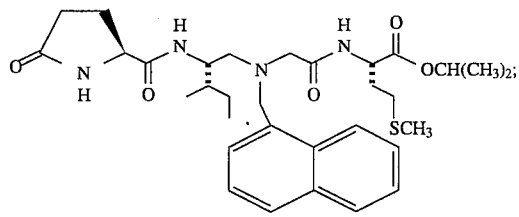

N-(1-Naphthylmethyl)-N-[2(S)-((pyroglutamyl)amino-3(S)-methylpentyl]-glycyl-methionine t-butyl ester

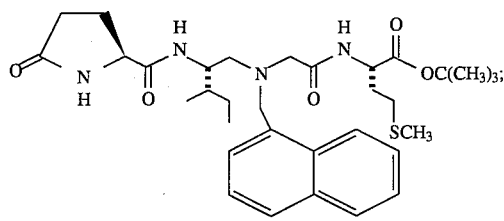

N-(1-Naphthylmethyl)-N-[2(S)-((imidazol-4-ylacetyl)amino)-3(S)-methylpentyl]-glycyl-methionine

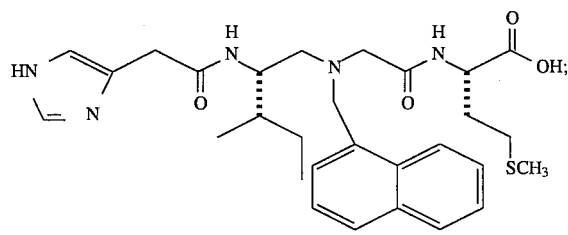

N-(1-Naphthylmethyl)-N-[2(S)-((imidazol-4-ylacetyl)amino)-3(S)-methylpentyl]-glycyl-methionine methyl ester

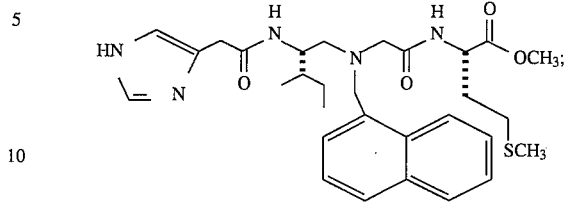

or the pharmaceutically acceptable salts thereof.

In the present invention, the amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11-15 membered tricyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O—$, $—OH$, $(C_1-C_6 \text{ alkyl})S(O)_m—$, $(C_1-C_6 \text{ alkyl})C(O)NH—$, $H_2N—C(NH)—$, $(C_1-C_6 \text{ alkyl})C(O)—$, $(C_1-C_6 \text{ alkyl})OC(O)—$, $N_3$, $(C_1-C_6 \text{ alkyl})O-C(O)NH—$ and $C_1-C_{20}$ alkyl.

When $R^{2a}$ and $R^{2b}$ and $R^3$ and $R^4$ are combined to form $—(CH_2)_s—$, cyclic moieties are formed. Examples of such cyclic moieties include, but are not limited to:

When $R^{5a}$ and $R^{5b}$ are combined to form 13 $(CH_2)_s—$, cyclic moieties as described hereinabove for $R^{2a}$ and $R^{2b}$ and $R^3$ and $R^4$ are formed. In addition, such cyclic moieties may optionally include a heteroatom(s). Examples of such heteroatom-containing cyclic moieties include, but are not limited to:

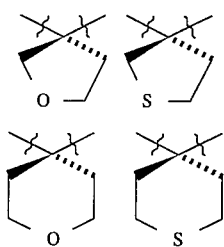

-continued

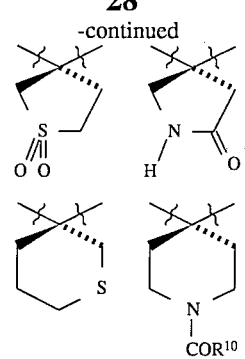

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

It is intended that the definition of any substituent or variable (e.g., $R^8$, Z, m, etc.) at a particular location in a molecule be independent of its definitions elsewhere in that molecule. Thus, $—N(R^8)_2$ represents $—NHH$, $—NHCH_3$, $—NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The compounds of the invention can be synthesized from their constituent amino acids by conventional peptide synthesis techniques, and the additional methods described below. Standard methods of peptide synthesis are disclosed, for example, in the following works: Schroeder et al., "*The Peptides*", Vol. I, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "*The Peptides: Analysis, Synthesis, Biology*" 2, Chapter 1, Academic Press, 1980, or Stewart et al., "*Solid Phase Peptide Synthesis*", Second Edition, Pierce Chemical Company, 1984. The teachings of these works are hereby incorporated by reference.

Abbreviations used in the description of the chemistry and in the Examples that follow are:

$Ac_2O$ Acetic anhydride;
Boc t-Butoxycarbonyl;
DBU 1,8-diazabicyclo [5.4.0]undec-7-ene;
DMAP 4-Dimethylaminopyridine;
DME 1,2-Dimethoxyethane;
DMF Dimethylformamide;
$EDC_1$-(3-dimethylaminopropyl)-3-ethyl-carbodiimide hydrochloride;

HOBT 1-Hydroxybenzotriazole hydrate;
Et₃N Triethylamine;
EtOAc Ethyl acetate.
FAB Fast atom bombardment;
HOOBT 3-Hydroxy-1,2,2-benzotriazin-4(3H)-one;
HPLC High-performance liquid chromatography;
MCPBA m-Chloroperoxybenzoic acid;
MsCl Methanesulfonyl chloride;
NaHMDS Sodium bis(trimethylsilyl)amide
Py Pyridine;
TFA Trifluoroacetic acid;
THF Tetrahydrofuran;

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A. Amide bond formation and protecting group cleavage using standard solution or solid phase methodologies.

Reaction B. Preparation of a reduced peptide subunit by reductive alkylation of an amine by an aldehyde using sodium cyanoborohydride or other reducing agents.

Reaction C. Alkylation of a reduced peptide subunit with an alkyl or aralkyl halide or, alternatively, reductive alkylation of a reduced peptide subunit with an aldehyde using sodium cyanoborohydride or other reducing agents.

Reaction D. Peptide bond formation and protecting group cleavage using standard solution or solid phase methodologies.

Reaction E. Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes.

REACTION SCHEME A
Reaction A. Coupling of residues to form an amide bond

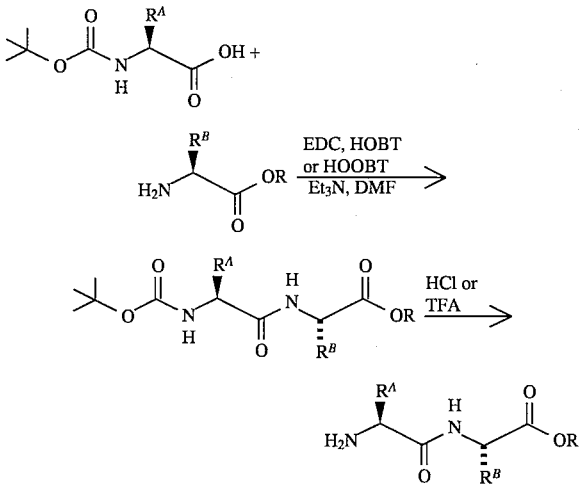

REACTION SCHEME B
Reaction B. Preparation of reduced peptide subunits by reductive alkylation

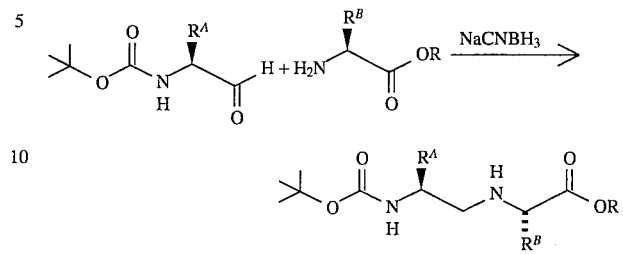

REACTION SCHEME C
Reaction C. Alkylation/reductive alkylation of reduced peptide subunits

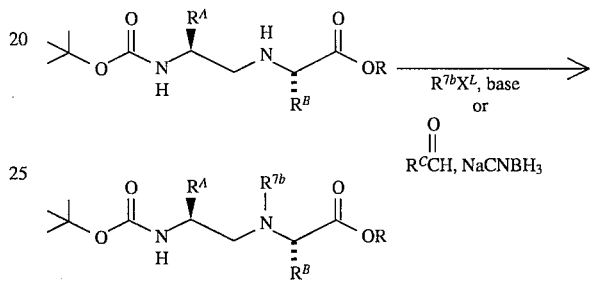

REACTION SCHEME D
Reaction D. Coupling of residues to form an amide bond

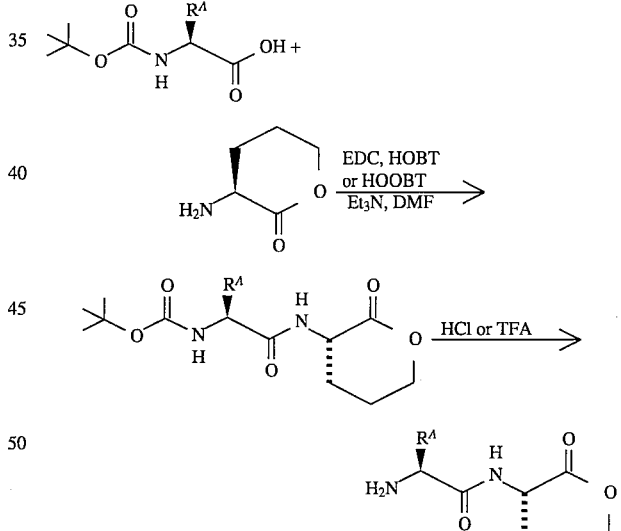

REACTION SCHEME E
Reaction E. Preparation of reduced dipeptides from peptides

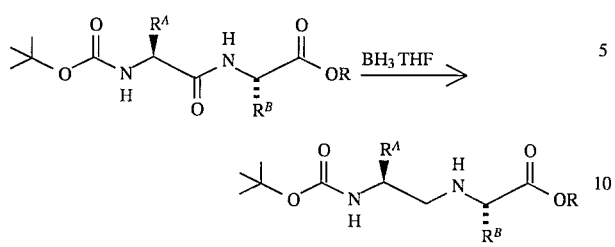

where $R^A$ and $R^B$ are $R^{2a}$, $R^{2b}$, $R^3$, $R^4$ $R^{5a}$ and $R^{5b}$ as previously defined; $X^L$ is a leaving group, e.g., $Br^-$, $I^-$ or $MsO-$; and $R^C$ is defined such that $R^{7b}$ is generated by the reductive alkylation process.

Certain compounds of this invention wherein X-Y is an ethenylene or ethylene unit are prepared by employing the reaction sequences shown in Reaction Schemes F and G. Reaction Scheme F outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme F, Step B, Part 1), and stereospecific boron trifluoride or zinc chloride activated organo-magnesio, organo-lithio, or organo-zinc copper(1) cyanide $S_N2'$ displacement reaction (Scheme F, Step G). Through the use of optically pure N-Boc amino acids as starting material and these two key reactions, the stereo-chemistry of the final products is well defined. In Step H of Scheme F, $R^1$ is incorporated using coupling reaction A and $R^1COOH$; the alkylation reaction C using $R^1CHO$ and a reducing agent; or alkylation reaction C using $R^1CH_2X^L$.

The alkane analogs are prepared in a similar manner by including an additional catalytic hydrogenation step as outlined in Reaction Scheme G.

REACTION SCHEME F

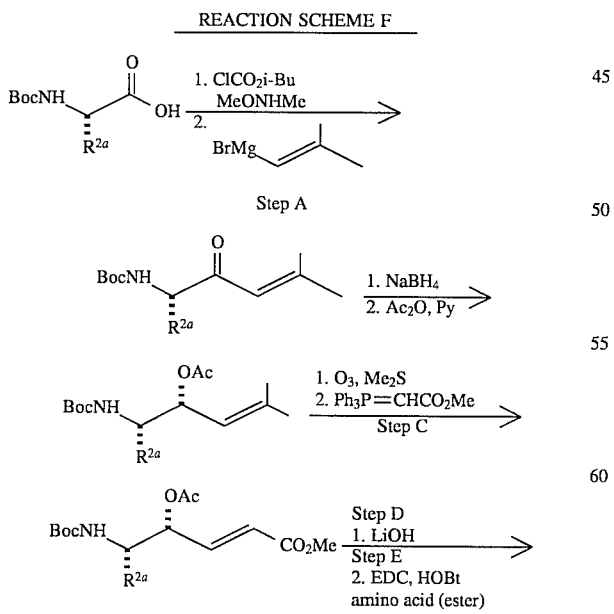

-continued
REACTION SCHEME F

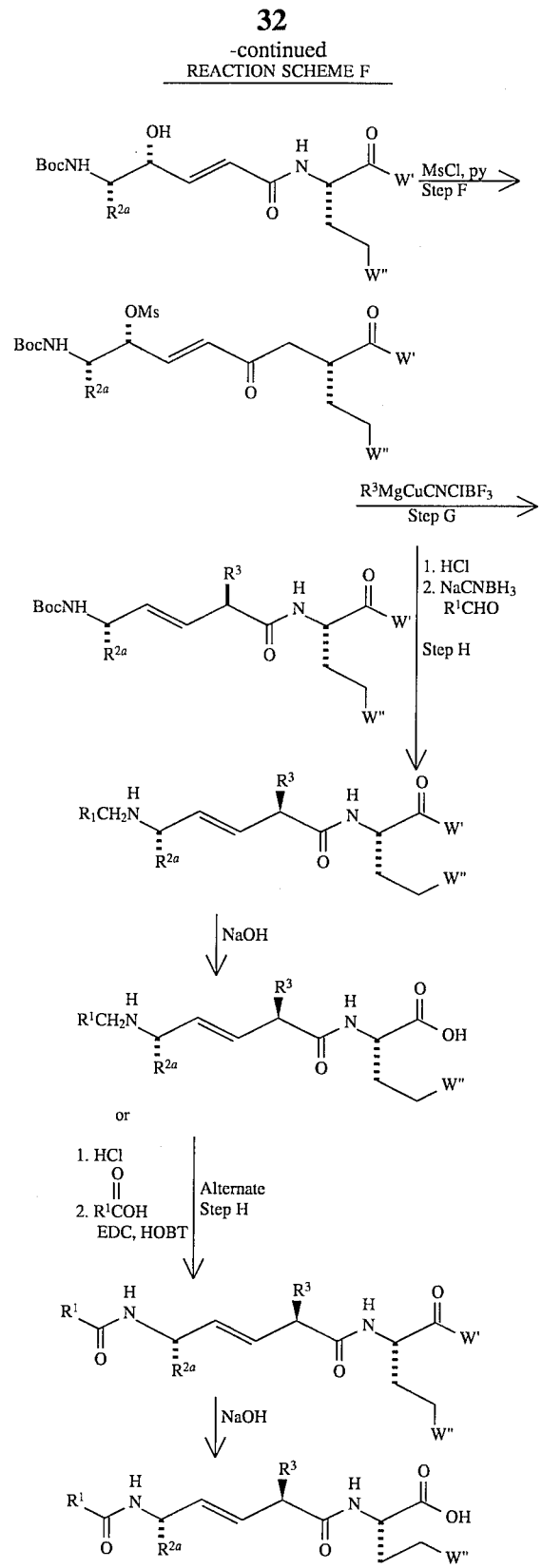

REACTION SCHEME G

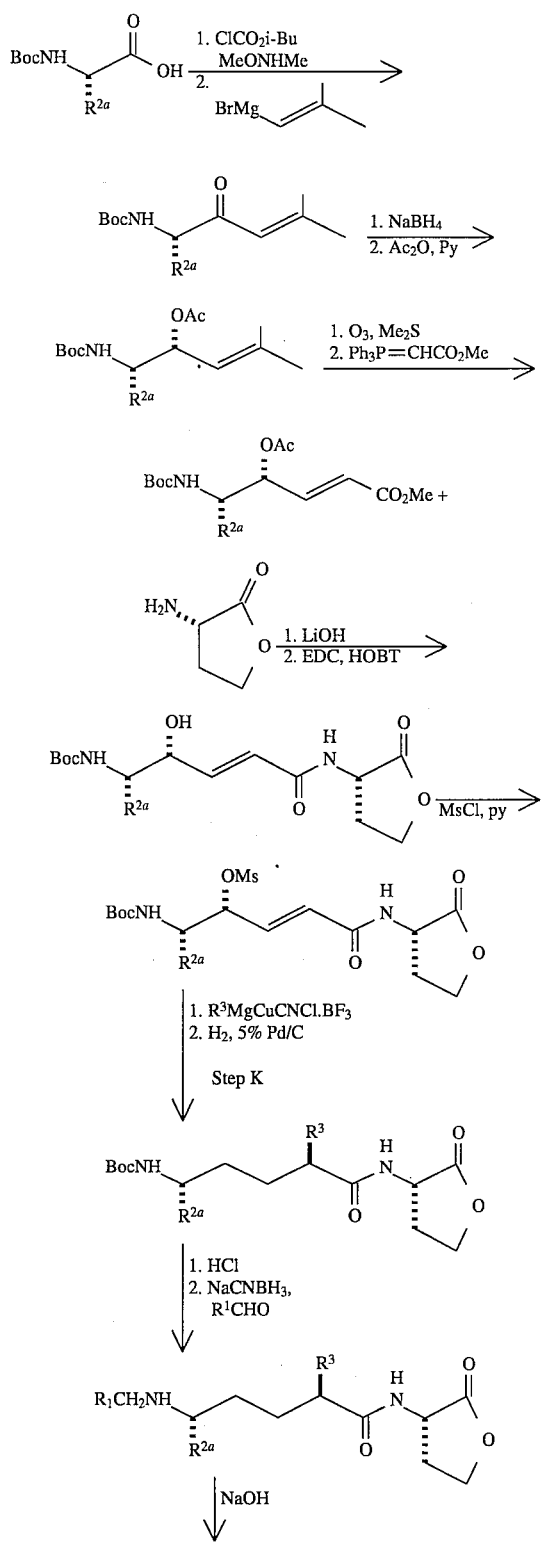

-continued
REACTION SCHEME G

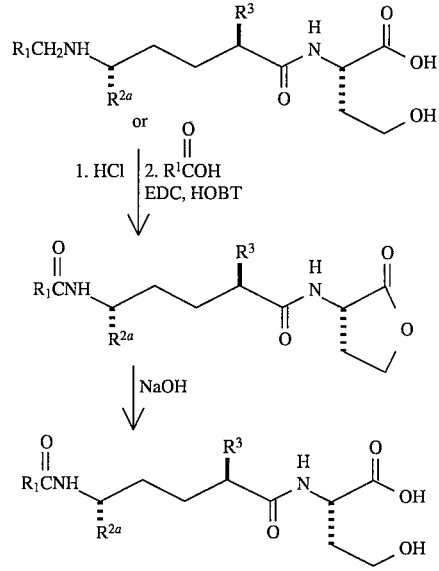

The oxa isostere compounds of this invention are prepared according to the route outlined in Scheme H. An aminoalcohol 1 is acylated with alpha-chloroacetyl chloride in the presence of trialkylamines to yield amide 2. Subsequent reaction of 2 with a deprotonation reagent (e.g., sodium hydride or potassium t-butoxide) in an ethereal solvent such as THF provides morpholinone 3. The N-Boc derivative 4 is then obtained by the treatment of 3 with BOC anhydride and DMAP (4-dimethylaminopyridine) in methylene chloride. Alkylation of 4 with $R^3X^L$, where $X^L$ is a leaving group such as Br⁻, I⁻ or Cl⁻ in THF/DME (1,2-dimethoxyethane) in the presence of a suitable base, preferably NaHMDS [sodium bis(trimethylsilyl)amide], affords 5, which is retreated with NaHMDS followed by either protonation or the addition of an alkyl halide $R^4X$ to give 6a or 6b, respectively. Alternatively, 6a can be prepared from 4 via an aldol condensation approach. Namely, deprotonation of 4 with NaHMDS followed by the addition of a carbonyl compound $R^xR^yCO$ gives the adduct 7 (wherein $R^x$ and Ry are selected so that $R^3$ is eventually formed). Dehydration of 7 can be effected by mesylation and subsequent elimination catalyzed by DBU (1,8-diazabicyclo[5.4.0]undec-7-ene) or the direct treatment of 7 with phosphorus oxychloride in pyridine to give olefin 8. Then, catalytic hydrogenation of 8 yields 6a. Direct hydrolysis of 6 with lithium hydrogen peroxide in aqueous THF will produce acid 9b. Sometimes, it is more efficient to carry out this conversion via a 2-step sequence, namely, hydrolysis of 6 in hydrochloric acid to afford 9a, which is then derivatized with BOC-ON or BOC anhydride to give 9b. The peptide coupling of acid 9b with either an alpha-aminolactone (e.g., homoserine lactone, etc.) or the ester of an amino acid is carried out under the conditions exemplified in the previously described references to yield derivative 10. Treatment of 10 with gaseous hydrogen chloride gives 11, which undergoes reductive alkylation in the presence of an aldehyde $R^1CHO$ (12) and a reducing agent (e.g., sodium cyanoborohydride); or acylation in the presence of R¹COOH (13) and a peptide coupling reagent affording the products 14a and b. Hydrolysis of compounds 14 to the corresponding hydroxy acids and acids, respectively, is accomplished by standard methods such as treatment with NaOH in alcoholic or aqueous milieux followed by careful acidification with dilute HCl.

The thia, oxothia and dioxothia isostere compounds of this invention are prepared in accordance to the route depicted in Scheme I. Aminoalcohol 1 is derivatized with $BOC_2O$ to give 15. Mesylation of 15 followed by reaction with methyl alpha-mercaptoacetate in the presence of cesium carbonate gives sulfide 16. Removal of the BOC group in 16 with TFA followed by neutralization with

SCHEME H

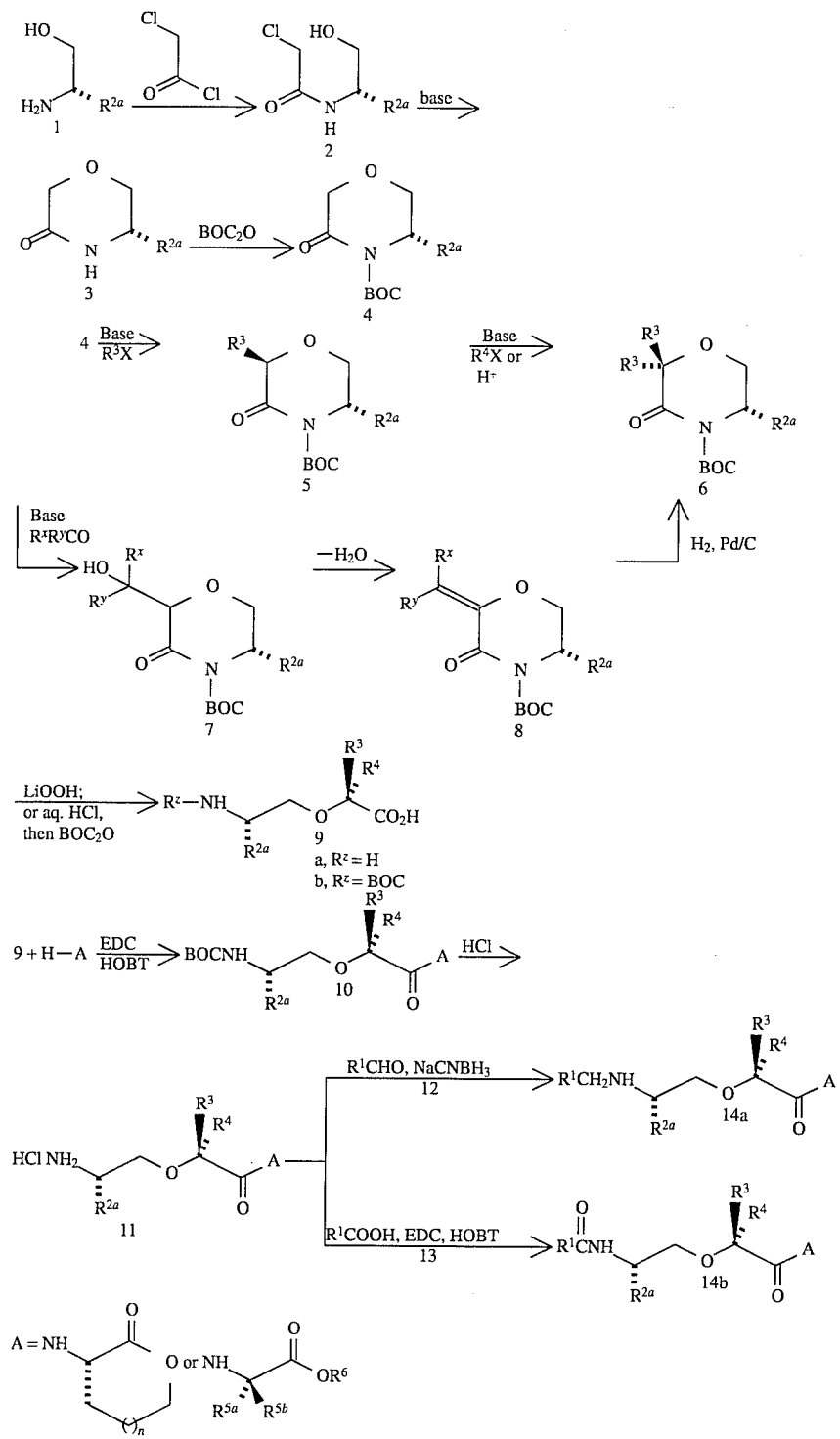

di-isopropylethylamine leads to lactam 17. N-BOC derivative 18 is obtained via the reaction of 17 with BOC anhydride in THF catalyzed by DMAP. Sequential alkylation of 18 with the alkyl halides $R^3X$ and $R^4X$ in THF/DME using NaHDMS as the deprotonation reagent produces 19. Hydrolysis of 19 in hydrochloride to yield 20a, which is derivatized with Boc anhydride to yield 20b. The coupling of 20b with an alpha-aminolactone (e.g., homoserine lactone, etc.) or the ester of an amino acid is carried out under conventional conditions as exemplified in the previously described references to afford 21. Sulfide 21 is readily oxidized to sulfone 22 by the use of MCPBA (m-chloroperoxybenzoic acid). The N-BOC group of either 21 or 22 is readily removed by treatment with gaseous hydrogen chloride. The resultant amine hydrochloride 23 undergoes reductive alkylation in the presence of an aldehyde $R^1CHO$ (12) and a reducing agent (e.g., sodium cyanoborohydride); or acylation in the presence of $R^1COOH$ (13) and a peptide coupling reagent to afford the products 24 and 25.

SCHEME I

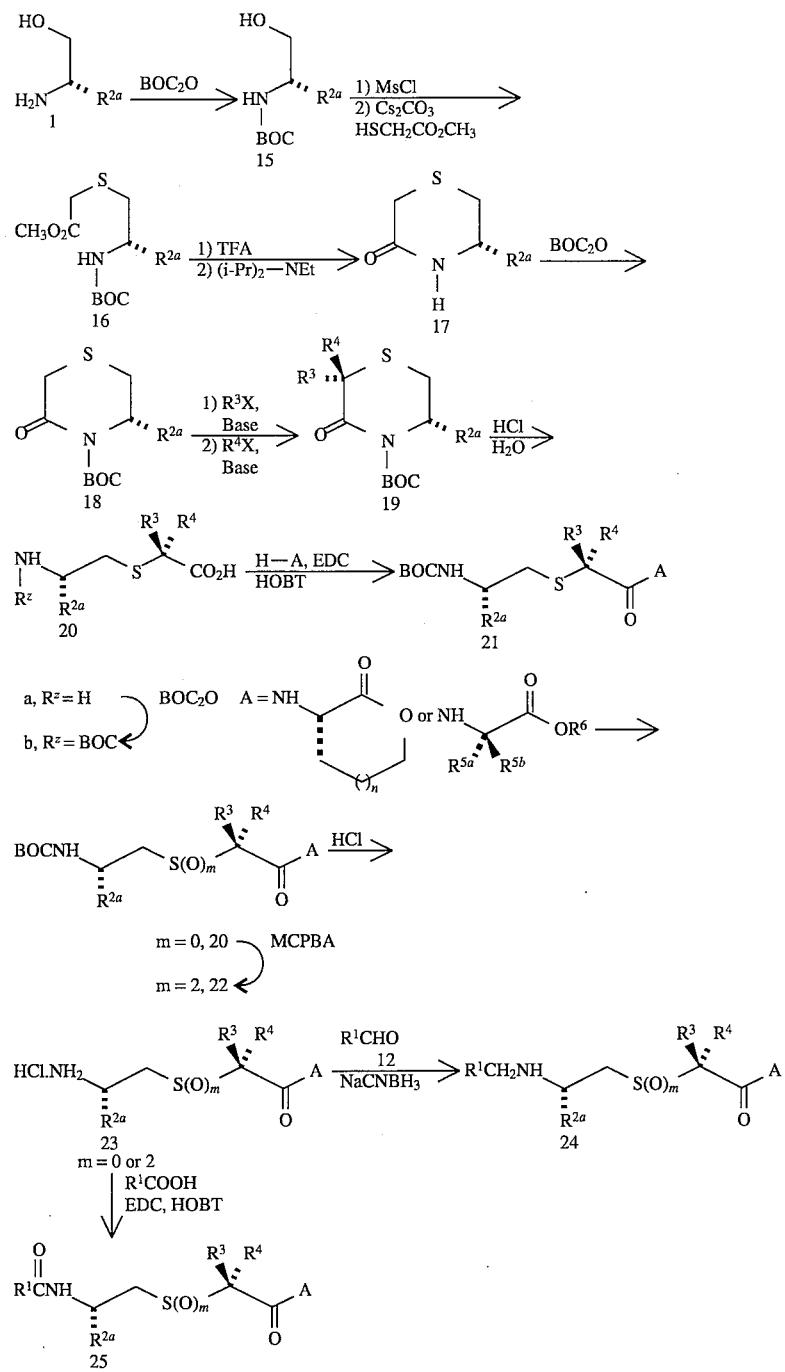

The compounds of this invention inhibit Ras farnesyl transferase which catalyzes the first step in the post-translational processing of Ras and the biosynthesis of functional Ras protein. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

EXAMPLE 1

Preparation of pyroglutamyl-valyl-phenyalanyl-methionine

The title compound was assembled using standard solid phase synthetic methods on an automated peptide synthesizer. The product was cleaved from the resin with HF and purified by reverse-phase HPLC. The title compound was obtained as a lyophilized powder and characterized by amino acid analysis (found: 1.73 μmol/mg) and FAB mass spectrum, m/z=507 (M+1).

EXAMPLE 2

Preparation of pyroglutamyl-valyl-isoleucyl-methionine

This compound was prepared using the method of Example 1. Amino acid analysis. Found 1.65 μmol/mg. FAB mass spectrum, m/z=473 (M+1).

EXAMPLE 3

Preparation of nicotinyl-valyl-phenylalanyl-methionine

Standard solution phase peptide synthesis methods were employed to prepare the title compound.

Anal. Calcd for $C_{26}H_{34}N_4O_5S.1.75H_2O$: C, 57.17; H, 6.92; N, 10.26. Found: C, 57.11; H, 6.63; N, 10.35.

EXAMPLE 4

Preparation of N-[2(S)-(L-Pyroglutamylamino)-3-methylbutyl]-phenylalanyl-methionine Step A: Preparation of N-(3-methyl-2(S)-(t-butoxycarbonylamino)-but-1-yl)phenylalanine methyl ester Sodium cyanoborohydride (2.0 g, 0.03 mole) was added portionwise (one hour) to a solution of the known compound 2(S)-t-butoxycarbonylamino-3-methylbutyraldehyde (5.8 g, 0.029 mole) and phenylalanine methyl ester hydrochloride (6.1 g, 0.028 mole) in methanol (150 ml) and acetic acid (1.5 ml). The clear reaction mixture was stirred at room temperature under argon for 2 hours and concentrated in vacuo. The residue was cooled in an ice bath, neutralized with saturated $NaHCO_3$ and extracted (3×) with ethyl acetate. The organic phase was dried ($Na_2SO_4$), filtered and evaporated to give a pale yellow residue, which was purified by column chromatography on silica gel using 20% ethyl acetate-hexane. The title compound (8.4 g) was obtained as a pale yellow oil.

Step B: Preparation of N-(3-methyl-2(S)-(t-butoxycarbonylamino)but-1-yl)phenylalanine A solution of lithium hydroxide (1.63 g, 0.068 mole) in water (70 ml) was added to a solution of the product of Step A (7.6 g, 0.021 mole) in ethylene glycol dimethyl ether (100 ml) with cooling in an ice bath. The reaction mixture was stirred at room temperature under Ar for 2 hours, concentrated in vacuo, and extracted (2×) with ethyl acetate. The aqueous phase was neutralized with 10% of citric acid, cooled and filtered to give the product as a white solid (6.6 g), mp >193° (dec).

Step C: Preparation of N-(3-methyl-2(S)-(t-butoxycarbonylamino)but-1-yl)phenylalanylmethionine-methyl ester N-Methyl morpholine (4.0 ml) and 1-ethyl-3-(3-dimethylaminopropyl) carbodimide (EDC) hydrochloride (0.96 g, 0.005 mole) were added to a solution of the product of Step B (1.76 g, 0.005 mole), methionine methyl ester hydrochloride (1.0 g, 0.005 mole) and 1-hydroxybenzotriazole hydrate (HOBT,0.677 g, 0.005 mole) in dimethylformamide (DMF, 30 ml) the reaction mixture was stirred at room temperature over the weekend, concentrated in vacuo and taken up in ice, water, and ethyl acetate. After addition of 10% aqueous citric acid, the ethyl acetate solution was separated, washed with water (2×), aqueous $NaHCO_3$ and brine, and dried over sodium sulfate. Filtration and evaporation of the ethyl acetate solution gave a pale yellow residue, which was purified by column chromatography (silica gel) using 35% ethyl acetate-hexane. The title compound (1.97 g) was obtained as a white solid.

Step D: Preparation of N-(3-methyl-2(S)-aminobut-1-yl)phenylalanyl-methionine methyl ester hydrochloride The product of Step C (0.74 g, 0.0015 mole) in ethyl acetate (25 ml) was treated with HCl gas at −25° C. for 30 min. The solution was stirred at room temperature for 1 hour and concentrated in vacuo to provide the title compound as a white solid (~0.79 g).

Step E: Preparation of N-[2(S)-(L-Pyroglutamylamino)-3-methylbutyl]phenylalanyl-methionine methyl ester N-methylmorpholine (1.0 mL) and EDC hydrochloride (0.252 g, 1.3 mmol) were added to a solution of L-pyroglutamic acid (0.17 g, 1.3 mmol), the product of Step D (0.60 g, 1.3 mmol), and HOBT (1.18 g, 1.3 mmol) in 10 mL of DMF. The reaction mixture was stirred at room temperature for 27 h, concentrated in vacuo and the product was isolated as the free base following a standard workup.

Chromatography on silica gel (6% isopropanol in methylene chloride) gave the pure title compound (0.36 g) as an oil.

Step F: Preparation of N-[2(S)-(L-Pyroglutamylamino)-3-methylbutyl]phenylalanyl-methionine The product of Step E was dissolved in 15 mL of methanol and a solution of 60 mg of LiOH in 7 mL of water added. The mixture was stirred for 3 h at room temperature under argon, diluted with water and filtered. The filtrate was neutralized with 10% citric acid and cooled. The product was isolated by filtration and further purified by reverse phase HPLC. Lyophilization gave the title compound as a white solid. $^1$H-NMR ($D_2O$) δ7.40 (3H, m), 7.29 (2H, m), 4.36 (1H, dd, J=4.9, 8.5 Hz), 4.29 (1H, m), 4.22 (1H, dd, J=6.2, 8.7 Hz), 3.96 (1H, dd, J=7, 13 Hz), 3.33 (1H, dd, J=6.4, 14.3 Hz), 3.20 (3H, m), 2.54 (1H, m), 2.44 (2H, m), 2.39 (1H, m), 2.32 (1H, m), 2.09 (2H, m), 2.06 (3H, s), 1.92 (1H, m), 1.87 (1H, m), 0.92 (3H, d, J=7.8 Hz), 0.90 (3H, d, J=7.8 Hz).

Anal. Calcd for $C_{24}H_{36}N_4O_5S.1.4$ TFA: C, 49.35; H, 5.78; N, 8.59. Found: C, 49.23; H, 5.79; N, 8.64.

EXAMPLE 5

Preparation of N-[5(S)-(L-Pyroglutamylamino)-6(S)-methyl-2(R)-butyl-3,4(E)-octenoyl]-methionine methyl ester Step A: Preparation of 4(S)-N-tert-(butyloxy)carbonylamino-3(S),7-dimethyl-6,7-octen-5-one To a cold (0° C.) solution of N-t-(butoxy)carbonyl-L-isoleucine hemihydrate (6.01 g, 25 mmol) in ethyl acetate (90 mL), N-methyl morpholine (2.75 mL, 25 mmol) and isobutyl chloroformate (3.25 mL, 25.1 mmol) were added successively. The resultant white suspension was stirred at 0° C. for 15 minutes treated with N,O-dimethylhydroxylamine hydrochloride (2.52 g, 25.8 mmol) and N-methylmorpholine (2.75 mL, 25 mmol), and then stirred at room temperature overnight. The resultant mixture was washed successively with water, 10% aqueous citric acid, brine, and was dried over anhydrous magnesium sulfate, filtered and concentrated. The residual oil was chromatographed on silica gel eluting with 30% ethyl acetate in hexane. Collection and concentration of appropriate fractions provided 5.0 g (73%) of the corresponding amide.

A 1 liter three neck round bottom flask was charged with magnesium turnings (44 g, 1.8 mol) and flamed dried under a steady stream of dry argon. The turnings were activated by stirring under an atmosphere of argon for an additional 3 to 4 hours at room temperature. Tetrahydrofuran (450 mL), freshly distilled from sodium benzophenone ketyl, 2-methylpropenyl bromide (50 g, 0.37 mol), and a crystal of iodine were added. The mixture was warmed gently with a mantle until slight reflux occurred. Without removing the mantle heating was discontinued, and the mixture was stirred overnight under an atmosphere of argon. The resultant Grignard reagent was used as described in the following.

To a cold (−50° C.) solution of N-tert-(butyloxy)carbonylisoleucine N,O-dimethylhydroxylamide (17.2 g, 63 mmol) in tetrahydrofuran (400 mL), the above Grignard reagent in tetrahydrofuran (prepared from 50 g of 2-methylpropenyl bromide) was added over a period of 20 min., with the temperature of the reacting solution maintained below −40° C. The mixture was then allowed to warm up slowly to room temperature. The resultant solution was diluted with diethyl ether, treated with 10% aqueous citric acid, washed with brine, dried over magnesium sulfate, filtered, and concentrated under vacuo. The residual oil was chromatographed on silica gel eluting with 7% ethyl acetate in hexane. Collection and concentration of appropriate fractions provided 12.6 g (74%) of the ketone.

Step B: Preparation of 4(S)-N-tert-(butyloxy)carbonylamino-5(R)-acetoxy-3(S),7-dimetbyl-6,7-octene To a cold (0° C.) solution of 4(S)-N-tert-(butyloxy)-carbonylamino-3(S),7-dimethyl-6,7-octen-5-one (12.57 g, 46.7 mmol) in methanol (200 mL), sodium borohydride was added portionwise until reaction was complete as monitored by TLC on silica gel eluting with 20% ethyl acetate in hexane. The resultant mixture was concentrated under vacuo. The residue was suspended in diethyl ether, washed successively with 1M aqueous hydrochloric acid and brine, dried over magnesium sulfate, filtered and concentrated under vacuo to provide the corresponding alcohol (11.93 g).

Without further purification, the crude alcohol, 4-N,N-dimethylaminopyridine (0.132 g), and pyridine (17 mL) were dissolved in dichloromethane (48 mL), cooled to 0° C. and treated with acetic anhydride (18.8 mL, 199 mmol). The resultant mixture was stirred at room temp for 2 hours and concentrated under vacuo. The residual oil was chromatographed on silica gel eluting with 20% ethyl acetate in hexane. Collection and concentration of appropriate fractions provided 10.7 g (73%) of the acetate as a white solid.

Step C: Preparation of methyl 5(S)-N-tert-(butyloxy)carbonylamino-4(R)-acetoxy-6(S)-methyl-2,3-E-octenoate To a cold (−78° C.) solution of 4(S)-N-tert-(butyloxy)-carbonylamino-5(R)-acetoxy-3(S),7-dimethyl-6,7-octene (6.5 g, 20.7 mmol) in dichloromethane (100 mL), a steady stream of ozone was bubbled through until a blue color persisted. The mixture was stirred for an additional 5 rain and purged with argon to remove excess ozone. Then dimethyl sulfide (15 mL) was added and the reaction mixture was allowed to warm to room temperature. The resultant mixture was cooled back to −78° C., and (carbomethoxymethylene)-triphenylphosphorane (15.3 g, 45.7 mmol) was added. The mixture was stirred at room temp overnight and concentrated onto silica gel (20 g). The resultant solid was loaded on a column of silica gel and the product was eluted with 15% EtOAc in hexane. Collection and concentration of appropriate fractions provided 6.5 (91%) of the octenoate.

Step D: Preparation of 5(S)-N-tert-(butyloxy)carbonylamino-4(R)-hydroxy-6(S)-methyl-2,3-E-octenoic acid To a solution of methyl 5(S)-N-tert-(butyloxy)-carbonylamino-4(R)-acetoxy-6(S)-methyl-2,3-E-octenoate (1 g, 2.9 mmol) in tetrahydrofuran (2 mL), a solution of lithium hydroxide (0.5 g, 12 mmol) in methanol-water (3:1 v/v) was added. The mixture was made homogenous by addition of a minimum amount of a methanol-water (3:1 v/v) and stirred at room temp for 2 days. The resultant solution was acidified with aqueous hydrochloric acid to pH 5 and concentrated under vacuo. The residue was subjected to column chromatography on silica gel eluting with 20% methanol in chloroform. Collection and concentration of appropriate fractions provided 0.71 g (87%) of the corresponding hydroxyacid.

Step E: Preparation of 5(S)-N-tert-(butyloxy)carbonylamino-4(R)-hydroxy-6(S)-methyl-2,3-E-octenoyl methionine methyl ester To a solution of 5(S)-N-tert-(butyloxy)carbonylamino-4(R)-hydroxy-6(S)-methyl-2,3-E-octenoyl acid (1.91 g, 6.65 mmol) in dimethyl-formamide (28 mL), 1-(3-dimethylaminopropyl)-3-ethylcarbodiimide hydrochloride (1.91 g, 9.98 mmol), 1-hydroxybenzo-triazole hydrate (1.35 g, 9.98 mmol), L-methionine methyl ester hydrochloride (3.98, 19.95 mmol), and diisopropylethylamine (2.41 mL, 18.62 mmol) were added. The resultant mixture was stirred at room temperature overnight, and concentrated under vacuo. The is residue was diluted with ethyl acetate, and the organic solution washed successively with water, 10% aqueous citric acid, brine, dried over magnesium sulfate, filtered and concentrated. The residue was then subjected to column chromatography on silica gel eluting with 80% ethyl acetate in hexane. Collection and concentration of appropriate fractions provided 1.0 g (35%) of the coupled product.

Step F: Preparation of 5(S)-N-tert-(butyloxy)carbonylamino-4(R)-(methylsulfonyl)oxy-6(S)-methyl-2,3-E-octenoyl methionine methyl ester To a cold (−20° C.) solution of 5(S)-N-tert-(butyloxy)-carbonylamino-4(R)-hydroxy-6(S)-methyl-2,3-E-octenoyl methionine methyl ester (0.80 g, 1.85 mmol) in a mixture of dichloromethane (12 mL) and pyridine (6 mL), methanesulfonyl chloride (0.8 mL) was added. The resultant mixture was kept at 0° C. overnight, and concentrated under vacuo. The residue was diluted with dichloromethane, washed successively with sat. sodium bicarbonate, and brine. The organic phase was dried over magnesium sulfate, filtered and concentrated. The residue was subjected to column chromatography on silica gel eluting with a mixture of ethyl acetate and hexane, 8:2 v/v. Collection and concentration of appropriate fractions provided 0.67 g (71%) of the mesylate, which is stable for storage at −10° C.

Step G: Preparation of 5(S)-N-tert-(butyloxy)carbonylamino-6(S)-methyl-2(R)-n-butyl-3,4-E-octenoyl-methionine methyl ester To a cold (−78° C.) suspension of copper(I) cyanide (0.17 g, 1.9 mmol) in tetrahydrofuran (25 mL, freshly distilled from sodium benzophenone ketyl), a solution of n-butylmagnesium chloride (1 mL, 2.0M, 1.9 mmol) in tetrahydrofuran was added. The mixture was stirred at 0° C. until a homogeneous solution was formed. Once a solution was formed, it was cooled to −78° C., boron-trifluoride etherate (0.24 mL, 1.9 mmol) was added, and the resulting mixture was stirred at −78° C. for 5 min. A solution of 5(S)-N-tert-(butyloxy)carbonylamino-4(R)-(methylsulfonyl)oxy-6(S)-methyl-2,3-E-octenoyl methionine methyl ester (0.24 g, 0.48 mmol) in tetrahydrofuran (25 mL) was added dropwise to the above mixture. The resultant solution was stirred at −78° C. for 3h, quenched with sat. aqueous ammonium chloride (pH 8) and diluted with diethyl ether. The organic solution was washed with brine, dried over magnesium sulfate, filtered, and concentrated. The residue was chromatographed on silica gel eluting with 60% ethyl acetate in hexane. Collection and concentration of appropriate fractions provided 0.18 g (80%) of the 3,4-E-octenoyl-methionine methyl ester.

Step H: 5(S)-amino-6(S)-methyl-2(R)-n-butyl-3,4-E-octenoyl-methionine methyl ester hydrochloride To a cold (0° C.) solution of 5(S)-N-tert-(butyloxy)carbonylamino-6(S)-methyl-2(R)-n-butyl-3,4-E-octenoyl-methionine methyl ester (0.18 g, 0.38 mmol) in a mixture of ethyl acetate (20 mL) and dichloromethane (20 mL), a steady stream of anhydrous hydrogen chloride gas was bubbled through for a period of 10 min. The mixture was capped and stirred for an additional 40 min at 0° C. The resultant solution was than purged with a stream of argon and concentrated under vacuum to provide the corresponding hydrochloride salt.

Step I: Preparation of N-[5(S)-(L-Pyroglutamylamino)-6(S)-methyl-2(R)-butyl3,4(E)-octenoyl]-methionine methyl ester The product of Step H was coupled to pyroglutamic acid under standard conditions.

Anal. Calcd for $C_{24}H_{40}N_3O_4S.0.3$ TFA.0.2 $H_2O$: C, 58.57; H, 8.13; N, 8.33. Found: C, 58.50; H, 8.09; N, 8.20.

EXAMPLE 6

Preparation of
N-[5(S)-(L-Pyroglutamylamino)-6(S)-methyl-2(R)-butyl-3,4 (E)-octenoyl]-methionine The methyl ester of the product of Example 5 was saponified as described for Example 3, Step B.

EXAMPLE 7

Preparation of
N-[5(S)-((Imidazol-4-yl)acetylamino)-6(S)-methyl-2(R)-butyl-3,4(E)-octenoyl]-methionine and
N-[5(S)-((Imidazol-4-yl)acetylamino)-6(S)-methyl-2(R)-butyl-3,4(E)-octenoyl]-methionine methyl ester Using the methods of Examples 5 and 6, substituting imidazole-4-acetic for pyroglutamic acid, the title compounds were obtained. The compound was characterized as the ester, and the corresponding acid was generated by in situ hydrolysis.

Anal. Calcd for $C_{24}H_{40}N_4O_4S.1.3$ TFA: C, 50.80; H, 6.62; N, 8.91. Found: C, 50.65; H, 6.57; N, 8.74.

EXAMPLE 8

Preparation of
N-[5(S)-(Imidazol-4-ylcarbonylamino)-6(S)-methyl-2(R)-butyl-3,4(E)-octenoyl]-methionine and
N-[5(S)-(Imidazol-4-ylcarbonylamino)-6(S)-methyl-2(R)-butyl-3,4(E)-octenoyl]-methionine methyl ester Using the methods of Examples 5 and 6, substituting imidazole-4-carboxylic acid for pyroglutamic acid, the title compounds were obtained. The compound was characterized as the ester and the carboxylic acid was prepared by in situ hydrolysis.

Anal. Calcd for $C_{23}H_{38}N_4O_4S.1$ TFA: C, 51.12; H, 6.66; N. 9.46. Found: C, 50.84; H, 6.74; N, 9.65.

EXAMPLE 9

Preparation of
N-[2(S)-(2(S)-(Imidazol-4-yl)acetylamino)-3(S)-methylpentyloxy)-3-phenylpropionyl]-methionine methyl ester Step A: Preparation of N-(alpha-chloroacetyl)-L-isoleucinol To a stirred solution of L-isoleucinol (20 g, 0.17 mol) and triethylamine (28.56 ml, 0.204 mol) in $CH_2Cl_2$ (500 ml) at −78° C. was added chloroacetyl chloride (16.3 ml, 0.204 mol) over 5 minutes. The cooling bath was removed and the solution allowed to warm to −20° C. The mixture was diluted with EtOAc and washed sequentially with 1M HCl, and brine and dried ($Na_2SO_4$). Evaporation in vacuo afforded the amide title compound (35 g, 100%).

Rf=0.3 $CH_2Cl_2$: MeOH (95:5);

$^1$H NMR (CDCl$_3$) δ6.80 (1H, brd, J=5 Hz), 4.10 (2H, s), 3.84 (1H, m), 3.79 (2H, m), 2.65 (1H, brs), 1.72 (1H, m), 1.55 (1H, m), 1.17 (1H, m), 0.96 (3H, d, J=6 Hz) 0.90 (3H,t, J=6 Hz).

Step B: Preparation of 5(S)-[1(S)-methyl]propyl-2,3,5,6-tetrahydro-4H-1,4-oxazin-3-one To a stirred solution of N-(a-chloroacetyl)-L-isoleucinol (7.4 g, 0.038 mol) in THF (125 ml) under argon at 0° C. was slowly added sodium hydride (2.2 g of a 60% dispersion in mineral oil, 0.055 mol) with concomitant gas evolution. After completing the addition, the mixture was warmed to room temperature (R.T.) and stirred for 16 hr. Water (2.8 ml) was added and the solvents evaporated in vacuo. The residue was dissolved in CHCl$_3$ (70 ml) and washed with water and saturated NaCl solution. The organic layer was dried (Na$_2$SO$_4$) and evaporated in vacuo. The residue was chromatographed using silica gel eluting with CH$_2$Cl$_2$:MeOH (96:4) to afford the lactam title compound (4.35 g, 72%) as a white solid.

Rf=0.35 CH$_2$Cl$_2$:MeOH (95:5);

$^1$H NMR δ(CDCl$_3$) 6.72 (1H, brs), 4.20 (1H, d, J=14.5 Hz), 4.10 (1H, d, J=14.5 Hz), 3.88 (1H, dd, J=9 and 3.5 Hz), 3.58 (1H, dd, J=9 and 6.5 Hz), 3.45 (1H, brqt, J=3.5 Hz), 1.70–1.45 (2H, m), 1.34–1.15 (1H, m), 0.96 (3H, t, J=6.5 Hz), 0.94 (3H, d, J=6.5 Hz).

Step C: Preparation of N-(tert-butoxycarbonyl)-5(S)-[1(S)-methyl]propyl-2,3,5,6-tetrahydro-4H-1,4-oxazin-3-one 5(S)-[1(S)-Methyl]propyl-2,3,5,6-tetrahydro-4H-1,4-oxazin-3-one (12.2 g, 0.0776 mol) and DMAP (18.9 g, 0.155 mol) were dissolved in methylene chloride (120 ml) under argon at R.T. Boc anhydride (33.9 g, 0.155 mol) was added to the stirred solution in one portion, with concomitant gas evolution and the mixture was stirred at R.T. for 16 hr. The solvent was evaporated in vacuo and the residue was taken up in ethyl acetate and washed sequentially with 10% citric acid, 50% NaHCO$_3$ and finally brine. The organic extract was dried (Na$_2$SO$_4$) and evaporated in vacuo. Chromatography of the residue over silica gel eluting with 20% EtOAc in hexanes afforded the title compound (14.1 g, 71%) as a white solid.

Rf=0.75 EtOAc:hexanes (20:80); mp 59°–60° C.

Anal. Calcd for C$_{13}$H$_{23}$O$_4$N C, 60.68; H, 9.01; N, 5.44 Found: C, 60.75; H, 9.01; N, 5.58

$^1$H NMR (CDCl$_3$) δ4.25 (1H, d, J=15 Hz), 4.15 (1H, d, J=15 Hz), 4.15–4.00 (2H, m), 3.73 (1H, dd, J=10 and 2 Hz), 1.88 (1H, qt, J=6 Hz), 1.55 (9H, s), 1.50–1.36 (1H, m), 1.35–1.19 (1H, m) 1.00 (3H, d, J=6 Hz) 0.95 (3H, d, J=6.5 Hz).

Step D: Preparation of N-(tert-Butoxycarbonyl)-2(S)-benzyl-5(S)-[1(S)-methyl]propyl-2,3,5,6-tetrahydro-4H-1,4-oxazin-3-one A solution of N-(tert-butoxycarbonyl)-5(S)-[1(S)-methyl]propyl-2,3,5,6-tetrahydro-4H-1,4-oxazin-3-one (5.75 g, 22.3 mmol) in DME (100 ml) under argon was cooled to −60° C. The cold solution was transferred via canula to a second flask containing sodium bis(trimethylsilyl)amide (24.6 ml of a 1M solution in THF, 24.6 mmol) at −78° C. under argon. After stirring for 10 minutes, benzyl bromide (2.25 ml, 19 mmol) was added over 5 minutes and the resulting mixture was stirred at −78° C. for 3 hours. After this time, the reaction mixture was transferred via cannula to another flask containing sodium bis(trimethylsilyl)amide (24.6 ml of a 1M solution in THF, 24.6 mmol) at −78° C., under argon. After stirring for a further 5 minutes, the reaction was quenched by the addition of saturated aqueous ammonium chloride solution (24.6 ml) and allowed to warm to room temperature. This mixture was diluted with brine (50 ml) and water (20 ml) and then extracted with ethyl acetate (2×100 ml). The organic extracts were washed with brine (50 ml) and evaporated in vacuo to afford an oil. Chromatography of the residue over silica gel (230–400 mesh, 300 g) eluting with 10–20% ethyl acetate in hexanes afforded the title compound (5.12 g, 67%) as a clear oil.

Rf=0.25 EtOAc:Hexanes (20:80);

$^1$H NMR (CDCl$_3$) δ7.35–7.15 (5H, m), 4.31 (1H, dd, J=6 and 2 Hz), 4.03 (1H, d, J=12 Hz), 3.88 (1H, dd, J=6 and 1 Hz), 3.66 (1H, dd, J=12 and 2 Hz), 3.29 (1H, dd, J=12 and 3 Hz), 1.54 (9H, s), 3.12 (1H, dd, J=12 and 7 Hz), 1.47 (1H, m), 1.25 (1H, m), 1.10 (1H, m), 0.83 (3H, d, J=6 Hz), 0.80 (3H, t, J=6 Hz).

Step E: Preparation of N-(tert-butoxycarbonyl)-2(S)-[2(S)-amino-3(S)-methyl]pentyloxy-3-phenylpropionic acid To a stirred solution of N-(tert-butoxycarbonyl)-2(S)-benzyl-5(S)-[1(S)-methyl]propyl-2,3,5,6-tetrahydro-4H-1,4-oxazin-3-one (5.1 g, 14.7 mmol) in THF (150 ml) and water (50 ml) at 0° C. was added hydrogen peroxide (15 ml of a 30% aqueous solution, 132 mmol) and lithium hydroxide (3.0 g, 63.9 mmol). After stirring for 30 minutes, the reaction was quenched with a solution of sodium sulfite (28.25 g, 0.224 mol) in water (70 ml). The THF was evaporated in vacuo and the aqueous phase was acidified to pH 3–4 by addition of 10% citric acid solution and extracted with EtOAc. The organic extracts were dried (Na$_2$SO$_4$), evaporated in vacuo and the residue purified by chromatography over silica gel eluting with 4% MeOH in CH$_2$Cl$_2$ to give the lactam 2(S)-benzyl-5(S)-[1(S)-methyl]propyl-2,3,5,6-tetrahydro-4H-1,4-oxazin-3-one (0.82 g 22%) and then with 20% MeOH in CH$_2$Cl$_2$ to afford the title compound (4.03 g, 75%) as a viscous oil.

Rf=0.4 MeOH:CH$_2$Cl$_2$ (5:95)+0.3% AcOH;

$^1$H NMR (d6 DMSO) δ7.35–7.10 (5H, m), 6.68 (1H, br, s), 3.75 (1H, dd, J=7.5 and 2.5 Hz) 3.54 (1H, m), 3.5–3.2 (2H, m) 2.99 (1H, dd, J=12.5 and 2.5 Hz), 2.75 (1H, dd, J=12.5 and 7.5 Hz), 1.50–1.35 (11H, m), 0.98 (1H, sept, J=6 Hz), 0.78 (3H, t, J=6 Hz), 0.65 (3H, d, J=6 Hz);

FAB MS 366 (MH$^+$) 266 (MH$_2^+$-CO$_2$tBu).

Step F: Preparation of N-(tert-Butoxycarbonyl)-2(S)-[2(S)-amino-3(S)-methyl]-pentyloxy-3-phenylpropionyl-methionine methyl ester To a stirred solution of N-(tert-butoxycarbonyl)-2(S)-[2(S)-amino-3(S)-methyl]-pentyloxy-3-phenylpropionic acid (0.200 g, 0.53 mmol) and EDC (0.158 g, 0.82 mmol) in DMF (15 ml) at room temperature was added HOBT (0.89 mg 0.66 mmol) and methionine methyl ester hydrochloride (0.131 g, 0.66 mmol). The pH was adjusted to pH=6.5 by addition of NEt$_3$ (0.18 mL) (the pH was monitored by application of an aliquot of the reaction mixture to a moist strip of pH paper). After stirring at room temperature for 16 hr, the reaction was diluted with EtOAc and washed with saturated NaHCO$_3$ and then brine and dried (NaSO$_4$). Evaporation in vacuo (sufficient to remove DMF) and chromatography over silica gel eluting with EtOAc/hexane (25%–50%) afforded the title compound (240 mg). NMR (CD$_3$OD) δ0.78 (3H, d, J=6 Hz), 0.89 (3H, t, J=6 Hz), 1.11 (H, m), 1.47 (9H, s), 2.06 (3H, s), 2.2–2.4 (2H, m), 2.90 (H, d of d, J=14, 7 Hz), 3.05 (H, d of d, J=14, 5 Hz), 3.38 (H, d of d, J=8, 6 Hz), 3.5–3.55 (2H, m), 3.71 (3H, s), 3.97 (H, d of d, J=7, 5 Hz), 6.60 (H, d, J=10 Hz), 7.24 (5H, m).

Step G: Preparation of 2(S)-[2(S)-Amino-3(S)-methyl]-pentyloxy-3-phenylpropionyl-methionine methyl ester hydrochloride Anhydrous HCl gas was bubbled through a cold (0° C.) solution of N-(tert-butoxycarbonyl)-2(S)-[2(S)-amino-3(S)-methyl]-pentyloxy-3-phenylpropionyl-methionine methyl ester (240 mg, 0.47 mmol) in ethyl acetate (25 ml) until a saturated solution was obtained. The resulting mixture was stirred at 0° C. for 1 hr. The solution was purged with nitrogen and the mixture concentrated in vacuo to afford the title compound as a sticky foam (210 mg, 100%) which was used without further purification. NMR (CD$_3$OD) δ0.84 (3H, d, J=6 Hz), 0.93 (3H, t, J=6 Hz), 1.20 (H, m), 1.40 (H, m), 1.60 (H, m), 2.08 (3H, s), 2.3–2.5 (2H, m), 2.98 (H, d of d, J=14, 7 Hz), 3.11 (H, d of d, J=14, 5 Hz), 3.23 (H, m), 3.57 (H, d of d, J=10, 6 Hz), 3.70 (H, d, J=3 Hz), 3.73 (3H, s), 4.12 (H, d of d, J=8, 6 Hz), 7.30 (5H, m).

Step H: Preparation of N-[2(S)-(2(S)-(Imidazol-4-yl)acetylamino)-3(S)-methylpentyloxy)-3-phenylpropionyl]-methionine methyl ester Using standard peptide coupling reagents, imidazole-4-acetic acid was coupled to the product of Step G.

Anal Calcd for C$_{26}$H$_{38}$N$_4$O$_5$S.0.75 H$_2$O: C, 58.67; H, 7.48; N, 10.53. Found: C, 58.38; H, 7.18; N, 10.56.

EXAMPLE 10

Preparation of N-[2(S)-(2(S)-(Imidazol-4-yl)acetylamino)-3(S)-methylpentyloxy)-3-phenylpropionyl]-methionine Using the method of Example 3, Step B, the methyl ester of the product of Example 9 was converted to the title compound.

Anal. Calcd for C$_{25}$H$_{36}$N$_4$O$_5$S2.1.5 TFA: C, 49.77; H, 5.59; N, 8.29. Found: C, 50.09; H, 5.72; N, 8.62.

EXAMPLE 11

Preparation of N-[2(S)-(2(S)-Pyroglutamylamino-3(S)-methylpentyloxy)-3-phenylpropionyl]-methionine methyl ester Using the method of Example 9, substituting pyroglutamic acid for imidazole-4-acetic acid in Step H, the title compound was obtained.

Anal. Calcd for C$_{25}$H$_{39}$N$_3$O$_5$S.0.25 CH$_2$Cl$_2$: C, 58.89; H, 7.73; N, 8.16. Found: C, 59.01; H, 7.37; N, 7.87.

EXAMPLE 12

Preparation of N-[2(S)-(2(S)-Pyroglutamylamino-3(S)-methylpentyloxy)-3-phenylpropionyl]-methionine Using the method of Example 3, Step B, the ester prepared in Example 11 was converted to the title compound.

Anal. Calcd for $C_{27}H_{37}N_3O_6S$: C, 56.32; H, 7.03; N, 7.76. Found: C, 56.15; H, 6.90; N, 7.80.

EXAMPLE 13

Preparation of
N-[2(S)-(2(S)-((Imidazol-4-ylcarbonyl)amino-3(S)-methylpentyloxy)-3-phenylpropionyl]-methionine methyl ester Using the method for Example 9, substituting imidazole-4-carboxylic acid for imidazole-4-acetic acid in Step H, the title compound was obtained.

Anal. Calcd for $C_{25}H_{36}N_4O_5S$: C, 58.45; H, 7.26; N, 10.91. Found: C, 58.24; H, 6.97; N, 10.70.

EXAMPLE 14

Preparation of
N-[2(S)-(2(S)-((Imidazol-4-ylcarbonyl)amino-3(S)-methylpentyloxy)-3-phenylpropionyl]-methionine Using the method of Example 3, Step B, the ester prepared in Example 13 was convened to the title compound.

Anal. Calcd for $C_{24}H_{34}N_4O_5S.1.25$ TFA: C, 50.17; H, 5.59; N, 8.82. Found: C, 50.15; H, 5.68; N, 8.89.

EXAMPLE 15

Preparation of
N-[2(S)-(2(S)-((3-Picolinyl)amino-3(S)-methylpentyloxy)-3-phenylpropionyl]-methionine Step A: Preparation of N-[2(S)-(2(S)-((3-Picolinyl)amino-3(S)-methylpentyloxy)-3-phenylpropionyl]-methionine methyl ester A 100 mg (0.22 mmol) sample of 2(S)-Amino-3(S)-methyl)pentyloxy)-3-phenylpropionyl-methionine methyl ester hydrochloride, prepared as described in Example 9, Steps A–G, was dissolved in 5 mL of methanol and 3A molecular sieves were added. To this solution were added nicotinaldehyde (25 mL, 0.27 mmol), potassium acetate (80 mg, 0.22 mmol) and sodium cyanoborohydride (21 mg, 0.34 mmol). The mixture was stirred overnight at room temperature and filtered through a glass fiber disc. The mixture was concentrated and worked up in the standard manner to afford 110 mg of crude product. This material was further purified by chromatography on silica gel with 1–2% methanol in methylene chloride affording 65 mg of the title compound. The trifluoroacetate salt was characterized by FAB mass spectrum, m/z=502 (M+1).

Step B: Preparation of N-[2(S)-(2(S)-((3-Picolinyl)amino-3(S)-methylpentyloxy)-3-phenylpropionyl]-methionine Using the method of Example 3, Step B, the ester obtained in Step A was converted to the title compound.

Anal. Calcd for $C_{26}H_{37}N_3O_4S.2.85$ TFA: C, 46.85; H, 4.94; N, 5.17. Found: C, 46.81; H, 5.00; N, 5.55.

EXAMPLE 16

N-[2 (S)-(2(S)-((Histidyl)amino-3 (S)-methylpentyloxy)-3-phenylpropionyl]-methionine methyl ester Using standard methods of solution phase peptide synthesis, 2(S)-(2(S)-Amino-3(S)-methyl)pentyloxy)-3-phenylpropionyl-methionine methyl ester hydrochloride, prepared as described in Example 9, Steps A–G, was coupled to histidine.

Anal. Calcd for $C_{27}H_{41}N_5O_4S.3$ TFA: C, 45.36; H, 5.08; N, 8.02. Found: C, 45.41; H, 5.31; N 8.01.

EXAMPLE 17

N-[2(S)-(2(S)-((Histidyl)amino-3(S)-methylpentyloxy)-3-phenylpropionyl]-methionine The product of Example 16 was saponified using the method of Example 3, Step B, to obtain the title compound.

Anal. Calcd for $C_{26}H_{39}N_5O_5S.3$ TFA: C, 43.89; H, 4.83; N, 8.00. Found: C, 44.16; H, 5.12; N, 8.01.

EXAMPLE 18

Preparation of
N-(1-Naphthylmethyl)-N-[2(S)-((pyroglutamyl)-amino)-3(S)-methylpentyl]-glycyl-methionine methyl ester trifluoroacetate salt Step A: Preparation of N-(2(S)-t-butoxycarbonylamino)-3-methylpentyl)glycine methyl ester Glycine methyl ester hydrochloride (4.41 g, 0,035 mol) was dissolved in 1,2-dichloroethane (50 mL)- DMF (5 mL) and treated with 3A molecular sieves (10 g and N-t-butoxycarbonylisoleucinal (6.3 g, 0.029 mol) with stirring at 0° C. Sodium triacetoxyborohydride (9.27 g, 0.044 mol) was added, and the pH of the mixture was adjusted to 6 with triethylamine (3 mL, 0,022 mol). After stirring for 18 h the mixture was filtered, concentrated to a small volume and partitioned between EtOAc and water. The aqueous layer was extracted with EtOAc (2×50 mL). The combined organic phase was washed with aqueous saturated $NaHCO_3$ solution, brine, and dried ($Na_2SO_4$). Filtration and concentration gave 3.88 g (54%) of the title compound after purification by chromatography ($SiO_2$, EtOAc: hexane, 1:3). $^1H$ NMR ($CDCl_3$) δ4.69 (m, 1H), 3.72 (s, 3H), 3.48–3.62 (m, 1H), 3.42 (ABq, 2H), 2.65 (d, 2H, J=6 Hz), 1.4–1.6 (m, 2H), 1.48 (s, 9H), 1.04–1.2 (m, 1H), 0.85–0.95 (m, 6H).

Step B: Preparation of N-[2(S)-t-Butoxycarbonylamino)-3-methylpentyl]-N-(1-naphthylmethyl)glycine methyl ester N-[2(S)-t-Butoxycarbonylamino)-3-methylpentyl]-glycine methyl ester (2.00 g, 6.97 mmol) was dissolved in 1,2-dichloroethane (56 ml) and 3A molecular sieves were added followed by 1-naphthaldehyde (1.89 ml, 13.9 mmol) and sodium triacetoxyborohydride (6.65 g, 31.4 mmol). The mixture was stirred at ambient temperature for 16 h, and filtered through glass fiber paper and concentrated. The residue was partitioned between EtOAc and sat. $NaHCO_3$ (100 ml/25 ml). The aqueous layer was washed with EtOAc (3×50 ml). The organic layers were combined, dried with $Na_2SO_4$, filtered, and concentrated to give 5.0 g of crude product which was purified by chromatography (silica gel 1:6 to 1:3 ethyl acetate in hexane) to give 3.8 g of pure product. $^1H$ NMR ($CD_3OD$) δ8.44–8.38 (d, 1H, J=6 Hz), 7.88–7.77 (m, 2H), 7.55–7.35 (m, 4H), 6.34–6.27 (m, 1H), 4.25 (ABq, 2H), 3.66 (s, 3H), 3.40–3.23 (m, 1H), 2.95–2.85 (dd, 1H, J=6, 15 Hz), 2.68–2.57 (dd, 1H, J=6, 15 Hz), 1.57–1.46 (m, 1H), 1.43 (s, 9H), 1.34–1.18 (m, 2H), 1.06–0.85 (m, 1H), 0.85–0.71 (m, 6H).

Step C: Preparation of N-[2(S)-t-Butoxycarbonylamino)-3-methylpentyl]-N-(1-naphthylmethyl)glycine N-[2(S)-t-Butoxycarbonylamino)-3-methylpentyl]-N-(1-naphthylmethyl)glycine methyl ester (2.61 g, 6.10 mmol) was dissolved in MeOH (50 ml) and 1N NaOH (24.4 ml, 24.4 mmol) was added. The mixture was stirred at ambient temperature for 4 h and concentrated. The resulting residue was dissolved in H₂O (25 ml) and neutralized with 1N HCl (24.4 ml). The aqueous layer was washed with EtOAc (3×50 ml). The organic layers were combined, dried with Na₂SO₄, filtered, and concentrated to give 2.29 g of product. ¹H NMR (CD₃OD); δ8.48–8.39 (d, 1H, J=6 Hz), 8.03–7.91 (t, 2H, J=6 Hz), 7.75–7.48 (m, 4H) 5.00–4.93 (d, 1H, J=12 Hz), 4.78–4.66 (d, 1H, J=12 Hz), 3.80–3.58 (m, 3H), 3.49–3.40 (dd, 1H, J=3, 12 Hz), 3.09–2.98 (dd, 1H, J=3, 12 Hz), 1.42 (s, 9H), 1.37–1.28 (m, 2H), 1.80–1.00 (m, 1H), 0.94–0.78 (m, 6H).

Step D: Preparation of N-[2(S)-t-Butoxycarbonylamino)-3-methylpentyl]-N-(1-naphthylmethyl)glycine-methionine methyl ester N-[2(S)-t-Butoxycarbonylamino)-3-methylpentyl]-N-(1-naphthylmethyl)glycine (2.29 g, 5.53 mmol), dissolved in DMF (20 mL), was treated with HOBT (0.822 g, 6.08 mmol), EDC (1.17 g, 6.08 mmol), and methionine methyl ester hydrochloride (1.21 g, 6.08 mmol). The pH was adjusted to 7.5 with Et₃N (1.7 mL, 12 mmol) and the mixture was stirred at ambient temperature for 24 h. The mixture was concentrated, and the residue was partitioned between EtOAc (50 mL) and saturated NaHCO₃ solution (25 mL). The aqueous layer was extracted with EtOAc (1×30 mL). The organic layers were combined, washed with brine (1×25 mL), dried (Na₂SO₄), filtered, and concentrated to give 3.2 g of crude product which was purified by chromatography (silica gel eluting with 1:3 to 1:2 ethyl acetate in hexane) to give 2.82 g of pure product. ¹H NMR (CD₃OD); δ8.36–8.29 (d, 1H, J=6 Hz), 7.93–7.86 (d, 1H, J=6 Hz), 7.85–7.80 (d, 1H, J=6 Hz), 7.61–7.39 (m, 4H), 6.60–6.52 (m, 1H), 4.32–4.06 (m, 2H), 3.90–3.69 (m, 1H), 3.65 (s, 3H), 3.27–3.14 (m, 2H), 2.93–2.70 (m, 2H), 2.19–1.78 (m, 6H), 1.63–1.30 (m, 13H), 1.19–1.05 (m, 1H), 0.95–0.81 (m, 6H).

Step E: Preparation of N-[2(S)-amino-3-methylpentyl)-N-(1-naphthylmethyl)glycyl-methionine methyl ester hydrochloride N-[2(S)-(t-Butoxycarbonylamino)-3-methylpentyl]-N-(1-naphthylmethyl)glycyl-methionine methyl ester (2.82 g, 5.04 mmol) was dissolved in EtOAc (50 mL) and cooled to −25° C. HCl was bubbled through the mixture until TLC (95:5 CH₂Cl₂:MeOH) indicated complete reaction. Nitrogen was bubbled through the mixture to remove excess HCl and the mixture was then concentrated to give 2.68 g of the title compound. ¹H NMR (CD₃OD); δ8.34–8.28 (d, 1H, J=6 Hz), 8.00–7.92 (d, 2H, J=6 Hz), 7.83–7.71 (m, 1H), 7.68–7.49 (m, 3H), 4.76–4.55 (m, 4H), 3.84–3.75 (m, 2H), 3.71 (s, 3H), 3.59–3.70 (m, 1H), 3.21–3.00 (m, 2H), 2.57–2.38 (m, 3H), 2.17–2.04 (m, 4H), 1.97–1.81 (m, 1H), 1.63–1.50 (m, 1H), 1.39–1.20 (m, 1H), 1.19–1.00 (m, 1H), 0.95–0.79 (m, 6H).

Step F: Preparation of N-(1-Naphthylmethyl)-N-[2(S)-((pyroglutamyl)amino)-3(S)-methylpentyl]-glycyl-methionine methyl ester trifluoroacetate salt (S)-(−)Pyroglutamic acid (0.146 g, 1.13 mmol), dissolved in DMF (10 mL), was treated with HOBT (0.153 g, 1.13 mmol), EDC (0.217 g, 1.13 mmol), and N-[2(S)-amino-3-methylpentyl)-N-(1-naphthylmethyl)glycyl-methionine methyl ester hydrochloride (0.500 g, 0.940 mmol). The pH was adjusted to 7.5 with Et₃N (0.45 mL, 3.0 mmol) and the mixture was stirred at ambient temperature for 24 h. The mixture was concentrated and the residue was partitioned between EtOAc (50 mL) and saturated NaHCO₃ solution (25 mL). The aqueous layer was extracted with EtOAc (1×30 mL). The combined organic layer was washed with brine (1×25 mL), dried (Na₂SO₄), filtered, and concentrated to give 0.589 g of crude product which was purified by chromatography (silica gel, eluting with 99:1 to 95:5 CH₂Cl₂:MeOH) to give 0.250 g of pure product. This material was converted to the trifluroracetate salt by dissolving in 0.1% TFA in H₂O and lyophilization to give 0.289 g of the title compound. ¹H NMR (CD₃OD); δ8.31–8.21 (d, 1H, J=9 Hz), 7.91–7.76 (m, 2H), 7.62–7.35 (m, 4H), 4.42–4.30 (m, 1H), 4.25–3.99 (m, 4H), 3.69 (s, 3H), 2.94–2.74 (m, 2H), 2.55–2.48 (m, 1H), 2.40–1.78 (m, 7H), 1.95 (s, 3H), 1.66–1.53 (m, 2H), 1.50–0.99 (m, 3H), 0.95–0.78 (m, 6H).

Anal. Calcd for $C_{30}H_{41}N_4O_5S.1$ TFA.1.75 H₂O: C, 53.73; H, 6.41; N, 7.83. Found: C, 53.71; H, 6.04; N, 8.24.

EXAMPLE 19

Preparation of
N-(1-Naphthylmethyl)-N-[2(S)-((pyroglutamyl)-amino)-3(S)-methylpentyl]-glycyl-methionine trifluoroacetate salt N-(1-Naphthylmethyl)-N-[2(S)-(pyroglutamyl)amino)-3(S)-methylpentyl]-glycyl-methionine methyl ester (0.057 g, 0.10 mmol) was dissolved in MeOH (3 ml), cooled to 0°, and 1N NaOH (0.40 ml, 0.40 mmol) was added. The mixture was stirred at ambient temperature for 4 h and concentrated. The resulting residue was dissolved in H₂O (5 ml) and neutralized with 1N HCl (0.40 ml, 0.40 mmol). The aqueous layer was washed with EtOAc (3×10 ml). The organic layers were combined, dried with Na₂SO₄, filtered, and concentrated to give 0.048 g of crude product. Purification by preparative HPLC (Waters C-18 Prep Pak eluting with acetonitrile/0.1% TFA in H₂O gradient) gave 0.035 g of compound after lyophilization. ¹H NMR (CD₃OD); δ8.39–8.32 (d, 1H, J=9 Hz), 8.06–7.95 (m, 2H), 7.81–7.51 (m, 4H), 4.77–4.58 (m, 1H), 4.55–4.43 (m, 1H), 4.24–4.06 (m, 2H), 3.97–3.73 (m, 2H), 3.62–3.38 (m, 1H), 3.28–3.11, m, 1H), 2.50–2.17 (m, 6H), 2.13–1.94 (m, 1H), 2.03 (s, 3H) 1.88–1.71 (m, 2H), 1.68–1.55 (m, 1H), 1.53–1.38 (m, 1H), 1.27–1.12 (m, 1H), 1.03–0.83 (m, 6H).

Anal. Calcd for $C_{29}H_{40}N_4O_5S.1.8$ TFA: C, 51.38; H, 5.53; N, 7.35. Found: C, 51.10; H, 5.84; N, 7.75.

EXAMPLE 20

Preparation of
N-(1-Naphthylmethyl)-N-[2(S)-((imidazol-4-ylacetyl)-amino)-3(S)-methylpentyl]-glycyl-methionine methyl ester 4-Imidazoleacetic acid (0.064 g, 0.395 mmol), dissolved in DMF (5 mL) was treated with HOBT (0.053 g, 0.40 mmol), EDC (0.076 g, 0.40 mmol), and N-[2(S)-amino-3-methylpentyl)-N-(1-naphtylmethyl)glycyl-methionine methyl ester hydrochloride (0.175 g, 0.329 mmol). The pH was adjusted to 7.5 with Et₃N (0.15 mL, 1.1 mmol) and the mixture was stirred at ambient temperature for 24 h. After concentration, and the mixture was partitioned between EtOAc (20 mL) and saturated NaHCO₃ solution (10 mL). The aqueous layer was washed with EtOAc (1×20 mL). The organic layers were combined, washed with brine (1×10 m), dried (Na₂SO₄), filtered and concentrated to give 0.170 g of crude product. Purification by chromatography (silica gel, eluting with 1 to 3% methanol in methylene chloride) gave 0.080 g of pure product. ¹H NMR (CD₃OD); δ8.30–8.25 (d, 1H, J=9 Hz), 7.91–7.86 (d, 1H, J=6 Hz), 7.85–7.79 (d, 1H, J=9 Hz), 7.56 (s, 1H), 7.55–7.38 (m, 4H), 6.9 (s, 1H), 4.37–4.27 (m, 1H), 4.23–4.04 (m, 3H), 3.67 (s, 3H), 3.49 (ABq, 2H), 3.25 (ABq, 2H), 2.90–2.70 (m, 2H), 2.21–1.97 (m, 2H), 1.95 (s, 3H), 1.88–1.74 (m, 1H), 1.64–1.46 (m, 2H), 1.44–1.25 (m, 1H), 1.14–0.98 (m, 1H), 0.93–0.77 (m, 6H).

FAB mass spectrum m/z=568 (M+1).

EXAMPLE 21

Preparation of
N-(1-Naphthylmethyl)-N-[2(S)-((imidazol-4-ylacetyl)-amino)-3-methylpentyl]-glycyl-methionine trifluoroacetate salt N-(1-Naphthylmethyl)-N-[2(S)-(imidazol-4-ylacetyl)-amino)-3-methylpentyl]-glycyl-methionine methyl ester (0.058 g, 0.10 mmol) was dissolved in MeOH (3 ml), cooled to 0° C., and 1N NaOH (0.41 ml, 0.41 mmol) was added. The mixture was stirred at ambient temperature for 4 h and concentrated. The residue was dissolved in $H_2O$ (5 ml) and neutralized with 1N HCl (0.41 ml, 0.41 mmol). The aqueous layer was extracted with EtOAc (3×10 ml). The organic layers were combined, dried with $Na_2SO_4$, filtered, and concentrated to give 0.042 g of crude product. The crude product was purified by preparative HPLC (Waters C-18 Prep Pak eluting with acetonitrile/0.1% TFA in $H_2O$ gradient) to give 0.025 g of compound after lyophilization. $^1H$ NMR ($CD_3OD$); δ8.75 (s, 1H), 8.31–8.21 (m, 1H), 7.98–7.87 (m, 2H), 7.64–7.40 (m, 4H), 7.34 (s, 1H), 4.73–4.55 (m, 1H), 4.51–4.35 (m, 2H), 4.18–4.06 (m, 1H), 3.75–3.50 (m, 4H), 3.33–3.19 (m, 1H), 3.13–2.97 (m, 1H), 2.39–2.13 (m, 2H), 2.08–1.86 (m, 1H), 1.99 (s, 3H), 1.8–1.51 (m, 2H), 1.49–1.35 (m, 1H), 1.24–1.08 (m, 1H), 0.95–0.79 (m, 6H).

Anal. Calcd for $C_{29}H_{39}N_5O_4S.3$ TFA: C, 46.93; H, 4.73; N, 7.82. Found: C, 47.01; H, 5.09; N, 8.03.

EXAMPLE 22

Preparation of
N-(1-Naphthylmethyl)-N-[2(S)-((Imidazol-4-yl-carbonyl)amino)-3(S)-methylpentyl]-glycyl-methionine methyl ester Using the methods of Example 18, substituting imidazole-4-carboxylic acid for pyroglutamic acid, the title compound was prepared.

Anal. Calcd for $C_{29}H_{39}N_5O_4S.2$ TFA.2$H_2O$: C, 48.46; H, 5.55; N, 8.56. Found: C, 48.22; H, 5.30; N, 8.73.

EXAMPLE 23

Preparation of
N-(1-Naphthylmethyl)-N-[2(S)-((Imidazol-4-yl-carbonyl)amino)-3(S)-methylpentyl]-glycyl-methionine Using the method of Example 19, the product of Example 22 was converted to the title compound.

Anal. Calcd for $C_{28}H_{37}N_5O_4S.2.25$ TFA: C, 49.02; H, 4.97; N, 8.80. Found: C, 48.70; H, 5.05; N, 8.90.

EXAMPLE 24

Preparation of
N-Benzyl-N-[2(S)-((Pyroglutamyl)amino)-3(S)-methylpentyl]-glycyl-methionine methyl ester Step A: Preparation of N-Benzyl-N-(2(S)-t-butoxy-carbonylamino)-3-methylpentyl)glycine ethyl ester N-t-Butoxycarbonylisoleucinal (1.1 g, 5.1 mmol), N-benzylglycine (0.94 mL, 5 mmol), and acetic acid (0.14 mL, 2.5 mmol) were dissolved in dichloroethane (50 mL) with stirring under argon at 0° C. 3A Molecular sieves (2 g) were added followed by sodium triacetoxyborohydride (1.52 g, 7.14 mmol). The mixture was stirred at ambient temperature for 6 h, then filtered, and concentrated to dryness. The residue was partitioned between EtOAc (50 mL) and aqueous saturated $NaHCO_3$ solution (50 mL). The organic layer was separated, washed with brine and dried ($Na_2SO_4$). Filtration and concentration gave 1.86 g (95%) of the title compound as a colorless oil. $^1H$ NMR ($CDCl_3$) δ7.2–7.4 (m, 5H), 4.8–4.92 (m, 1H), 4.16 (d, 2H, J=7.2 Hz), 3.87 (d, 1H, J=13 Hz), 3.65–3.74 (m, 1H), 3.66 (d, 1H, J=13 Hz), 3.33 (s, 2H), 2.77 (dd, 1H, J=6, 13 Hz), 2.49 (dd, 1H, J=6, 14 Hz), 1.6–1.8 (m, 1H), 1.48 (s, 9H), 1.27 (t, 3H, J=7.2 Hz), 1.3–1.45 (m, 1H), 1.0–1.17 (m, 1H), 0.90 (t, 3H, J=7 Hz), 0.85 (d, 3H, J=7 Hz).

Step B: Preparation of N-Benzyl-N-[2(S)-((Pyroglutamyl)-amino)-3(S)-methylpentyl]-glycyl-methionine methyl ester The product of Step A was converted to the title compound by the methods described in Example 18, Steps B–F.

Anal. Calcd for $C_{26}H_{40}N_4O_5S.1.9$ TFA.0.3 $CH_3CN$: C, 48.70; H, 5.75; N, 8.03. Found: C, 48.58; H, 6.00; N, 8.33.

EXAMPLE 25

Preparation of
N-Benzyl-N-[2(S)-((Pyroglutamyl)amino)-3(S)-methylpentyl]-glycyl-methionine Using the method of Example 19, the product of Example 26 was converted to the title compound.

Anal. Calcd for $C_{25}H_{38}N_4O_5S.1$ TFA.2.5 $H_2O$: C, 48.71; H, 6.66; N, 8.42. Found: C, 48.68; H, 6.67; N, 8.40.

EXAMPLE 26

Preparation of
N-Benzyl-N-[2(S)-((Imidazol-4-ylcarbonyl)amino)-3(S)-methylpentyl]-glycyl-methionine methyl ester The title compound was obtained using the method of Example 26, substituting 4-imidazolecarboxylic acid for pyroglutamic acid.

Anal. Calcd for $C_{25}H_{37}N_5O_4S.1.5$ TFA: C, 49.70; H, 5.96; N, 10.59. Found: C, 49.84; H, 5.75; N, 10.38.

EXAMPLE 27

Preparation of
N-Benzyl-N-[2(S)-((imidazol-4-ylcarbonyl)amino)-3(S)-methylpentyl]-glycyl-methionine Using the method of Example 19, the product of Example 28 was converted to the title compound.

Anal. Calcd for $C_{24}H_{35}N_5O_4S.2$ TFA.0.5 $H_2O$: C, 46.28; H, 5.27; N, 9.64. Found: C, 46.13; H, 4.98; N, 9.77.

EXAMPLE 28

Preparation of
N-Benzyl-N-[2(S)-((Imidazol-4-ylacetyl)amino)-3(S)-methylpentyl]-glycyl-methionine methyl ester The title compound was obtained using the method of Example 26, substituting 4-imidazole acetic acid for pyroglutamic acid.

FAB mass spectrum m/z=518 (M+1).

EXAMPLE 29

Preparation of
N-Benzyl-N-[2(S)-((Imidazol-4-ylacetyl)amino)-3(S)-methylpentyl]-glycyl-methionine Using the method of Example 19, the product of Example 30 was converted to the title compound.

Anal. Calcd for $C_{25}H_{37}N_5O_4S.3$ TFA.0.5 $CH_3CN$: C, 44.36; H, 4.83; N, 8.89. Found: C, 44.67; H, 4.98; N, 9.03.

EXAMPLE 30

Preparation of
N-[1-(Pyroglutamylamino)cyclopent-1-ylmethyl]-N-(1-naphthylmethyl)glycyl-methionine methyl ester Step A: Preparation of 1-tert-(butyloxy)carbonylamino-cyclopentane-1-carboxaldehyde The title compound was prepared by a Swern oxidation (3 equivalents of pyridine-sulfurtrioxide complex and excess triethyl amine in $DMSO/CH_2Cl_2$) of BOC protected 1-amino-1-hydroxymethyl-cyclopentane (Aldrich).

Step B: Preparation of N-[1-(Pyroglutamylamino)cyclopent-1-ylmethyl]-N-(1-naphthylmethyl)glycyl-methionine methyl ester Following the procedure described in Example 18, but substituting the 1-tert-(butyloxy)carbonylaminocyclopentane-1-carboxaldehyde from Step A for N-t-butoxycarbonylisoleucinal provided the title compound.

Anal. Calcd for $C_{30}H_{40}N_4O_5S.F3CCOOH.0.4$ EtOAc C, 54.08; H, 5.73; N, 7.69. Found: C, 54.08; H, 5.77; N, 8.07.

EXAMPLE 31

Preparation of
N-[1-(Pyroglutamylamino)-cyclopent-1-ylmethyl]-N-(1-naphthylmethyl)glycyl-methionine Following the procedure described in Example 19, but substituting the ester from Example 30 provided the title compound.

Anal. Calcd for $C_{29}H_{38}N_4O_5S.0.5$ EtOAc.1.75 $H_2O$ C, 59.07; H, 7.28; N, 8.89. Found: C, 59.07; H, 6.67; N, 8.95.

EXAMPLE 32

Preparation of
2(S)-{2(S)-[2(S,R)-(Imidazol-4-yl)-2-aminoacetyl)-amino]-3(S)-methylpentyloxy}-3-phenylpropionyl-methionine sulfone methyl ester and
2(S)-{2(S)-[2(R,S)-(Imidazol-4-yl)-2-aminoacetyl)-amino]-3(S)-methylpentyloxy}-3-phenylpropionyl-methionine sulfone methyl ester Step A: Preparation of racemic 2-(t-Butoxycarbonyl)amino-2-(N-t-butoxycarbonylimidazol-4-yl)acetic acid To a solution of 1-(triphenylmethyl)imidazol-4-ylcarboxaldehyde (1.70 g, 5.02 mmol) and trimethylsilyl cyanide (1.36 mL, 9.9 mmol) in methylene chloride (75 ml) was added zinc iodide (159 mg, 0.497 mmol) and the mixture stirred at room temperature under argon for 24 h. The resulting mixture was evaporated in vacuo and the residue redissolved in methanol (75 ml) saturated with gaseous ammonia. This solution was heated at 48° C. for 1 h. The solution was then evaporated in vacuo and the residue purified by flash chromatography (80 g $SiO_2$, 4% methanol saturated with ammonia/methylene chloride) to provide amino-1-(triphenylmethyl)-1H-imidazol-4-ylacetonitrile.

This compound (0.80 g, 2.2 mmol) was dissolved in methylene chloride (19 ml) and treated with trifluoroacetic acid (10 ml) and triethylsilane (1 ml, 6.26 mmol) for 10 min. The solution was evaporated in vacuo and the residue partitioned between 5M HCl (10 ml) and diethyl ether (30 ml). The ether layer was extracted with 5M HCl (10 ml). The combined aqueous extract was washed with diethyl ether (20 ml), diluted with 12M HCl (10 ml) and heated at reflux for 30 h. The resulting solution was evaporated in vacuo and dried under high vacuum to provide a whim solid. The solid was dissolved in methanol and treated with triethylamine (920 µl, 6.60 mmol) and di-t-butyl-dicarbonate (1.92 g, 8.80 mmol) and stirred at room temperature for 18 h. The resulting mixture was evaporated in vacuo and partitioned between 10% aq. citric acid (50 ml) and methylene chloride. The organic extract was washed with brine (20 ml), dried-($MgSO_4$) and evaporated in vacuo. The residue was purified by flash chromatography ($SiO_2$, 10% methanol/methylene chloride) to provide the title compound.

$^1$H NMR($CD_3OD$, 300 MHz) δ8.14 (1H, s), 7.36 (1H, s), 5.03 (1H, s), 1.64 (9H, s) and 1.43 (9H, s)ppm.

Step B: Preparation of 2(S)-{2(S)-[2(S,R)-(Imidazol-4-yl)-2-aminoacetyl)amino]-3(S)-methylpentyloxy}-3-phenyl-propionyl-methionine sulfone methyl ester and 2(S)-{2(S)-[2(R,S)-(Imidazol-4-yl)-2-aminoacetyl)amino]-3(S)-methylpentyloxy}-3-phenylpropionyl-methionine sulfone methyl ester The racemic amino acid was coupled with the intermediate prepared in Example 9, Step G using EDC and HOOBT. The coupling was slow at room temperature and was accelerated by warming to 40°–50° C. The Boc protecting groups were removed from the coupled product using TFA and the diastereomeric title compounds were purified by preparative HPLC.

2(S)-{2(S)-[2(S,R)-(Imidazol-4-yl)-2-aminoacetyl)amino]-3(S)-methylpentyloxy}-3-phenylpropionyl-methionine sulfone methyl ester Anal. Calcd for $C_{26}H_{39}N_5O_7S.2.5$ TFA.0.45 $H_2O$: C, 43.35; H, 4.98; N, 8.15. Found: C, 43.33; H, 4.97; N, 8.15.

2(S)-{2(S)-[2(R,S)-(Imidazol-4-yl)-2-aminoacetyl)amino]-3(S)-methylpentyloxy}-3-phenylpropionyl-methionine sulfone methyl ester Anal. Calcd for $C_{26}H_{39}N_5O_7S.2.35$ TFA.0.55 $H_2O$: C, 43.71; H, 5.07; N, 8.30. Found: C, 43.71; H, 5.09; N, 8.27.

EXAMPLE 33

Preparation of
N-(1-Naphthylmethyl)-N-[2(S)-(N'-(L-pyroglutamyl)-N'-methylamino)-3(S)-methylpentyl]-glycyl-methionine trifluoroacetate salt Step A: Preparation of N-[2(S)-(N'-t-Butoxycarbonyl-N'-methylamino)-3-methylpentyl]-N-(1-naphthylmethyl)glycine N-[2(S)-(t-Butoxycarbonylamino)-3(S)-methylpentyl]-N-(1-naphthylmethyl)glycine (0.5 g, 1.21 mmol), dissolved in dry THF (2 mL), was cooled to 0° C. and sodium bis(trimethylsilyl)amide (1M in THF, 2.5 mL, 2.5 mmol) was added. The mixture was stirred for 5 min. The anion was added to a solution of iodomethane (0.375 mL, 6.03 mmol) in 1 mL dry THF at 0° C. The mixture was stirred overnight at ambient temperature. EtOAc (40 mL) was added and the organic solution was extracted with 1N NaOH (30 mL) and water (30 mL). The aqueous layer was acidified with cold 1N HCl and extracted with EtOAc (3×30 mL). The organic layers were combined, washed with brine (25 mL), dried (MgSO$_4$), filtered, and concentrated to give the pure product. $^1$H NMR (CDCl$_3$) δ8.13 (d, 1H, J=8 Hz), 7.84 (d, 1H, J=8 Hz), 7.80 (d, 1H, J=7.5 Hz), 7.45–7.57 (m, 2H), 7.36–7.45 (m, 2H), 4.42 (d, 1H, J=13 Hz), 3.97–4.08 (m, 1H), 3.83 (d, 1H, J=13 Hz), 3.59 (d, 1H, J=15 Hz), 3.21 (d, 1H, J=15 Hz), 2.53–2.64 (m, 2H), 2.37 (br s, 1H), 1.89 (s, 3H), 1.44 (s, 9H), 1.19–1.32 (m, 2H), 0.91–1.06 (m, 1H), 0.75–0.91 (m, 6H).

Step B: Preparation of N-[2(S)-(N'-t-Butoxycarbonyl-N'-methylamino)-3(S)-methylpentyl]-N-(1-naphthylmethyl)glycyl-methionine methyl ester N-[2(S)-(N'-t-Butoxycarbonyl-N'-methylamino)-3(S)-methylpentyl]-N-(1-naphthylmethyl)glycine (0.295 g, 0.688 mmol), dissolved in CH$_2$Cl$_2$ (10 mL), was treated with HOBT (0.102 g, 0.757 mmol), EDC (0.198 g, 1.03 mmol), and methionine methyl ester hydrochloride (0.151 g, 0.757 mmol). The pH was adjusted to 7.5 with Et$_3$N (0.24 mL, 1.7 mmol) and the mixture was stirred at ambient temperature for 4 h. The mixture was concentrated, and the residue was partitioned between EtOAc (40 mL) and 10% citric acid solution (25 mL). The aqueous layer was extracted with EtOAc (×30 mL). The organic layers were combined, washed with water (125 mL), saturated NaHCO$_3$ solution (25 mL), brine (25 mL), dried (MgSO$_4$), filtered, and concentrated to give a crude product, which was purified by chromatography (silica gel eluting with 1:3 ethyl acetate in hexane) to give the pure product. $^1$H NMR (CD$_3$OD) was similar to N-[2(S)-(t-butoxycarbonylamino)-3(S)-methylpentyl]-N-(1-naphthylmethyl)glycyl-methionine methyl ester with the addition of a singlet at δ2.41 for the N-methyl.

Step C: Preparation of N-[2(S)-(N'-methylamino)-3(S)-methylpentyl]-N-(1-naphthylmethyl)glycyl-methionine methyl ester hydrochloride N-[2(S)-(N'-t-Butoxycarbonyl-N'-methylamino)-3-methylpentyl]-N-(1-naphthylmethyl)glycyl-methionine methyl ester (0.239 g, 0.416 mmol) was dissolved in EtOAc (5 mL) and cooled to 0° C. HCl was bubbled through the mixture for 5 min. The mixture was stirred for 2 h at which time the reaction was complete. Argon was bubbled through the mixture to remove excess HCl and the mixture was then concentrated to give a solid which was triturated with ethyl ether to give the title compound. $^1$H NMR (CD$_3$OD) was similar to N-[2(S)-amino-3-methylpentyl]-N-(1-naphthylmethyl)glycyl-methionine methyl ester hydrochloride with the addition of a singlet at δ2.04 for the N-methyl.

Step D: Preparation of N-(1-Naphthylmethyl)-N-[2(S)-(N'-(L-pyroglutamyl)-N'-methylamino)-3(S)-methylpentyl]-glycyl-methionine methyl ester trifluoroacetate salt L-Pyroglutamic acid (0,064 g, 0.495 mmol), dissolved in DMF (2 mL), was treated with BOP-Cl (0.252 g, 0,990 mmol), and N-[2(S)-(N'-methylamino)-3-methylpentyl]-N-(1-naphthylmethyl)glycyl-methionine methyl ester hydrochloride (0,180 g, 0.330 mmol). The pH was adjusted to 7.5 with diisopropylethylamine (0.43 mL, 2.5 mmol) and the mixture was stirred at ambient temperature for 24 h. The mixture was concentrated and the residue was partitioned between EtOAc (60 mL) and 10% citric acid solution (30 mL). The aqueous layer was extracted with EtOAc (1×30 mL). The combined organic layer was washed with water (25 mL), saturated NaHCO$_3$ solution (25 mL), brine (25 mL), dried (MgSO$_4$), filtered, and concentrated to give a crude product. Purification by preparative HPLC (Waters C-18 Prep Pak eluting with acetonitrile/0.1% TFA in H$_2$O gradient) gave the title compound after lyophilization. $^1$H NMR (CD$_3$OD) was similar to N-(1-naphthylmethyl)-N-[2(S)-((pyroglutamyl)amino)-3(S)-methylpentyl]-glycyl-methionine methyl ester trifluoroacetate salt with the addition of a singlet at δ2.04 for the N-methyl.

Step E: Preparation of N-(1-Naphthylmethyl)-N-[2(S)-(N'-(pyroglutamyl)-N'-methylamino)-3(S)-methylpentyl]-glycyl-methionine trifluoroacetate salt N-(1-Naphthylmethyl)-N-[2(S)-N'-(pyroglutamyl)-N'-methylamino)-3(S)-methylpentyl]-glycyl-methionine methyl ester trifluoroacetate salt (0.040 g, 0.057 mmol) was dissolved in MeOH (1 ml), cooled to 0° C., and 1N NaOH (0.287 ml, 0.287 mmol) was added. The mixture was stirred at ambient temperature for 4 h. The mixture was cooled to 0° C., and 1N HCl (0.287 ml, 0,287 mmol) was added. The mixture was purified by preparative HPLC (Waters C-18 Prep Pak eluting with acetonitrile/0.1% TFA in H$_2$O gradient) to give the title compound after lyophilization. $^1$H NMR (CD$_3$OD); δ8.33 (d, 1H, J=8 Hz), 7.93–8.08 (m, 2H), 7.64–7.78 (m, 2H), 7.50–7.64 (m, 2H), 2.05 (s, 3H), 0.96 (d, 3H, 6 Hz), 0.85 (t, 3H, 6 Hz).

FAB MS m/z=571 (M+1).

EXAMPLE 34

Employing the methods described in Examples 9, 18 and 32 the following compounds were prepared:

N-{2(S)-[2(S,R)-(Imidazol-4-yl)-2-aminoacetyl]amino-3(S)-methylpentyl}-N-(1-naphthylmethyl)glycyl-methionine methyl ester Anal. Calcd for C$_{30}$H$_{42}$N$_6$O$_4$S.3 TFA: C, 46.75; H, 4.90; N, 9.09. Found: C, 46.60; H, 5.07; N, 9.24.

N-{2(S)-[2(R,S)-(Imidazol-4-yl)-2-aminoacetyl]amino-3(S)-methylpentyl}-N-(1-naphthylmethyl)glycyl-methionine methyl ester 2(S)-{2(S)-[2(S,R)-(Imidazol-4-yl)-2-aminoacetyl)amino]-3(S)-methylpentyloxy}-3-phenylpropionyl-methionine sulfone methyl ester 2(S)-{2(S)-[2(R,S)-(Imidazol-4-yl)-2-aminoacetyl)amino]-3(S)-methylpentyloxy}-3-phenylpropionyl-methionine sulfone methyl ester 2(S)-[2(S)-(L-Pyroglutamyl)amino-3(S)-methylpentyloxy]-3-methylbutanoyl-methionine methyl ester Anal. Calcd for C$_{22}$H$_{39}$N$_3$O$_6$S.0.4 H$_2$O: C, 54.95; H, 8.34; N, 8.74. Found: C, 54.96; H, ;8.18 N, 8.50.

(S)-[2(S)-(Imidazol-4-ylacetyl)amino-3(S)-methylpentyloxy]-3-methylbutanoyl-methionine methyl ester Anal. Calcd for C$_{22}$H$_{38}$N$_3$O$_5$S.0.35 H$_2$O: C, 55.40; H, 8.18; N, 11.75. Found: C, 55.51; H, 8.14; N, 11.36.

N-(Benzyl)-N-[2(S)-(2-oxopyrrolidin-5(R,S)-ylmethyl)amino-3(S)-methylpentyl]-glycyl-methionine methyl ester N-(Benzyl)-N-{2(S)-[((D,L)-2-thiazolyl)alanyl)amino]-3(S)-methylpentyl}-glycyl-methionine methyl ester N-(Benzyl)-N-[2(S)-(3-pyridylmethyl)amino-3(S)-methylpentyl]-glycyl-methionine methyl ester FAB MS m/z=501 (M+1).

2(S)-[2(S)-(2-Oxopyrrolidin-5(S)-ylmethyl)amino-3(S)-methylpentyloxy]-3-phenylpropionyl-methionine methyl ester 2(S)-[2(S)-(L-Pyroglutamyl)amino-3(S)-methylpentyloxy]-3-(1-naphthyl)propionyl-methionine sulfone methyl ester Anal. Calcd for C$_{30}$H$_{41}$N$_3$O$_8$S.0.55 H$_2$O: C, 57.05; H, 7.04; N, 6.65. Found: C, 57.07; H, 6.58; N, 6.66.

2(S)-[2(S)-(Imidazol-4-ylacetyl)amino-3(S)-methylpentyloxy]-3-(1-naphthyl)propionyl-methionine sulfone methyl ester Anal. Calcd for $C_{30}H_{40}N_4O_7S.0.65\ H_2O$: C, 58.84; H, 6.80; N, 9.15. Found: C, 58.85; H, 6.44; N, 8.91.

2(S)-[2(S)-(L-Pyroglutamyl)amino-3(S)-methylpentyloxy]-3-(2-naphthyl)propionyl-methionine sulfone methyl ester Anal. Calcd for $C_{30}H_{41}N_3O_8S.1.55\ H_2O$: C, 57.05; H, 7.04; N, 6.65. Found: C, 57.07; H, 6.49; N, 6.54.

2(S)-[2(S)-(Imidazol-4-ylacetyl)amino-3(S)-methylpentyloxy]-3-(2-naphthyl)propionyl-methionine sulfone methyl ester $^1$H NMR was consistent with the structure of this compound.

N-(Benzyl)-N-[2(S)-(tetrazol-1-ylacetyl)amino-3(S)-methylpentyl]-glycyl-methionine methyl ester N-(Benzyl)-N-[2(S)-nicotinoylamino-3(S)-methylpentyl]-glycyl-methionine methyl ester N-[2(S)-(L-Pyroglutamyl)amino-3(S)-methylpentyl]-N-(1-naphthylmethyl)glycyl-methionine sulfoxide methyl ester Anal. Calcd for $C_{30}H_{42}N_4O_6S.2.45\ TFA$: C, 48.39; H, 5.17; N, 6.47. Found: C, 48.30; H, 5.42; N, 6.84.

N-[2(S)-(L-pyroglutamyl)amino-3(S)-methylpentyl]-N-(1-naphthylmethyl)glycyl-methionine isopropyl ester Anal. Calcd for $C_{32}H_{46}N_4O_5S$: C, 64.19; H, 7.74; N, 9.36. Found: C, 63.78; H, 7.72; N, 9.32.

N-[2(S)-(L-pyroglutamyl)amino-3(S)-methylpentyl]-N-(4-quinolylmethyl)glycyl-methionine methyl ester Anal. Calcd for $C_{29}H_{41}N_5O_5S.1.75\ H_2O$: C, 57.73; H, 7.44; N, 11.61. Found: C, 57.76; H, 6.98; N, 11.68.

N-[2(S)-(L-pyroglutamyl)amino-3(S)-methylpentyl]-N-(1-naphthylmethyl)glycyl-methionine t-butyl ester Anal. Calcd for $C_{33}H_{48}N_4O_5S.1.2\ H_2O$: C, 62.47; H, 8.01; N, 8.83. Found: C, 62.10; H, 7.62; N, 9.22.

N-[2(S)-(L-pyroglutamyl)amino-3(S)-methylpentyl]-N-(1-naphthylmethyl)glycyl-glutamine t-butyl ester Anal. Calcd for $C_{33}H_{47}N_5O_6.H_2O$: C, 63.13; H, 7.87; N, 11.16. Found: C, 62.90; H, 7.54; N, 11.12.

N-[2(S)-(L-pyroglutamyl)amino-3(S)-methylpentyl]-N-(1-naphthylmethyl)glycyl-norleucine methyl ester Anal. Calcd for $C_{31}H_{44}N_4O_5.0.25\ H_2O$: C, 66.82; H, 8.05; N, 10.06. Found: C, 66.54; H, 7.98; N, 10.16.

N-[2(S)-(3-pyridylmethyl)amino-3(S)-methylpentyl]-N-(1-naphthylmethyl)glycyl-methionine methyl ester Anal. Calcd for $C_{31}H_{42}N_4O_3S.2.3\ TFA.0.55\ H_2O$: C, 51.95; H, 5.56; N, 6.81. Found: C, 51.94; H, 5.56; N, 6.84.

2(S)-{2(S)-[2-(Imidazol-4-yl)ethyl]amino-3(S)-methylpentyloxy}-3-phenylpropionyl-methionine sulfone methyl ester Anal. Calcd for $C_{26}H_{40}N_4O_6S\ 2.9\ TFA.0.05\ H_2O$: C, 43.99; H, 4.99; N, 6.45. Found: C, 43.98; H, 4.90; N, 6.97.

N-[2(S)-(L-pyroglutamyl)amino-3(S)-methylpentyl]-N-(1-naphthylmethyl)glycyl-serine methyl ester Anal. Calcd for $C_{28}H_{38}N_4O_6.0.75\ H_2O$: C, 62.26; H, 7.37; N, 10.37. Found: C, 62.47; H, 7.29; N, 10.18.

N-[2(S)-(L-pyroglutamyl)amino-3(S)-methylpentyl]-N-(1-naphthylmethyl)glycyl-homoserine lactone Anal. Calcd for $C_{28}H_{36}N_4O5.HCl.0.75\ EtOAc$: C, 61.02; H, 6.94; N, 9.18. Found: C, 60.52; H, 7.03; N, 9.45.

N-[2(S)-(L-pyroglutamyl)amino-3(S)-methylpentyl]-N-(cinnamyl)glycyl-methionine methyl ester Anal. Calcd for $C_{28}H_{42}N_4O_5S.1.75\ TFA$: C, 50.69; H, 5.91;N, 7.51. Found: C, 50.82; H, 6.04; N, 7.67.

N-[2(S)-(L-pyroglutamyl)amino-3(S)-methylpentyl]-N-(1-naphthylmethyl)glycyl-alanine methyl ester Anal. Calcd for $C_{28}H_{38}N_4O_5.0.5\ H_2O$: C, 64.71; H, 7.57; N, 10.78. Found: C, 64.74; H, 7.20; N, 10.85.

N-{2(S)-[2-(Imidazol-4-yl)ethyl]amino-3(S)-methylpentyl}-N-(1-naphthylmethyl)glycyl-methionine methyl ester FAB MS m/z=508 (M+1).

N-[2(S)-(L-pyroglutamyl)amino-3(S)-methylpentyl]-N-(1-naphthylmethyl)glycyl-alanine methyl ester N-[2(S)-(D-pyroglutamyl)amino-3(S)-methylpentyl]-N-(1-naphthylmethyl)glycyl-methionine methyl ester Anal. Calcd for $C_{30}H_{42}N_4O_5.0.5\ H_2O$: C, 62.15; H, 7.48; N, 9.66. Found: C, 62.07; H, 7.52; N, 9.62.

2(S)-[2(S)-(L-Pyroglutamyl)amino-3(S)-methylpentyloxy]-3-phenylpropionyl-methionine sulfone methyl ester Anal. Calcd for $C_{26}H_{39}N_3O_8S.0.75\ TFA.0.45\ H_2O$: C, 51.03; H, 6.33; N, 6.49. Found: C, 51.04; H, 6.36; N, 6.72.

N-[2(S)-(L-pyroglutamyl)amino-3(S)-methylpentyl]-N-(2,3-methylenedioxybenzyl)glycyl-methionine methyl ester Anal. Calcd for $C_{27}H_{40}N_4O_7S.2.1\ TFA$: C, 46.60; H, 5.28; N, 6.97. Found: C, 46.46; H, 5.38; N, 7.09.

N-[2(S)-(Imidazol-4-ylacetyl)amino-3(S)-methylpentyl]-N-(2,3-dihydrobenzofuran-7-ylmethyl)glycyl-methionine methyl ester Anal. Calcd for $C_{28}H_{41}\ N_5O_5S.0.4\ H_2O$: C, 59.32; H, 7.43; N, 12.35. Found: C, 59.33; H, 7.31; N, 12.01.

N-{2(S)-[3-(3-Indolyl)propionyl]amino-3(S)-methylpentyl}-N-(1-naphthylmethyl)glycyl-methionine methyl ester Anal. Calcd for $C_{36}H_{46}N_4O_4S.1.6\ TFA$: C, 57.89; H, 5.90; N, 6.89. Found: C, 57.94; H, 5.96; N, 6.83.

N-{2(S)-[3-(1-indolyl)propionyl]amino-3(S)-methylpentyl}-N-(1-naphthylmethyl)glycyl-methionine methyl ester Anal. Calcd for $C_{36}H_{46}N_4O_4S.1.65\ TFA$: C, 57.63; H, 5.86; N, 6.84. Found: C, 57.73; H, 5.94; N, 6.82.

N-[2(S)-(L-pyroglutamyl)amino-3(S)-methylpentyl]-N-(1-naphthylmethyl)glycyl-histidine methyl ester FAB MS m/z=576 (M+1). N-[2(S)-(L-pyroglutamyl)amino-3(S)-methylpentyl]-N-(cyclopropylmethyl)glycyl-methionine methyl ester FAB MS m/z=484 (M+1).

N-[2(S)-(Imidazol-4-ylacetyl)amino-3(S)-methylpentyl]-N-(cyclopropylmethyl)glycyl-methionine methyl ester FAB MS m/z=482 (M+1).

N-[2(S)-(L-pyroglutamyl)amino-3(S)-methylpentyl]-N-(2,3-dihydrobenzofuran-7-ylmethyl)glycyl-methionine methyl ester Anal. Calcd for $C_{28}H_{42}N_4O_6S.0.65\ H_2O$: C, 58.55; H, 7.60; N, 9.75. Found: C, 58.54; H, 7.34; N, 9.46.

2(S)-[2(S)-N-(L-Pyroglutamyl)-N-methylamino-3(S)-methylpentyloxy]-3-phenylpropionyl-methionine sulfone methyl ester Anal. Calcd for $C_{26}H_{39}N_3O_6S.0.4\ TFA.0.9\ H_2O$: C, 55.17; H, 7.12; N, 7.20. Found: C, 55.12; H, 6.97; N, 7.59.

N-[2(S)-(L-pyroglutamyl)amino-3(S)-methylpentyl]-N-(1-naphthylmethyl)glycyl-O-methylserine methyl ester Anal. Calcd for $C_{29}H_{40}N_4O_6.1.25\ H_2O$: C, 61.84; H, 7.61; N, 9.95. Found: C, 61.62; H, 7.03; N, 9.94.

N-(1-Naphthylmethyl)-N-[2(S)-(N'-(L-pyroglutamyl)-N'-methylamino)-3(S)-methylpentyl]-glycyl-methionine methyl ester FAB MS m/z=585 (M+1).

N-[1-(Pyroglutamylamino)cyclopent-1-ylmethyl]-N-(1-naphthylmethyl)glycyl-methionine methyl ester Anal. Calcd for $C_{30}H_{40}N_4O_5S$·TFA·0.4 EtOAc: C, 54.08; H, 5.73; N, 7.69. Found: C, 54.08; H, 5.77; N, 8.07.

N-[2(S)-(Pyridin-2-on-6-ylcarbonyl)amino-3(S)-methylpentyl]-N-(1-naphthylmethyl)glycyl-methionine methyl ester Anal. Calcd for $C_{30}H_{40}N_4O_5S$·TFA·$H_2O$: C, 55.61; H, 6.08; N, 7.86. Found: C, 55.61; H, 5.83; N, 7.55.

EXAMPLE 35

The following compounds were prepared by the method described in Example 19 employing the corresponding ester from Example 27. When the physical data for the corresponding ester is described in Example 34 is not provided, the corresponding ester was converted to the acid without isolation or was not characterized by physical analysis.

N-{2(S)-[2(S,R)-(Imidazol-4-yl)-2-aminoacetyl]amino-3(S)-methylpentyl}-N-(1-naphthylmethyl)glycyl-methionine Anal. Calcd for $C_{29}H_{40}N_6O_4S$·3.15 TFA·1.45 $H_2O$: C, 44.44; H, 4.87; N, 8.81. Found: C, 44.44; H, 4.86; N, 8.87.

N-{2(S)-[2(R,S)-(Imidazol-4-yl)-2-aminoacetyl]amino-3(S)-methylpentyl}-N-(1-naphthylmethyl)glycyl-methionine Anal. Calcd for $C_{29}H_{40}N_6O_4S$·3.05 TFA·1.1 $H_2O$: C, 45.03; H, 4.87; N, 8.98. Found: C, 45.01; H, 4.87; N, 9.04.

2(S)-{2(S)-[2(S,R)-(Imidazol-4-yl)-2-aminoacetyl)amino]-3(S)-methylpentyloxy}-3-phenylpropionyl-methionine sulfone This compound was prepared by in situ hydrolysis of the corresponding methyl ester.

2(S)-{2(S)-[2(R,S)-(Imidazol-4-yl)-2-aminoacetyl)amino]-3(S)-methylpentyloxy}-3-phenylpropionyl-methionine sulfone This compound was prepared by in sire hydrolysis of the corresponding methyl ester.

2(S)-[2(S)-(L-Pyroglutamyl)amino-3(S)-methylpentyloxy]-3-methylbutanoyl-methionine Anal. Calcd for $C_{21}H_{37}N_3O_6S$: C, 54.88; H, 8.12; N, 9.14. Found: C, 54.79; H, 7.97; N, 8.85.

2(S)-[2(S)-(Imidazol-4-ylacetyl)amino-3(S)-methylpentyloxy]-3-methylbutanoyl-methionine Anal. Calcd for $C_{21}H_{36}N_4O_5$·1.45 TFA·0.40 $H_2O$: C, 45.63; H, 6.13; N, 8.91. Found: C, 45.63; H, 6.10; N, 9.17.

N-(Benzyl)-N-[2(S)-(2-oxopyrrolidin-5(R,S)-ylmethyl)amino-3(S)-methylpentyl]-glycyl-methionine Anal. Calcd for $C_{25}H_{40}N_4O_4S$·2.65 HCl·0.55 $H_2O$: C, 50.19; H, 7.20; N, 9.37. Found: C, 50.24; H, 7.21; N, 8.97.

N-(Benzyl)-N-{2(S)-[((D,L)-2-thiazolyl)alanyl)amino]-3(S)-methylpentyl}-glycyl-methionine Anal. Calcd for $C_{26}H_{33}N_5O_4S_2$·0.8 TFA·2.45 $H_2O$: C, 41.84; H, 4.52; N, 7.72. Found: C, 41.85; H, 4.85; N, 7.66.

N-(Benzyl)-N-[2(S)-(3-pyridylmethyl)amino-3(S)-methylpentyl]-glycyl-methionine

Anal. Calcd for $C_{26}H_{38}N_4O_3S$·2.35 TFA·0.95 $H_2O$: C, 47.78; H, 5.52; N, 7.26. Found: C, 47.74; H, 5.50; N, 7.62.

2(S)-[2(S)-(2-Oxopyrrolidin-5(S)-ylmethyl)amino-3(S)-methylpentyloxy]-3-phenylpropionylmethionine This compound was prepared by in sire hydrolysis of the corresponding methyl ester 2(S)-[2(S)-(L-Pyroglutamyl)amino-3(S)-methylpentyloxy]-3-(1-naphthyl)propionyl-methionine sulfone Anal. Calcd for $C_{29}H_{39}N_3O_8S$·1.5 TFA: C, 50.52; H, 5.37; N, 5.52. Found: C, 50.50; H, 5.17; N, 5.54.

2(S)-[2(S)-(Imidazol-4-ylacetylamino)-3(S)-methylpentyloxy]-3-(1-naphthyl)propionyl-methionine sulfone Anal. Calcd for $C_{29}H_{38}N_4O_7S$·2 TFA·0.60 $H_2O$: C, 48.01; H, 5.03; N, 6.79. Found: C, 47.99; H, 5.02; N, 7.01.

2(S)-[2(S)-(L-Pyroglutamylamino)-3(S)-methylpentyloxy]-3-(2-naphthyl)propionyl-methionine sulfone Anal. Calcd for $C_{29}H_{39}N_3O_8S$·1.55 TFA·0.15 $H_2O$: C, 50.13; H, 5.35; N, 5.46. Found: C, 50.12; H, 5.34; N, 5.60.

2(S)-[2(S)-(Imidazol-4-ylacetyl)amino-3(S)-methylpentyloxy]-3-(2-naphthyl)propionyl-methionine sulfone Anal. Calcd for $C_{29}H_{38}N_4O_7S$·1.2 TFA·1.25 $H_2O$: C, 50.55; H, 5.63; N, 7.51. Found: C, 50.54; H, 5.62; N, 7.22.

N-(Benzyl)-N-[2(S)-(tetrazol-1-ylacetyl)amino-3(S)-methylpentyl]-glycyl-methionine Anal. Calcd for $C_{23}H_{35}N_7O_4S$·1.35 TFA·0.45 $H_2O$: C, 46.23; H, 5.62; N, 14.69. Found: C, 46.24; H, 5.61; N, 14.66.

N-(Benzyl)-N-[2(S)-nicotinoylamino-3(S)-methylpentyl]-glycyl-methionine

Anal. Calcd for $C_{26}H_{36}N_4O_4S$·1.9 TFA: C, 49.89; H, 5.33; N, 7.81. Found: C, 49.69; H, 5.67; N, 8.15.

N-[2(S)-(L-pyroglutamyl)amino-3(S)-methylpentyl]-N-(4-quinolylmethyl)glycyl-methionine Anal. Calcd for $C_{28}H_{39}N_5O_5S$·1.9 TFA: C, 49.32; H, 5.32; N, 9.04. Found: C, 49.34; H, 5.70; N, 9.23.

N-{2(S)-[(Imidazol-4-yl)methyl]amino-3(S)-methylpentyl}-N-(1-naphthylmethyl)glycyl-methionine FAB MS m/z=526 (M+1).

N-{2(S)-[3-(Imidazol-4-yl)propyl]amino-3(S)-methylpentyl}-N-(1-naphthylmethyl)glycyl-methionine Anal. Calcd for $C_{30}H_{43}N_5O_3S$·3 TFA·0.8 $H_2O$: C, 47.50; H, 5.27; N, 7.69. Found: C, 47.48; H, 5.27; N, 7.76.

N-[2(S)-(L-pyroglutamyl)amino-3(S)-methylpentyl]-N-(1-naphthylmethyl)glycyl-norleucine Anal. Calcd for $C_{30}H_{42}N_4O_5$·1.5 TFA: C, 55.84; H, 6.18; N, 7.89. Found: C, 55.74; H, 6.42; N, 8.12.

N-[2(S)-(L-pyroglutamyl)amino-3(S)-methylpentyl]-N-(1-naphthylmethyl)glycyl-glutamine Anal. Calcd for $C_{29}H_{39}N_5O_6$·1.75 TFA: C, 51.82; H, 5.45; N, 9.30. Found: C, 51.89; H, 5.73; N, 9.58.

N-[2(S)-(3-pyridylmethyl)amino-3(S)-methylpentyl]-N-(1-naphthylmethyl)glycyl-methionine Anal. Calcd for $C_{30}H_{40}N_4O_3S$·2.8 TFA·0.25 $H_2O$: C, 49.69; H, 5.07; N, 6.51. Found: C, 49.66; H, 5.05; N, 6.64.

N-[2(S)-(L-pyroglutamyl)amino-3(S)-methylpentyl]-N-(1-naphthylmethyl)glycyl-homoserine This compound was prepared by in sire hydrolysis of the corresponding lactone.

N-[2(S)-(L-pyroglutamyl)amino-3(S)-methylpentyl]-N-(1-naphthylmethyl)glycyl-(D,L)-serine FAB MS m/z=513 (M+1).

N-[2(S)-(L-pyroglutamyl)amino-3(S)-methylpentyl]-N-(1-naphthylmethyl)glycyl-(L,D)-serine FAB MS m/z=513 (M+1).

N-[2(S)-(L-pyroglutamyl)amino-3(S)-methylpentyl]-N-(cinnamyl)glycyl-methionine $^1$H NMR of this compound was consistent with the proposed structure.

2(S)-{2(S)-[2-(Imidazol-4-yl)ethyl]amino-3(S)-methylpentyloxy}-3-phehenylpropionyl-methionine sulfone FAB MS m/z=523 (M+1).

N-{2(S)-[2-(Imidazol-4-yl)ethyl]amino-3(S)-methylpentyl}-N-(1-naphthylmethyl)glycyl-methionine Anal. Calcd for $C_{29}H_{41}N_5O_3S.2.35$ TFA: C, 50.11; H, 5.41; N, 8.67. Found: C, 50.19; H, 5.42; N, 8.59.

N-[2(S)-(L-pyroglutamyl)amino-3(S)-methylpentyl]-N-(1-naphthylmethyl)glycyl-alanine FAB MS m/z=497 (M+1).

N-[2(S)-(D-pyroglutamyl)amino-3(S)-methylpentyl]-N-(1-naphthylmethyl)glycyl-methionine Anal. Calcd for $C_{29}H_{40}N_4O_5S.TFA.H_2O$: C, 54.05; H, 6.29; N, 8.14. Found: C, 53.77; H, 6.18; N, 8.11.

2(S)-[2(S)-(L-Pyroglutamyl)amino-3(S)-methylpentyloxy]-3-phenylpropionyl-methionine sulfone Anal. Calcd for $C_{25}H_{37}N_3O_8S.0.65$ TFA.0.15 $H_2O$: C, 51.24; H, 6.21; N, 6.82. Found: C, 51.23; H, 6.22; N, 6.97.

N-[2(S)-(L-pyroglutamyl)amino-3(S)-methylpentyl]-N-(2,3-methylenedioxybenzyl)glycyl-methionine Anal. Calcd for $C_{26}H_{38}N_4O_7S.2.1$ TFA: C, 45.90; H, 5.12; N, 7.09. Found: C, 45.84; H, 5.29; N, 7.43.

N-[2(S)-(Imidazol-4-ylacetyl)amino-3(S)-methylpentyl]-N-(2,3-dihydrobenzofuran-7-ylmethyl)glycyl-methionine FAB MS m/z=546 (M+1).

N-{2(S)-[3-(3-indolyl)propionyl]amino-3(S)-methylpentyl}-N-(1-naphthylmethyl)glycyl-methionine Anal. Calcd for $C_{35}H_{44}N_4O_4S.0.4$ EtOAc.0.75 $H_2O$: C, 66.04; H, 7.38; N, 8.42. Found: C, 66.03; H, 7.15; N, 8.41.

N-{2(S)-[3-(1-indolyl)propionyl]amino-3(S)-methylpentyl}-N-(1-naphthylmethyl)glycyl-methionine Anal. Calcd for $C_{35}H_{44}N_4O_4S.0.8$ EtOAc.0.85 $H_2O$: C, 65.30; H, 7.47; N, 7.97. Found: C, 65.26; H, 7.11; N, 7.97.

N-[2(S)-(L-pyroglutamyl)amino-3(S)-methylpentyl]-N-(1-naphthylmethyl)glycyl-histidine FAB MS m/z=562 (M+1).

N-[2(S)-(L-pyroglutamyl)amino-3(S)-methylpentyl]-N-(cyclopropylmethyl)glycyl-methionine Anal. Calcd for $C_{22}H_{38}N_4O_5S.1.75$ TFA.0.45 $H_2O$: C, 45.16; H, 6.04; N, 8.26. Found: C, 45.12; H, 6.03; N, 8.59.

N-[2(S)-(Imidazol-4-ylacetyl)amino-3(S)-methylpentyl]-N-(cyclopropylmethyl)glycyl-methionine FAB MS m/z=468 (M+1).

N-[2(S)-(L-pyroglutamyl)amino-3(S)-methylpentyl]-N-(2,3-dihydrobenzofuran-7-ylmethyl)glycyl-methionine FAB MS m/z=549 (M+1).

2(S)-[2(S)-N-(L-Pyroglutamyl)-N-methylamino-3(S)-methylpentyloxy]-3-phenylpropionyl-methionine sulfone Anal. Calcd for $C_{25}H_{37}N_3O_6S$: C, 51.24; H, 6.21; N, 6.82. Found: C, 51.23; H, 6.22; N, 6.97.

N-[2(S)-(L-pyroglutamyl)amino-3(S)-methylpentyl]-N-(1-naphthylmethyl)glycyl-O-methylserine Anal. Calcd for $C_{29}H_{40}N_4O_6$: C, 62.34; H, 7.58; N, 10.01. Found: C, 61.86; H, 7.06; N, 10.00.

N-(1-Naphthylmethyl)-N-[2(S)-(N'-(L-pyroglutamyl)-N'-methylamino)-3(S)-methylpentyl]-glycyl-methionine FAB MS m/z=571 (M+1).

N-[1-(Pyroglutamylamino)-cyclopent-1-ylmethyl]-N-(1-naphthylmethyl)glycyl-methionine FAB MS m/z=554 (M+1).

N-[2(S)-(Pyridin-2-on-6-ylcarbonyl)amino-3(S)-methylpentyl]-N-(1-naphthylmethyl)glycyl-methionine This compound was prepared by in situ hydrolysis of the corresponding methyl ester.

EXAMPLE 36

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et at., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of farnesyl in the presence of the test compound when compared to the amount of incorporation in the absence of the test compound.

Human FPTase was prepared as described by Omer et at., *Biochemistry* 32:5167–5176 (1993). Human FPTase activity was assayed as described above with the exception that 0.1% (w/v) polyethylene glycol 20,000, 10 μm $ZnCl_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have $IC_{50}$ of <10 μM.

EXAMPLE 37

In vivo ras farnesylation assay

The cell line used in this assay is a v-ras line derived from either Rat1 or NIH3T3 cells, which expressed viral Ha-ras p21. The assay is performed essentially as described in DeClue, J.E. et at., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000× g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M.E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 38

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits Ras farnesyl-transferase having the formula I:

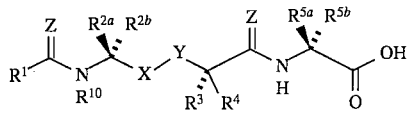

wherein:

$R^1$ is selected from:
 a) heterocycle, and
 b) $C_1$–$C_{10}$ alkyl, which is substituted with heterocycle and which is optionally substituted with one or more of $C_1$–$C_4$ alkyl, hydroxy or amino groups;

$R^{2a}$ and $R^{2b}$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted $C_1$–$C_{20}$ alkyl, $C_2$–$C_{20}$ alkenyl, $C_3$–$C_{10}$ cycloalkyl, aryl or heterocyclic group,
  wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
 d) $C_1$–$C_6$ alkyl substituted with an unsubstituted or substituted group selected from aryl, heterocycle and

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa  Val  Phe  Met
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Xaa  Val  Ile  Met
1

$C_3-C_{10}$ cycloalkyl; or $R^{2a}$ and $R^{2b}$ are combined to form $-(CH_2)_s-$;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1-C_{20}$ alkyl, $C_2-C_{20}$ alkenyl, $C_3-C_{10}$ cycloalkyl, aryl or heterocyclic group,
    wherein the substituent is selected from F, Cl, Br, $N(R^8)_2$, $NO_2$, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1-C_{20}$ alkyl, and
  d) $C_1-C_6$ alkyl substituted with an unsubstituted or substituted group selected from aryl, heterocyclic and $C_3-C_{10}$ cycloalkyl; or
  $R^3$ and $R^4$ are combined to form $-(CH_2)_s-$;

$R^{5a}$ and $R^{5b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1-C_{20}$ alkyl, $C_2-C_{20}$ alkenyl, $C_3-C_{10}$ cycloalkyl, aryl or heterocycle group,
    wherein the substituent is selected from F, Cl, Br, $N(R^8)_2$, $NO_2$, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1-C_{20}$ alkyl, and
  d) $C_1-C_6$ alkyl substituted with an unsubstituted or substituted group selected from aryl, heterocyclic and $C_3-C_{10}$ cycloalkyl; or
  $R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^8)-$;

X-Y is
a)
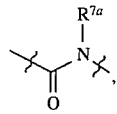

b)
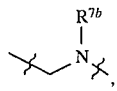

c)
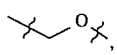

d)
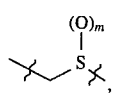

e)
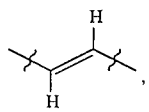

or
f) $-CH_2-CH_2-$;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1-C_6$ alkyl substituted with hydrogen or an unsubstituted or substituted group selected from aryl, heterocyclic and cycloalkyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1-C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;

$R^8$ is independently selected from hydrogen, $C_1-C_6$ alkyl and aryl;

$R^9$ is independently selected from $C_1-C_6$ alkyl and aryl;

$R^{10}$ is independently selected from hydrogen and $C_1-C_6$ alkyl;

Z is independently $H_2$ or O;

m is 0, 1 or 2; and s is 4 or 5;

or a pharmaceutically acceptable salt thereof.

2. A prodrug of a compound of claim 1 having the formula II:

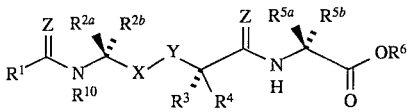

wherein:
$R^1$ is selected from:
  a) heterocycle, and
  b) $C_1-C_{10}$ alkyl, which is substituted with heterocycle and which is optionally substituted with one or more of $C_1-C_4$ alkyl, hydroxy or amino groups;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and d) C$_1$–C$_6$ alkyl substituted with an unsubstituted or substituted group selected from aryl, heterocycle and C$_3$–C$_{10}$ cycloalkyl; or R$^{2a}$ and R$^{2b}$ are combined to form —(CH$_2$)$_s$—;

R$^3$ and R$^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted C$_1$–C$_{20}$ alkyl, C$_2$–C$_{20}$ alkenyl, C$_3$–C$_{10}$ cycloalkyl, aryl or heterocyclic group,
     wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
  d) C$_1$–C$_6$ alkyl substituted with an unsubstituted or substituted group selected from aryl, heterocyclic and C$_3$–C$_{10}$ cycloalkyl; or
  R$^3$ and R$^4$ are combined to form —(CH$_2$)$_s$—;

R$^{5a}$ and R$^{5b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted C$_1$–C$_{20}$ alkyl, C$_2$–C$_{20}$ alkenyl, C$_3$–C$_{10}$ cycloalkyl, aryl or heterocycle group,
     wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
  d) C$_1$–C$_6$ alkyl substituted with an unsubstituted or substituted group selected from aryl, heterocyclic and C$_3$–C$_{10}$ cycloalkyl; or
  R$^{5a}$ and R$^{5b}$ are combined to form —(CH$_2$)$_s$— wherein one of the carbon atoms is optionally replaced by a moiety selected from: O, S(O)$_m$, —NC(O)—, and —N(COR$^8$)—;

R$^6$ is
  a) substituted or unsubstituted C$_1$–C$_8$ alkyl, wherein the substituent on the alkyl is selected from:
    1) aryl,
    2) heterocycle,
    3) —N(R$^9$)$_2$,
    4) —OR$^8$, or
  b)
  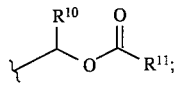

X-Y is
  a) 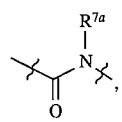
  b) 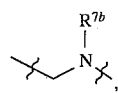
  c) 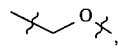
  d) 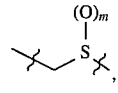
  e) 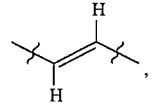

or
  f) —CH$_2$—CH$_2$—;

R$^{7a}$ is selected from
  a) hydrogen,
  b) unsubstituted or substituted aryl,
  c) unsubstituted or substituted heterocyclic,
  d) unsubstituted or substituted cycloalkyl, and
  e) C$_1$–C$_6$ alkyl substituted with hydrogen or an unsubstituted or substituted group selected from aryl, heterocyclic and cycloalkyl;

R$^{7b}$ is selected from
  a) hydrogen,
  b) unsubstituted or substituted aryl,
  c) unsubstituted or substituted heterocyclic,
  d) unsubstituted or substituted cycloalkyl,
  e) C$_1$–C$_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;

R$^8$ is independently selected from hydrogen, C$_1$–C$_6$ alkyl and aryl;

R$^9$ is independently selected from C$_1$–C$_6$ alkyl and aryl;

R$^{10}$ is independently selected from hydrogen and C$_1$–C$_6$ alkyl;

R$^{11}$ is independently selected from C$_1$–C$_6$ alkyl;

Z is independently $H_2$ or O;

m is 0, 1 or 2; and s is 4 or 5;

or a pharmaceutically acceptable salt thereof.

3. A compound which inhibits Ras farnesyl-transferase having the formula III:

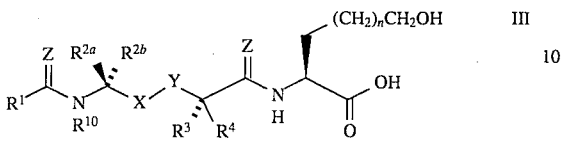

wherein:

$R^1$ is selected from:
  a) heterocycle, and
  b) $C_1$–$C_{10}$ alkyl, which is substituted with heterocycle and which is optionally substituted with one or more of $C_1$–$C_4$ alkyl, hydroxy or amino groups;

$R^{2a}$ and $R^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocycle and $C_3$–$C_{10}$ cycloalkyl; or
  $R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, $C_2$–$C_{20}$ alkenyl, $C_3$–$C_{10}$ cycloalkyl, aryl or heterocyclic group,
    wherein the substituent is selected from F, Cl, Br, $N(R^8)_2$, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl; or
  $R^3$ and $R^4$ are combined to form —$(CH_2)_s$—;

X-Y is
  a)
  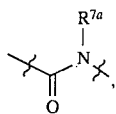

b)
  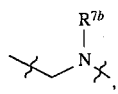

c)
  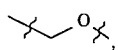

d)
  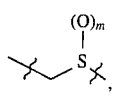

e)
  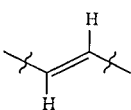

or
  f) —$CH_2$—$CH_2$—;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1$–$C_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;

$R^8$ is independently selected from hydrogen, $C_1$–$C_6$ alkyl and aryl;

$R^9$ is independently selected from $C_1$–$C_6$ alkyl and aryl;

$R^{10}$ is independently selected from hydrogen and $C_1$–$C_6$ alkyl;

Z is $H_2$ or O;

m is 0, 1 or 2 n is 0, 1 or 2; and s is 4 or 5 or a pharmaceutically acceptable salt thereof.

4. A prodrug of a compound of claim 3 of the formula IV:

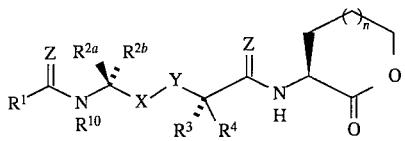      IV wherein:
R$^1$ is selected from:
  a) heterocycle, and
  b) C$_1$–C$_{10}$ alkyl, which is substituted with heterocycle and which is optionally substituted with one or more of C$_1$–C$_4$ alkyl, hydroxy or amino groups;
R$^{2a}$ and R$^{2b}$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted C$_1$–C$_{20}$ alkyl, C$_2$–C$_{20}$ alkenyl, C$_3$–C$_{10}$ cycloalkyl, aryl or heterocyclic group,
    wherein the substituent is selected from F, Cl, Br, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
  d) C$_1$–C$_6$ alkyl substituted with an unsubstituted or substituted group selected from aryl, heterocycle and C$_3$–C$_{10}$ cycloalkyl; or
  R$^{2a}$ and R$^{2b}$ are combined to form —(CH$_2$)$_s$—;
R$^3$ and R$^4$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted C$_1$–C$_{20}$ alkyl, C$_2$–C$_{20}$ alkenyl, C$_3$–C$_{10}$ cycloalkyl, aryl or heterocyclic group,
    wherein the substituent is selected from F, Cl, Br, N(R$^8$)$_2$, NO$_2$, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, R$^9$OC(O)NR$^8$— and C$_1$–C$_{20}$ alkyl, and
  d) C$_1$–C$_6$ alkyl substituted with an unsubstituted or substituted group selected from aryl, heterocyclic and C$_3$–C$_{10}$ cycloalkyl; or
  R$^3$ and R$^4$ are combined to form —(CH$_2$)$_s$—;
X-Y is
  a)
  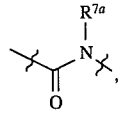

b)
  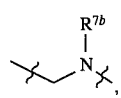

c)
  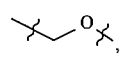

d)
  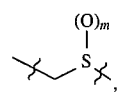

e)
  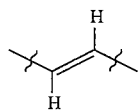

or
  f) —CH$_2$—CH$_2$—;
R$^{7a}$ is selected from
  a) hydrogen,
  b) unsubstituted or substituted aryl,
  c) unsubstituted or substituted heterocyclic,
  d) unsubstituted or substituted cycloalkyl, and
  e) C$_1$–C$_6$ alkyl substituted with hydrogen or an unsubstituted or substituted group selected from aryl, heterocyclic and cycloalkyl;
R$^{7b}$ is selected from
  a) hydrogen,
  b) unsubstituted or substituted aryl,
  c) unsubstituted or substituted heterocyclic,
  d) unsubstituted or substituted cycloalkyl,
  e) C$_1$–C$_6$ alkyl substituted with hydrogen or an unsubstituted or substituted group selected from aryl, heterocyclic and cycloalkyl,
  f) a carbonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl, and
  g) a sulfonyl group which is bonded to an unsubstituted or substituted group selected from aryl, heterocyclic, cycloalkyl and C$_1$–C$_6$ alkyl substituted with hydrogen or an unsubstituted or substituted group selected from aryl, heterocyclic and cycloalkyl;
R$^8$ is independently selected from hydrogen, C$_1$–C$_6$ alkyl and aryl;
R$^9$ is independently selected from C$_1$–C$_6$ alkyl and aryl;
R$^{10}$ is independently selected from hydrogen and C$_1$–C$_6$ alkyl;
Z is H$_2$ or O;
m is 0, 1 or 2;
n is 0, 1 or 2; and
s is 4 or 5;
or a pharmaceutically acceptable salt thereof.

5. The compound according to claim 1 having the formula I:

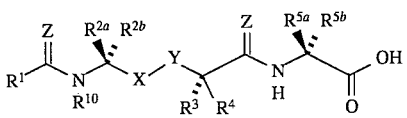      I wherein:
R$^1$ is selected from:

a) heterocycle selected from pyrrolidinyl, imidazolyl, pyridinyl, thiazolyl, pyridonyl, 2-oxopiperidinyl, indolyl, quinolinyl, and isoquinolinyl, and b) $C_1$–$C_{10}$ alkyl, which is substituted with a heterocycle and which is optionally substituted with one or more of $C_1$–$C_4$ alkyl, hydroxy or amino groups;
wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
a) a side chain of a naturally occurring amino acid, wherein the amino acid is selected from alanine, leucine, isoleucine and valine;
b) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$, $C_1$–$C_{20}$ alkyl, and
c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or $R^{2a}$ and $R^{2b}$ are combined to form $-(CH_2)_s-$;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$, $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

$R^{5a}$ is selected from:
a) a side chain of a naturally occurring amino acid, wherein the amino acid is selected from methionine and glutamine,
b) an oxidized form of a side chain of a naturally occurring amino acid which is:
i) methionine sulfoxide, or
ii) methionine sulfone, and
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, $R^9OC(O)NR^8-$ and $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

$R^{5b}$ is selected from:
a) hydrogen, and
b) $C_1$–$C_3$ alkyl;

X-Y is
a)
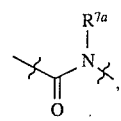

b)
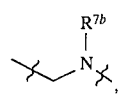

c)
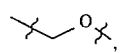

d)
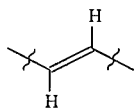

or
e) $-CH_2-CH_2-$;

$R^{7a}$ is selected from
a) hydrogen,
b) unsubstituted or substituted aryl,
c) unsubstituted or substituted heterocyclic,
d) unsubstituted or substituted cycloalkyl, and
e) $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

Z is independently $H_2$ or O;

m is 0, 1 or 2; and s is 4 or 5;
or a pharmaceutically acceptable salt thereof.

6. The compound according to claim 2 having the formula II:

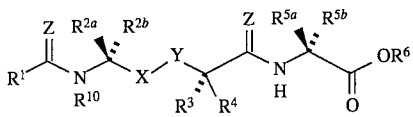

wherein:
$R^1$ is selected from:
  a) heterocycle selected from pyrrolidinyl, imidazolyl, pyridinyl, thiazolyl, pyridonyl, 2-oxopiperidinyl, indolyl, quinolinyl, and isoquinolinyl, and
  b) $C_1$–$C_{10}$ alkyl, which is substituted with a heterocycle and which is optionally substituted with one or more of $C_1$–$C_4$ alkyl, hydroxy or amino groups;
    wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
  a) a side chain of a naturally occurring amino acid, wherein the amino acid is selected from alanine, leucine, isoleucine and valine; and
  b) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or
$R^{2a}$ and $R^{2b}$ are combined to form —$(CH_2)_s$—;

$R^3$ and $R^4$ are independently selected from:
  a) a side chain of a naturally occurring amino acid,
  b) an oxidized form of a side chain of a naturally occurring amino acid which is:
    i) methionine sulfoxide, or
    ii) methionine sulfone,
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl;

$R^{5a}$ is selected from:
  a) a side chain of a naturally occurring amino acid, wherein the amino acid is selected from methionine and glutamine,
  b) an oxidized form of a side chain of a naturally occurring amino acid which is:
    i) methionine sulfoxide, or
    ii) methionine sulfone, and
  c) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
  d) $C_1$–$C_6$ alkyl substituted with an unsubstituted or substituted group selected from aryl, heterocyclic and $C_3$–$C_{10}$ cycloalkyl;

$R^{5b}$ is selected from:
  a) hydrogen, and
  b) $C_1$–$C_3$ alkyl;

$R^6$ is
  a) substituted of unsubstituted $C_1$–$C_8$ alkyl, wherein the substituent on the alkyl is selected from:
    1) aryl,
    2) heterocycle,
    3) —$N(R^9)_2$,
    4) —$OR^8$, or
  b)

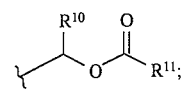

X-Y is
  a)

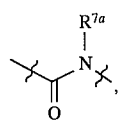

b)

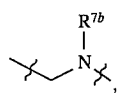

c)

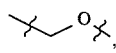

d)

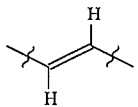

e) —$CH_2$—$CH_2$—;

$R^{7a}$ is selected from
  a) hydrogen,
  b) unsubstituted or substituted aryl,
  c) unsubstituted or substituted heterocyclic,
  d) unsubstituted or substituted cycloalkyl, and
  e) $C_1$–$C_6$ alkyl substituted with hydrogen or an unsubstituted or substituted group selected from aryl, heterocyclic and cycloalkyl;
    wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
  a) hydrogen,
  b) unsubstituted or substituted aryl,
  c) unsubstituted or substituted heterocyclic,
  d) unsubstituted or substituted cycloalkyl,
  e) $C_1$–$C_6$ alkyl substituted with hydrogen or an unsubstituted or substituted group selected from aryl, heterocyclic and cycloalkyl, f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1-C_6$ alkyl and aryl;

$R^9$ is independently selected from $C_1-C_6$ alkyl and aryl;

$R^{10}$ is independently selected from hydrogen and $C_1-C_6$ alkyl;

$R^{11}$ is independently selected from $C_1-C_6$ alkyl;

Z is independently $H_2$ or O;

m is 0, 1 or 2; and s is 4 or 5;

or a pharmaceutically acceptable salt thereof.

7. The compound according to claim 3 having the formula III:

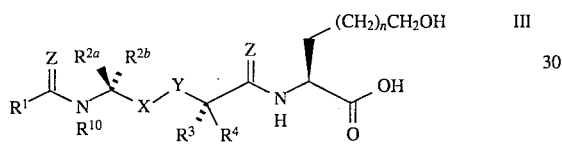

wherein:

$R^1$ is selected from:

a) heterocycle selected from pyrrolidinyl, imidazolyl, pyridinyl, thiazolyl, pyridonyl, 2-oxopiperidinyl, indolyl, quinolinyl, and isoquinolinyl, and b) $C_1-C_{10}$ alkyl, which is substituted with a heterocycle and which is optionally substituted with one or more of $C_1-C_4$ alkyl, hydroxy or amino groups;

wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:

a) a side chain of a naturally occurring amino acid, wherein the amino acid is selected from alanine, leucine, isoleucine and valine;

b) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1-C_{20}$ alkyl, and d) $C_1-C_6$ alkyl substituted with an unsubstituted or substituted group selected from aryl, heterocyclic and $C_3-C_{10}$ cycloalkyl;

$R^{2b}$ is selected from hydrogen and $C_1-C_6$ alkyl; or $R^{2a}$ and $R^{2b}$ are combined to form —$(CH_2)_s$—;

$R^3$ and $R^4$ are independently selected from:

a) a side chain of a naturally occurring amino acid, b) an oxidized form of a side chain of a naturally occurring amino acid which is:

i) methionine sulfoxide, or ii) methionine sulfone, c) substituted or unsubstituted $C_1-C_{10}$ alkyl, $C_2-C_{10}$ alkenyl, $C_3-C_{10}$ cycloalkyl, aryl or heterocyclic group, wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1-C_{20}$ alkyl, and d) $C_1-C_6$ alkyl substituted with an unsubstituted or substituted group selected from aryl, heterocyclic and $C_3-C_{10}$ cycloalkyl;

X-Y is a) 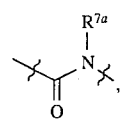

b) 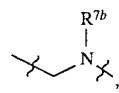

c) 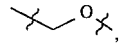

d) 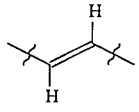

or e) —$CH_2$—$CH_2$—;

$R^{7a}$ is selected from a) hydrogen, b) unsubstituted or substituted aryl, c) unsubstituted or substituted heterocyclic, d) unsubstituted or substituted cycloalkyl, and e) $C_1-C_6$ alkyl substituted with hydrogen or an unsubstituted or substituted group selected from aryl, heterocyclic and cycloalkyl;

wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from a) hydrogen, b) unsubstituted or substituted aryl, c) unsubstituted or substituted heterocyclic, d) unsubstituted or substituted cycloalkyl, e) $C_1-C_6$ alkyl substituted with hydrogen or an unsubstituted or substituted group selected from aryl, heterocyclic and cycloalkyl, f) a carbonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl, and g) a sulfonyl group which is bonded to an unsubstituted or substituted group selected from aryl, heterocyclic, cycloalkyl and $C_1-C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

Z is independently $H_2$ or O;

m is 0, 1 or 2;

n is 0, 1 or 2; and s is 4 or 5;

or a pharmaceutically acceptable salt thereof.

8. The compound according to claim 4 having the formula IV:

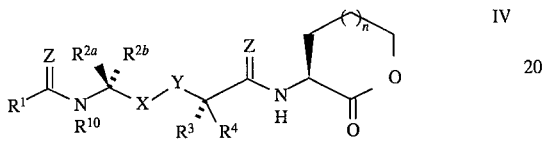

wherein:

$R^1$ is selected from:
a) heterocycle selected from pyrrolidinyl, imidazolyl, pyridinyl, thiazolyl, pyridonyl, 2-oxopiperidinyl, indolyl, quinolinyl, and isoquinolinyl, and
b) $C_1$–$C_{10}$ alkyl, which is substituted with a heterocycle and which is optionally substituted with one or more of $C_1$–$C_4$ alkyl, hydroxy or amino groups;
wherein the heterocycle is selected from pyrrolidinyl, imidazolyl, pyridinyl, thiazolyl, pyridonyl, 2-oxopiperidinyl, indolyl, quinolinyl, and isoquinolinyl;

$R^{2a}$ is selected from:
a) a side chain of a naturally occurring amino acid, wherein the amino acid is selected from alanine, leucine, isoleucine and valine;
b) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$— and $C_1$–$C_{20}$ alkyl, and
c) $C_1$–$C_6$ alkyl substituted with an unsubstituted or substituted group selected from aryl, heterocyclic and $C_3$–$C_{10}$ cycloalkyl;

$R^{2b}$ is selected from hydrogen and $C_1$–$C_6$ alkyl; or $R^{2a}$ and $R^{2b}$ are combined to form —$(CH_2)_s$—;

$R^3$ and $R^4$ are independently selected from:
a) a side chain of a naturally occurring amino acid,
b) an oxidized form of a side chain of a naturally occurring amino acid which is:
i) methionine sulfoxide, or
ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
wherein the substituent is selected from F, Cl, Br, $NO_2$, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, $R^9OC(O)NR^8$—, $C_1$–$C_{20}$ alkyl, and
d) $C_1$–$C_6$ alkyl substituted with an unsubstituted or substituted group selected from aryl, heterocyclic and $C_3$–$C_{10}$ cycloalkyl;

X-Y is
a)

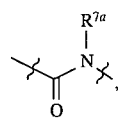

b)

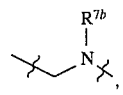

c)

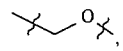

d)

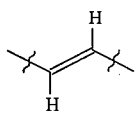

or
e) —$CH_2$—$CH_2$—;

$R^{7a}$ is selected from
a) hydrogen,
b) unsubstituted or substituted aryl,
c) unsubstituted or substituted heterocyclic,
d) unsubstituted or substituted cycloalkyl, and,
e) $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^{7b}$ is selected from
a) hydrogen,
b) unsubstituted or substituted aryl,
c) unsubstituted or substituted heterocyclic,
d) unsubstituted or substituted cycloalkyl,
e) $C_1$–$C_6$ alkyl substituted with hydrogen or an unsubstituted or substituted group selected from aryl, heterocyclic and cycloalkyl,
f) a carbonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl, and
g) a sulfonyl group which is bonded to an unsubstituted or substituted group selected from aryl, heterocyclic, cycloalkyl and $C_1$–$C_6$ alkyl substituted with hydrogen or an unsubstituted or substituted group selected from aryl, heterocyclic and cycloalkyl;
wherein heterocycle is selected from pyrrolidinyl, imidazolyl, pyridinyl, thiazolyl, pyridonyl, 2-oxopiperidinyl, indolyl, quinolinyl, isoquinolinyl, and thienyl;

$R^8$ is independently selected from hydrogen, $C_1$–$C_6$ alkyl and aryl;

$R^9$ is independently selected from $C_1$–$C_6$ alkyl and aryl;

Z is independently $H_2$ or O;

m is 0, 1 or 2;

n is 0, 1 or 2; and s is 4 or 5;

or a pharmaceutically acceptable salt thereof.

9. A compound which inhibits farnesyl-protein transferase which is:

Pyroglutamyl-valyl-isoleucyl-methionine;
Pyroglutamyl-valyl-isoleucyl-methionine methyl ester;
Nicotinoyl-isoleucyl-phenylalanyl-methionine;
Nicotinoyl-isoleucyl-phenylalanyl-methionine methyl ester;
N-[2(S)-(L-Pyroglutamylamino)-3-methylbutyl]phenylalanyl-methionine;
N-[2(S)-(L-Pyroglutamylamino)-3-methylbutyl]phenylalanyl-methionine methyl ester;
N-[5(S)-(L-Pyroglutamylamino)-6(S)-methyl-2(R)-butyl-3,4(E)-octenoyl]-methionine;
N-[5(S)-(L-Pyroglutamylamino)-6(S)-methyl-2(R)-butyl-3,4(E)-octenoyl]-methionine methyl ester;
N-[5(S)-((Imidazol-4-yl)acetylamino)-6(S)-methyl-2(R)-butyl-3,4(E)-octenoyl]-methionine;
N-[5(S)-((Imidazol-4-yl)acetylamino)-6(S)-methyl-2(R)-butyl-3,4(E)-octenoyl]-methionine methyl ester;
N-[5(S)-((Imidazol-4-ylcarbonylamino)-6(S)-methyl-2(R)-butyl-3,4(E)-octenoyl]-methionine;
N-[5(S)-((Imidazol-4-ylcarbonylamino)-6(S)-methyl-2(R)-butyl-3,4(E)-octenoyl]-methionine methyl ester;
N-[2(S)-(2(S)-(Imidazol-4-yl)acetylamino)-3(S)-methylpentyloxy)-3-phenylpropionyl]-methionine;
N-[2(S)-(2(S)-(Imidazol-4-yl)acetylamino)-3(S)-methylpentyloxy)-3-phenylpropionyl]-methionine methyl ester;
N-[2(S)-(2(S)-Pyroglutamylamino-3(S)-methylpentyloxy)-3-phenylpropionyl]-methionine;
N-[2(S)-(2(S)-Pyroglutamylamino-3(S)-methylpentyloxy)-3-phenylpropionyl]-methionine methyl ester;
N-[2(S)-(2(S)-Imidazol-4-ylcarbonyl)amino)-3(S)-methylpentyloxy)-3-phenylpropionyl]-methionine;
N-[2(S)-(2(S)-Imidazol-4-ylcarbonyl)amino)-3(S)-methylpentyloxy)-3-phenylpropionyl]-methionine methyl ester;
N-[2(S)-(2(S)-((3-Picolinyl)amino)-3(S)-methylpentyloxy)-3-phenylpropionyl]-methionine;
N-[2(S)-(2(S)-((3-Picolinyl)amino)-3(S)-methylpentyloxy)-3-phenylpropionyl]-methionine methyl ester;
N-[2(S)-(2(S)-((Histidyl)amino)-3(S)-methylpentyloxy)-3-phenylpropionyl]-methionine;
N-[2(S)-(2(S)-((Histidyl)amino)-3(S)-methylpentyloxy)-3-phenylpropionyl]-methionine methyl ester;
N-Benzyl-N-[2(S)-((Imidazol-4-ylcarbonyl)amino)-3(S)-methylpentyl]-glycyl-methionine;
N-Benzyl-N-[2(S)-((Imidazol-4-ylcarbonyl)amino)-3(S)-methylpentyl]-glycyl-methionine methyl ester;
N-Benzyl-N-[2(S)-((Imidazol-4-ylacetyl)amino)-3(S)-methylpentyl]-glycyl-methionine;
N-Benzyl-N-[2(S)-((Imidazol-4-ylacetyl)amino)-3(S)-methylpentyl]-glycyl-methionine methyl ester;
N-Benzyl-N-[2(S)-((Pyroglutamyl)amino)-3(S)-methylpentyl]-glycyl-methionine;
N-Benzyl-N-[2(S)-((Pyroglutamyl)amino)-3(S)-methylpentyl]-glycyl-methionine methyl ester;
N-(1-Naphthylmethyl)-N-[2(S)-((imidazol-4-ylcarbonyl)amino)-3(S)-methylpentyl]-glycyl-methionine;
N-(1-Naphthylmethyl)-N-[2(S)-((imidazol-4-ylcarbonyl)amino)-3(S)-methylpentyl]-glycyl-methionine methyl ester;
N-(1-Naphthylmethyl)-N-[2(S)-((imidazol-4-ylacetyl)amino)-3(S)-methylpentyl]-glycyl-methionine;
N-(1-Naphthylmethyl)-N-[2(S)-((imidazol-4-ylacetyl)amino)-3(S)-methylpentyl]-glycyl-methionine methyl ester;
N-(1-Naphthylmethyl)-N-[2(S)-((pyroglutamyl)amino)-3(S)-methylpentyl]-glycyl-methionine;
N-(1-Naphthylmethyl)-N-[2(S)-((pyroglutamyl)amino)-3(S)-methylpentyl]-glycyl-methionine methyl ester;
N-[1-(Pyroglutamylamino)cyclopent-1-ylmethyl]-N-(1-naphthylmethyl)glycyl-methionine methyl ester;
N-[1-(Pyroglutamylamino)-cyclopent-1-ylmethyl]-N-(1-naphthylmethyl)glycyl-methionine;
N-(2(S)-L-Histidylamino-3(S)-methylpentyl)-N-(benzylmethyl)glycyl-methionine methyl ester;
N-(2(S)-L-Histidylamino-3(S)-methylpentyl)-N-(benzylmethyl)glycyl-methionine;
N-(2(S)-L-Histidylamino-3(S)-methylpentyl)-N-(1-naphthylmethyl)glycyl-methionine methyl ester;
N-(2(S)-L-Histidylamino-3(S)-methylpentyl)-N-(1-naphthylmethyl)glycyl-methionine;
2(S)-[2(S)-(L-Pyroglutamyl)amino-3(S)-methylpentyloxy]-3-methylbutanoyl-methionine methyl ester;
2(S)-[2(S)-(L-Pyroglutamyl)amino-3(S)-methylpentyloxy]-3-methylbutanoyl-methionine;
2(S)-[2(S)-(Imidazol-4-ylacetyl)amino-3(S)-methylpentyloxy]-3-methylbutanoyl-methionine methyl ester;
2(S)-[2(S)-(Imidazol-4-ylacetyl)amino-3(S)-methylpentyloxy]-3-methylbutanoyl-methionine;
N-(Benzyl)-N-[2(S)-(2-oxopyrrolidin-5(R,S)-ylmethyl)amino-3(S)-methylpentyl]-glycyl-methionine methyl ester;
N-(Benzyl)-N-[2(S)-(2-oxopyrrolidin-5(R,S)-ylmethyl)amino-3(S)-methylpentyl]-glycyl-methionine;
N-(Benzyl)-N-{2(S)-[((D,L)-2-thiazolyl)alanyl)amino]-3(S)-methylpentyl}-glycyl-methionine methyl ester;
N-(Benzyl)-N-{2(S)-[((D,L)-2-thiazolyl)alanyl)amino]-3(S)-methylpentyl}-glycyl-methionine;
N-(Benzyl)-N-[2(S)-(3-pyridylmethyl)amino-3(S)-methylpentyl]-glycyl-methionine methyl ester;
N-(Benzyl)-N-[2(S)-(3-pyridylmethyl)amino-3(S)-methylpentyl]-glycyl-methionine;
2(S)-[2(S)-(2-Oxopyrrolidin-5(S)-ylmethyl)amino-3(S)-methylpentyloxy]-3-phenylpropionyl-methionine methyl ester;
2(S)-[2(S)-(2-Oxopyrrolidin-5(S)-ylmethyl)amino-3(S)-methylpentyloxy]-3-phenylpropionyl-methionine;
2(S)-[2(S)-(L-Pyroglutamyl)amino-3(S)-methylpentyloxy]-3-(1-naphthyl)propionyl-methionine sulfone methyl ester;
2(S)-[2(S)-(L-Pyroglutamyl)amino-3(S)-methylpentyloxy]-3-(1-naphthyl)propionyl-methionine sulfone;
2(S)-[2(S)-(L-Pyroglutamyl)amino-3(S)-methylpentyloxy]-3-(2-naphthyl)propionyl-methionine sulfone methyl ester;
2(S)-[2(S)-(L-Pyroglutamyl)amino-3(S)-methylpentyloxy]-3-(2-naphthyl)propionyl-methionine sulfone;
2(S)-[2(S)-(Imidazol-4-ylacetyl)amino-3(S)-methylpentyloxy]-3-(1-naphthyl)propionyl-methionine sulfone methyl ester;
2(S)-[2(S)-(Imidazol-4-ylacetyl)amino-3(S)-methylpentyloxy]-3-(1-naphthyl)propionyl-methionine sulfone;
2(S)-[2(S)-(Imidazol-4-ylacetyl)amino-3(S)-methylpentyloxy]-3-(2-naphthyl)propionyl-methionine sulfone methyl ester;
2(S)-[2(S)-(Imidazol-4-ylacetyl)amino-3(S)-methylpentyloxy]-3-(2-naphthyl)propionyl-methionine sulfone;
N-(Benzyl)-N-[2(S)-(tetrazol-1-ylacetyl)amino-3(S)-methylpentyl]-glycyl-methionine methyl ester;
N-(Benzyl)-N-[2(S)-(tetrazol-1-ylacetyl)amino-3(S)-methylpentyl]-glycyl-methionine;
N-(Benzyl)-N-[2(S)-nicotinoylamino-3(S)-methylpentyl]-glycyl-methionine methyl ester;

N-(Benzyl)-N-[2(S)-nicotinoylamino-3(S)-methylpentyl]-glycyl-methionine;

N-[2(S)-(L-Pyroglutamyl)amino-3(S)-methylpentyl]-N-(1-naphthylmethyl)glycyl-methionine sulfoxide methyl ester;

N-[2(S)-(L-Pyroglutamyl)amino-3(S)-methylpentyl]-N-(1-naphthylmethyl)glycyl-methionine sulfoxide;

2(S)-{2(S)-[2(S,R)-(Imidazol-4-yl)-2-aminoacetyl)amino]-3(S)-methylpentyloxy}-3-phenylpropionyl-methionine sulfone methyl ester;

2(S)-{2(S)-[2(S,R)-(Imidazol-4-yl)-2-aminoacetyl)amino]-3(S)-methylpentyloxy}-3-phenylpropionyl-methionine sulfone;

2(S)-{2(S)-[2(R,S)-(Imidazol-4-yl)-2-aminoacetyl)amino]-3(S)-methylpentyloxy}-3-phenylpropionyl-methionine sulfone methyl ester;

2(S)-{2(S)-[2(R,S)-(Imidazol-4-yl)-2-aminoacetyl)amino]-3(S)-methylpentyloxy}-3-phenylpropionyl-methionine sulfone;

N-{2(S)-[2(S,R)-(Imidazol-4-yl)-2-aminoacetyl]amino-3(S)-methylpentyl}-N-(1-naphthylmethyl)glycyl-methionine methyl ester;

N-{2(S)-[2(S,R)-(Imidazol-4-yl)-2-aminoacetyl]amino-3(S)-methylpentyl}-N-(1-naphthylmethyl)glycyl-methionine;

N-{2(S)-[2(R,S)-(Imidazol-4-yl)-2-aminoacetyl]amino-3(S)-methylpentyl}-N-(1-naphthylmethyl)glycyl-methionine methyl ester;

N-{2(S)-[2(R,S)-(Imidazol-4-yl)-2-aminoacetyl]amino-3(S)-methylpentyl}-N-(1-naphthylmethyl)glycyl-methionine;

N-{2(S)-[(Imidazol-4-yl)methyl]amino-3(S)-methylpentyl}-N-(1-naphthylmethyl)glycyl-methionine methyl ester;

N-{2(S)-[(Imidazol-4-yl)methyl]amino-3(S)-methylpentyl}-N-(1-naphthylmethyl)glycyl-methionine;

N-[2(S)-(L-pyroglutamyl)amino-3(S)-methylpentyl]-N-(1-naphthylmethyl)glycyl-methionine isopropyl ester;

N-[2(S)-(L-pyroglutamyl)amino-3(S)-methylpentyl]-N-(1-naphthylmethyl)glycyl-methionine t-butyl ester;

N-[2(S)-(L-pyroglutamyl)amino-3(S)-methylpentyl]-N-(4-quinolylmethyl)glycyl-methionine methyl ester;

N-[2(S)-(L-pyroglutamyl)amino-3(S)-methylpentyl]-N-(4-quinolylmethyl)glycyl-methionine;

N-{2(S)-[3-(Imidazol-4-yl)propyl]amino-3(S)-methylpentyl}-N-(1-naphthylmethyl)glycyl-methionine methyl ester;

N-{2(S)-[3-(Imidazol-4-yl)propyl]amino-3(S)-methylpentyl}-N-(1-naphthylmethyl)glycyl-methionine;

N-[2(S)-(L-pyroglutamyl)amino-3(S)-methylpentyl]-N-(1-naphthylmethyl)glycyl-norleucine;

N-[2(S)-(L-pyroglutamyl)amino-3(S)-methylpentyl]-N-(1-naphthylmethyl)glycyl-norleucine methyl ester;

N-[2(S)-(L-pyroglutamyl)amino-3(S)-methylpentyl]-N-(1-naphthylmethyl)glycyl-glutamine;

N-[2(S)-(L-pyroglutamyl)amino-3(S)-methylpentyl]-N-(1-naphthylmethyl)glycyl-glutamine t-butyl ester;

N-[2(S)-(3-pyridylmethyl)amino-3(S)-methylpentyl]-N-(1-naphthylmethyl)glycyl-methionine methyl ester;

N-[2(S)-(3-pyridylmethyl)amino-3(S)-methylpentyl]-N-(1-naphthylmethyl)glycyl-methionine;

2(S)-{2(S)-[2-(Imidazol-4-yl)ethyl]amino-3(S)-methylpentyloxy}-3-phenylpropionyl-methionine sulfone methyl ester;

2(S)-{2(S)-[2-(Imidazol-4-yl)ethyl]amino-3(S)-methylpentyloxy}-3-phenylpropionyl-methionine sulfone;

N-[2(S)-(L-pyroglutamyl)amino-3(S)-methylpentyl]-N-(1-naphthylmethyl)glycyl-serine methyl ester;

N-[2(S)-(L-pyroglutamyl)amino-3(S)-methylpentyl]-N-(1-naphthylmethyl)glycyl-(D,L)-serine;

N-[2(S)-(L-pyroglutamyl)amino-3(S)-methylpentyl]-N-(1-naphthylmethyl)glycyl-(L,D)-serine;

N-[2(S)-(L-pyroglutamyl)amino-3(S)-methylpentyl]-N-(1-naphthylmethyl)glycyl-homoserine lactone;

N-[2(S)-(L-pyroglutamyl)amino-3(S)-methylpentyl]-N-(1-naphthylmethyl)glycyl-homoserine;

N-[2(S)-(L-pyroglutamyl)amino-3(S)-methylpentyl]-N-(cinnamyl)glycyl-methionine methyl ester;

N-[2(S)-(L-pyroglutamyl)amino-3(S)-methylpentyl]-N-(cinnamyl)glycyl-methionine;

N-{2(S)-[2-(Imidazol-4-yl)ethyl]amino-3(S)-methylpentyl}-N-(1-naphthylmethyl)glycyl-methionine methyl ester;

N-{2(S)-[2-(Imidazol-4-yl)ethyl]amino-3(S)-methylpentyl}-N-(1-naphthylmethyl)glycyl-methionine;

N-[2(S)-(L-pyroglutamyl)amino-3(S)-methylpentyl]-N-(1-naphthylmethyl)glycyl-alanine methyl ester;

N-[2(S)-(L-pyroglutamyl)amino-3(S)-methylpentyl]-N-(1-naphthylmethyl)glycyl-alanine;

N-[2(S)-(D-pyroglutamyl)amino-3(S)-methylpentyl]-N-(1-naphthylmethyl)glycyl-methionine methyl ester;

N-[2(S)-(D-pyroglutamyl)amino-3(S)-methylpentyl]-N-(1-naphthylmethyl)glycyl-methionine;

2(S)-[2(S)-(L-Pyroglutamyl)amino-3(S)-methylpentyloxy]-3-phenylpropionyl-methionine sulfone methyl ester;

2(S)-[2(S)-(L-Pyroglutamyl)amino-3(S)-methylpentyloxy]-3-phenylpropionyl-methionine sulfone;

N-[2(S)-(L-pyroglutamyl)amino-3(S)-methylpentyl]-N-(2,3-methylenedioxybenzyl)glycyl-methionine methyl ester;

N-[2(S)-(L-pyroglutamyl)amino-3(S)-methylpentyl]-N-(2,3-methylenedioxybenzyl)glycyl-methionine;

N-[2(S)-(Imidazol-4-ylacetyl)amino-3(S)-methylpentyl]-N-(2,3-dihydrobenzofuran-7-ylmethyl)glycyl-methionine methyl ester;

N-[2(S)-(Imidazol-4-ylacetyl)amino-3(S)-methylpentyl]-N-(2,3-dihydrobenzofuran-7-ylmethyl)glycyl-methionine;

N-{2(S)-[3-(3-indolyl)propionyl]amino-3(S)-methylpentyl}-N-(1-naphthylmethyl)glycyl-methionine methyl ester;

N-{2(S)-[3-(3-indolyl)propionyl]amino-3(S)-methylpentyl}-N-(1-naphthylmethyl)glycyl-methionine;

N-{2(S)-[3-(1-indolyl)propionyl]amino-3(S)-methylpentyl}-N-(1-naphthylmethyl)glycyl-methionine methyl ester;

N-{2(S)-[3-(1-indolyl)propionyl]amino-3(S)-methylpentyl}-N-(1-naphthylmethyl)glycyl-methionine;

N-[2(S)-(L-pyroglutamyl)amino-3(S)-methylpentyl]-N-(1-naphthylmethyl)glycyl-histidine methyl ester;

N-[2(S)-(L-pyroglutamyl)amino-3(S)-methylpentyl]-N-(1-naphthylmethyl)glycyl-histidine;

N-[2(S)-(L-pyroglutamyl)amino-3(S)-methylpentyl]-N-(cyclopropylmethyl)glycyl-methionine methyl ester;

N-[2(S)-(L-pyroglutamyl)amino-3(S)-methylpentyl]-N-(cyclopropylmethyl)glycyl-methionine;

N-[2(S)-(Imidazol-4-ylacetyl)amino-3(S)-methylpentyl]-N-(cyclopropylmethyl)glycyl-methionine methyl ester;

N-[2(S)-(Imidazol-4-ylacetyl)amino-3(S)-methylpentyl]-N-(cyclopropylmethyl)glycyl-methionine;

N-[2(S)-(L-pyroglutamyl)amino-3(S)-methylpentyl]-N-(2,3-dihydrobenzofuran-7-ylmethyl)glycyl-methionine methyl ester;

N-[2(S)-(L-pyroglutamyl)amino-3(S)-methylpentyl]-N-(2,3-dihydrobenzofuran-7-ylmethyl)glycyl-methionine;

2(S)-[2(S)-N-(L-Pyroglutamyl)-N-methylamino-3(S)-methylpentyloxy]-3-phenylpropionyl-methionine methyl ester;

(S)-[2(S)-N-(L-Pyroglutamyl)-N-methylamino-3(S)-methylpentyloxy]-3-phenylpropionyl-methionine;

N-[2(S)-(L-pyroglutamyl)amino-3(S)-methylpentyl]-N-(1-naphthylmethyl)glycyl-O-methylserine methyl ester;

N-[2(S)-(L-pyroglutamyl)amino-3(S)-methylpentyl]-N-(1-naphthylmethyl)glycyl-O-methylserine;

N-(1-Naphthylmethyl)-N-[2(S)-(N'-(L-pyroglutamyl)-N'-methylamino)-3(S)-methylpentyl]-glycyl-methionine methyl ester;

N-(1-Naphthylmethyl)-N-[2(S)-(N'-(L-pyroglutamyl)-N'-methylamino)-3(S)-methylpentyl]-glycyl-methionine;

N-[1-(Pyroglutamylamino)cyclopent-1-ylmethyl]-N-(1-naphthylmethyl)glycyl-methionine methyl ester;

N-[1-(Pyroglutamylamino)-cyclopent-1-ylmethyl]-N-(1-naphthylmethyl)glycyl-methionine;

N-[2(S)-(Pyridin-2-on-6-ylcarbonyl)amino-3(S)-methylpentyl]-N-(1-naphthylmethyl)glycyl-methionine methyl ester;

N-[2(S)-(Pyridin-2-on-6-ylcarbonyl)amino-3(S)-methylpentyl]-N-(1-naphthylmethyl)glycyl-methionine;

N-[2(S)-(L-pyroglutamyl)amino-3(S)-methylpentyl]-N-(3-chlorobenzyl)glycyl-methionine methyl ester;

N-[2(S)-(L-pyroglutamyl)amino-3(S)-methylpentyl]-N-(3-chlorobenzyl)glycyl-methionine;

N-[2(S)-(L-pyroglutamyl)amino-3(S)-methylpentyl]-N-(1-naphthylmethyl)glycyl-O-methylhomoserine methyl ester;

N-[2(S)-(L-pyroglutamyl)amino-3(S)-methylpentyl]-N-(1-naphthylmethyl)glycyl-O-methylhomoserine;

N-[2(S)-(L-pyroglutamyl)amino-3(S)-methylpentyl]-N-(2,3-dimethylbenzyl)glycyl-methionine methyl ester;

N-[2(S)-(L-pyroglutamyl)amino-3(S)-methylpentyl]-N-(2,3-dimethylbenzyl)glycyl-methionine;

N-[2(S)-(L-pyroglutamyl)amino-3(S)-methylpentyl]-N-(1-naphthylmethyl)glycyl-(2-thienyl)alanine methyl ester; or N-[2(S)-(L-pyroglutamyl)amino-3(S)-methylpentyl]-N-(1-naphthylmethyl)glycyl-(2-thienyl)alanine;

or a pharmaceutically acceptable salt thereof.

10. A compound which inhibits farnesyl-protein transferase which is:

N-(1-Naphthylmethyl)-N-[2(S)-((pyroglutamyl)amino)-3(S)-methylpentyl]-glycyl-methionine

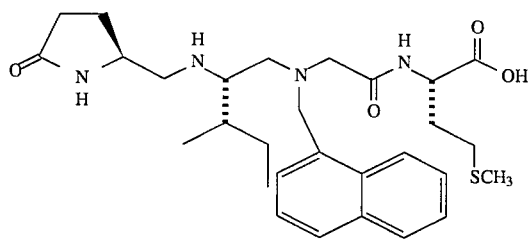

or the pharmaceutically acceptable salts thereof.

11. A compound which inhibits farnesyl-protein transferase which is:

N-(1-Naphthylmethyl)-N-[2(S)-((pyroglutamyl)amino)-3(S)-methylpentyl]-glycyl-methionine methyl ester

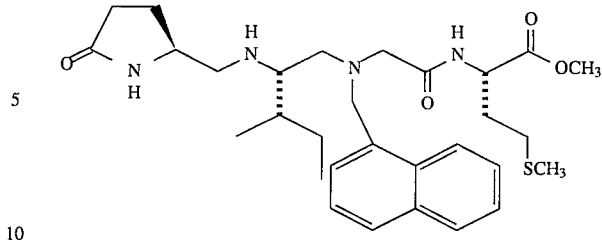

or the pharmaceutically acceptable salt thereof.

12. A compound which inhibits farnesyl-protein transferase which is:

N-(1-Naphthylmethyl)-N-[2(S)-((pyroglutamyl)amino)-3(S)-methylpentyl]-glycyl-methionine isopropyl ester

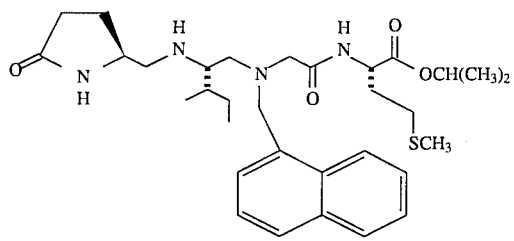

or the pharmaceutically acceptable salt thereof.

13. A compound which inhibits farnesyl-protein transferase which is:

N-(1-Naphthylmethyl)-N-[2(S)-((pyroglutamyl)amino)-3(S)-methylpentyl]-glycyl-methionine t-butyl ester

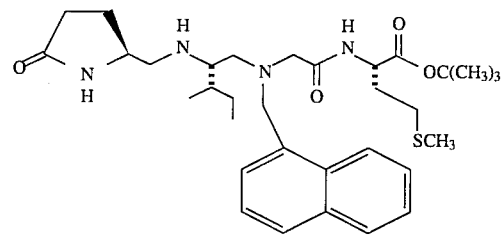

or the pharmaceutically acceptable salt thereof.

14. A compound which inhibits farnesyl-protein transferase which is:

N-(1-Naphthylmethyl)-N-[2(S)-((imidazol-4-ylacetyl)amino)-3(S)-methylpentyl]-glycyl-methionine

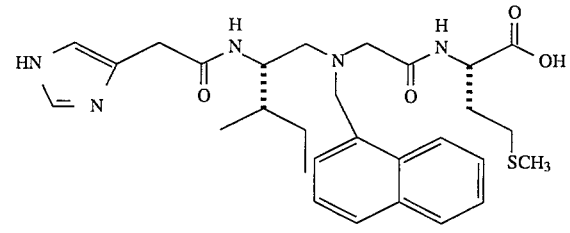

or the pharmaceutically acceptable salt thereof.

15. A compound which inhibits farnesyl-protein transferase which is:

N-(1-Naphthylmethyl)-N-[2(S)-((imidazol-4-ylacetyl)amino)-3(S)-methylpentyl]-glycyl-methionine methyl ester

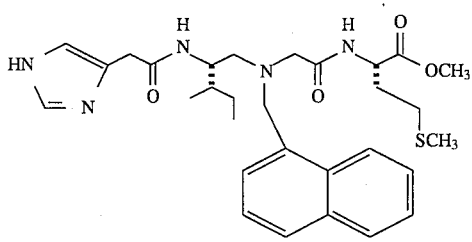

or the pharmaceutically acceptable salt thereof.

16. A pharmaceutical composition comprising a pharmaceutical carrier, and dispersed therein, a therapeutically effective amount of a compound of claim 1.

17. A pharmaceutical composition comprising a pharmaceutical carder, and dispersed therein, a therapeutically effective amount of a compound of claim 2.

18. A pharmaceutical composition comprising a pharmaceutical carder, and dispersed therein, a therapeutically effective amount of a compound of claim 3.

19. A pharmaceutical composition comprising a pharmaceutical carder, and dispersed therein, a therapeutically effective amount of a compound of claim 4.

20. A pharmaceutical composition comprising a pharmaceutical carrier, and dispersed therein, a therapeutically effective amount of a compound of claim 9.

21. A method for inhibiting farnesylation of Ras protein which comprises administering to a mammal in need thereof a therapeutically effective amount of the composition of claim 16.

22. A method for inhibiting farnesylation of Ras protein which comprises administering to a mammal in need thereof a therapeutically effective amount of the composition of claim 17.

23. A method for inhibiting farnesylation of Ras protein which comprises administering to a mammal in need thereof a therapeutically effective amount of the composition of claim 18.

24. A method for inhibiting farnesylation of Ras protein which comprises administering to a mammal in need thereof a therapeutically effective amount of the composition of claim 19.

25. A method for inhibiting farnesylation of Ras protein which comprises administering to a mammal in need thereof a therapeutically effective amount of the composition of claim 20.

* * * * *

UNITED STATES PATENT AND TRADEMARK OFFICE
CERTIFICATE OF CORRECTION

Page 1 of 2

PATENT NO. : 5,576,293
DATED: November 19, 1996
INVENTOR(S): S. Jane deSolms, Victor M. Garsky, Elizabeth A. Giuliani, Robert P. Gomez, Samuel L. Graham, Gerald E. Stokker and Catherine M. Wiscount It is certified that errors by the USPTO appear in the above-identified patent and that said Letters Patent is hereby corrected as shown below:

In Column 78, at line 46, insert the word -- or --.

In Column 87, at lines 51-61, the structure should be:

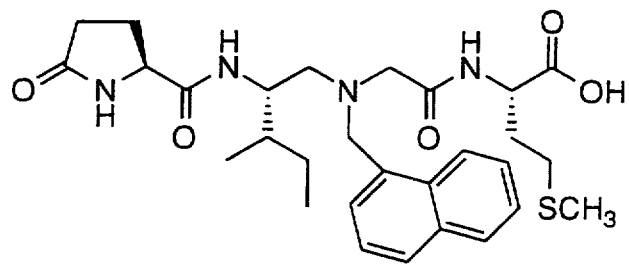

In Column 88, at lines 1-10, the structure should be:

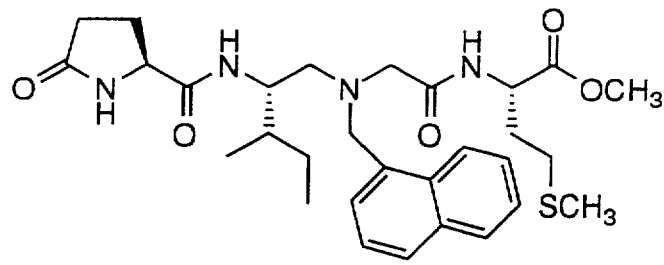

UNITED STATES PATENT AND TRADEMARK OFFICE
CERTIFICATE OF CORRECTION

Page 2 of 2

PATENT NO. :   5,576,293
DATED:         November 19, 1996, 1996
INVENTOR(S):   S. Jane deSolms, Victor M. Garsky, Elizabeth A. Giuliani, Robert P. Gomez, Samuel L. Graham, Gerald E. Stokker and Catherine M. Wiscount In Column 88, at lines 18-28, the structure should be:

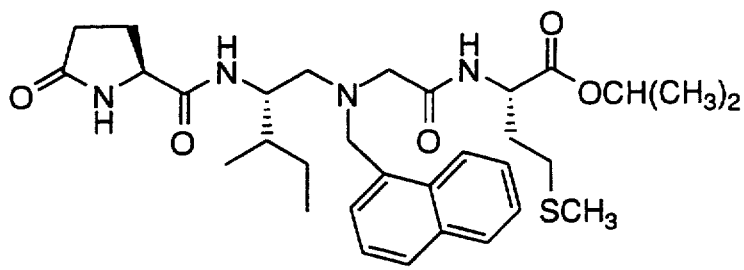

In Column 88, at lines 34-44, the structure should be:

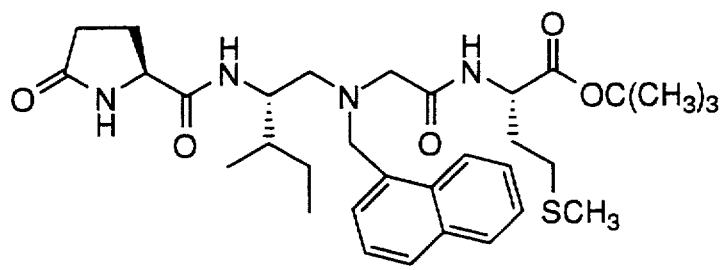

Signed and Sealed this

Eleventh Day of March, 1997

Attest:

BRUCE LEHMAN

Attesting Officer

Commissioner of Patents and Trademarks